US009526451B1

(12) United States Patent
Berme

(10) Patent No.: US 9,526,451 B1
(45) Date of Patent: Dec. 27, 2016

(54) FORCE MEASUREMENT SYSTEM

(71) Applicant: Bertec Corporation, Columbus, OH (US)

(72) Inventor: Necip Berme, Worthington, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 14/921,571

(22) Filed: Oct. 23, 2015

Related U.S. Application Data

(63) Continuation-in-part of application No. 14/580,160, filed on Dec. 22, 2014, now Pat. No. 9,168,420, which is a continuation-in-part of application No. 14/015,535, filed on Aug. 30, 2013, now Pat. No. 8,915,149, which is a continuation-in-part of
(Continued)

(51) Int. Cl.
*A61B 5/00* (2006.01)
*A63B 24/00* (2006.01)
*A63B 22/02* (2006.01)
*A63B 23/04* (2006.01)
*A61B 5/103* (2006.01)

(52) U.S. Cl.
CPC ............. *A61B 5/486* (2013.01); *A61B 5/1036* (2013.01); *A61B 5/4023* (2013.01); *A63B 22/02* (2013.01); *A63B 23/04* (2013.01); *A63B 24/0062* (2013.01); *A63B 2024/0068* (2013.01); *A63B 2220/51* (2013.01); *A63B 2220/802* (2013.01); *A63B 2220/803* (2013.01); *A63B 2220/805* (2013.01); *A63B 2220/806* (2013.01)

(58) Field of Classification Search
USPC ...................................................... 73/862.041
See application file for complete search history.

(56) References Cited

U.S. PATENT DOCUMENTS 4,739,848 A 4/1988 Tulloch
4,800,973 A 1/1989 Angel
(Continued)

OTHER PUBLICATIONS

Cutlip, R. et al., A comparison of different postures for scaffold end-frame disassembly, Applied Ergonomics, Oct. 2, 2000, vol. 31, Issue 5, pp. 507-513.
(Continued)

*Primary Examiner* — Lisa Caputo
*Assistant Examiner* — Octavia Hollington
(74) *Attorney, Agent, or Firm* — The Law Office of Patrick F. O'Reilly III, LLC

(57) ABSTRACT

A force measurement system includes an instrumented treadmill with one or more displaceable components having one or more respective surfaces for receiving one or more respective limbs of the subject, and at least one force transducer. The force measurement system further includes a data processing device configured to receive one or more load signals from the at least one force transducer, to convert the one or more load signals into one or more output load components, and to determine one or more gait parameters for the subject from the one or more output load components; and a sensory output device configured to receive at least one sensory output signal from the data processing device, and to generate at least one of a visual indicator, an audible indicator, and a tactile indicator that is based upon the at least one sensory output signal and provides biofeedback to the subject.

22 Claims, 37 Drawing Sheets

Related U.S. Application Data application No. 13/348,506, filed on Jan. 11, 2012, now Pat. No. 8,544,347.

(56) References Cited

U.S. PATENT DOCUMENTS

| | | |
|---|---|---|
| 4,880,069 A | 11/1989 | Bradley |
| 5,299,454 A * | 4/1994 | Fuglewicz ............ A63B 22/02 600/592 |
| 5,314,391 A | 5/1994 | Potash et al. |
| 5,368,532 A | 11/1994 | Farnet |
| 5,707,319 A | 1/1998 | Riley |
| 5,708,236 A | 1/1998 | Shaanan et al. |
| 5,750,937 A | 5/1998 | Johnson et al. |
| 6,038,488 A | 3/2000 | Barnes et al. |
| 6,052,114 A | 4/2000 | Morifuji |
| 6,113,237 A | 9/2000 | Ober et al. |
| 6,152,564 A | 11/2000 | Ober et al. |
| 6,222,137 B1 | 4/2001 | Handford |
| 6,295,878 B1 | 10/2001 | Berme |
| 6,354,155 B1 | 3/2002 | Berme |
| 6,389,883 B1 | 5/2002 | Berme et al. |
| 6,437,257 B1 | 8/2002 | Yoshida |
| 6,645,126 B1 | 11/2003 | Martin et al. |
| 6,738,065 B1 | 5/2004 | Even-Zohar |
| 6,774,885 B1 | 8/2004 | Even-Zohar |
| 6,797,894 B2 | 9/2004 | Montagnino et al. |
| 6,812,414 B2 | 11/2004 | Nakagawa |
| 6,878,100 B2 | 4/2005 | Frykman et al. |
| 6,936,016 B2 | 8/2005 | Berme et al. |
| 7,418,875 B2 | 9/2008 | Kohno et al. |
| 7,455,620 B2 | 11/2008 | Frykman et al. |
| 7,931,604 B2 | 4/2011 | Even-Zohar et al. |
| 7,989,713 B2 | 8/2011 | Hulburt et al. |
| 7,994,440 B2 | 8/2011 | Oseko et al. |
| 8,002,672 B2 | 8/2011 | Brunner |
| 8,030,582 B2 | 10/2011 | Tanida et al. |
| 8,152,640 B2 | 4/2012 | Shirakawa et al. |
| 8,181,541 B2 | 5/2012 | Berme |
| 8,204,710 B2 | 6/2012 | Walthert |
| 8,315,822 B2 | 11/2012 | Berme et al. |
| 8,315,823 B2 | 11/2012 | Berme et al. |
| 8,394,002 B2 | 3/2013 | Park |
| 8,444,580 B2 | 5/2013 | Ochi et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,622,747 B2 * | 1/2014 | Chu ................... A63B 22/0292 434/258 |
| 8,643,669 B1 | 2/2014 | Wilson et al. |
| 8,700,569 B1 | 4/2014 | Wilson et al. |
| 8,702,567 B2 * | 4/2014 | Hu .......................... A61H 3/00 482/8 |
| 8,704,855 B1 | 4/2014 | Berme et al. |
| 8,764,532 B1 | 7/2014 | Berme |
| 8,790,279 B2 | 7/2014 | Brunner |
| 8,845,494 B2 * | 9/2014 | Whitall .............. A63B 69/0028 482/54 |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 2003/0216656 A1 | 11/2003 | Berme et al. |
| 2008/0221487 A1 | 9/2008 | Even-Zohar et al. |
| 2008/0228110 A1 | 9/2008 | Berme |
| 2010/0131113 A1 | 5/2010 | Even-Zohar |
| 2011/0277562 A1 | 11/2011 | Berme |
| 2012/0266648 A1 | 10/2012 | Berme et al. |
| 2012/0271565 A1 | 10/2012 | Berme et al. |
| 2015/0096387 A1 | 4/2015 | Berme et al. |

OTHER PUBLICATIONS

First office action on the merits (Non-Final Rejection) in U.S. Appl. No. 13/348,506, mailed on Jan. 30, 2013.

Notice of Allowance in U.S. Appl. No. 13/348,506, mailed on Jun. 11, 2013.

First office action on the merits (Non-Final Rejection) in U.S. Appl. No. 14/015,535, mailed on Apr. 29, 2014.

Notice of Allowance in U.S. Appl. No. 14/015,535, mailed on Aug. 18, 2014.

First office action on the merits (Non-Final Rejection) in U.S. Appl. No. 14/580,160, mailed on Feb. 13, 2015.

Notice of Allowance in U.S. Appl. No. 14/580,160, mailed on Jun. 24, 2015.

* cited by examiner

FORCE MEASUREMENT SYSTEM

CROSS-REFERENCE TO RELATED APPLICATIONS

This is a continuation-in-part of U.S. Nonprovisional patent application Ser. No. 14/580,160, entitled "Force Measurement System", filed on Dec. 22, 2014, which is a continuation-in-part of U.S. Nonprovisional patent application Ser. No. 14/015,535, entitled "Force Measurement System", filed on Aug. 30, 2013, now U.S. Pat. No. 8,195,149; which is a continuation-in-part of U.S. Nonprovisional patent application Ser. No. 13/348,506, entitled "Force Measurement System Having a Plurality of Measurement Surfaces", filed on Jan. 11, 2012, now U.S. Pat. No. 8,544,347; the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force measurement systems. More particularly, the invention relates to a force measurement system that is particularly useful in the assessment of the balance of a subject.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

A balance assessment of a human subject is frequently performed using a specialized type of a force plate, which is generally known as a balance plate. A balance plate is a sensitive weighing scale, which in addition to measuring the weight of the subject, also measures the point of application of the weight. Typically, this is achieved by having either three or four instrumented feet, each measuring the force transmitted through it. Then, based on how much force each foot carries, the point of application of the total force (i.e., the body weight is calculated). A typical use of a balance plate involves monitoring the manner in which this point of application of the force (i.e., the center of pressure) changes as the subject stands on the plate. For a quietly standing subject, the center of pressure variation is an indication of the amount of physiological sway that the subject experiences. Generally, a small center of pressure variation demonstrates that the subject is essentially stable, whereas a large center of pressure variation in quiet stance is interpreted as an indication that the subject may have difficulty maintaining his or her own balance, and may be in danger of sustaining a fall in normal daily living. Balance plates frequently are used in clinics and assisted-living environments by a clinicians and/or physical therapists who regularly carry the plate from one facility to another. Thus, it is highly desirable for a balance plate to be readily portable.

During a balance assessment, if it is desired to make independent measurements under each foot of a subject, two balance plates are typically either placed side-by-side or mounted on a common base. This arrangement permits a determination of the weight that is carried by each leg of the subject, and if there is a deficiency in one of the legs. However, using two separate plates requires carrying additional hardware. Also, the operator has to make sure that the plates are not touching one another as the patient steps on and off the system so that an accurate measurement of each leg can be obtained. When two plates are mounted on one common base, the system becomes significantly heavier, and thus, more difficult to transport. Both conventional two plate systems also have the disadvantage that measurement from each plate is recorded independently, and poses not only an inconvenience, but also increases the possibility of inadvertently mixing the left and right signals.

Also, because many subjects that are tested on a balance plate have a balance disorder or a potential balance problem, it is very important that subjects are able to easily step on and off of the plate. Thus, it is highly desirable for the balance plate to have as low a profile as possible. Although, on a conventional balance plate, the force measuring feet are placed underneath the surface on which the patient stands, which increases the overall height of the instrument and consequently makes it more difficult for a patient having balance disorders to step on and off the plate.

In order to assess the walking or running ability of a particular subject, treadmills are often used in the context of a gait lab. However, while walking or running on the treadmill, subjects frequently have a difficult time maintaining a generally central position on the treadmill belt (i.e., between the front end and the rear end of the treadmill along a length dimension of the treadmill). Maintaining a central position on the treadmill belt is particularly a problem for subjects with gait disorders. The inability to maintain a generally central position on the treadmill belt can pose various safety concerns during the testing of a subject. For example, if the subject is too close to the rear end of the treadmill while walking or running on the treadmill, he or she may fall off the treadmill and sustain potential injuries. Conversely, if the subject is too close to the front end of the treadmill while walking or running on the treadmill, he or she may collide with the handrail of the treadmill, and potentially sustain injuries. Also, conventional treadmills do not provide the subject with any biofeedback with regard to his or her performance while walking or running on the treadmill.

What is needed, therefore, is a force measurement system that is in the form of a single force plate having two or more independent measurement surfaces for assessing the balance of a subject. Moreover, a force measurement system is needed that is readily portable, and thus, easy for an operator to transport from place to place. Additionally, a need exists for a force measurement system that has a low profile so that it is easier for subjects, such as patients having balance disorders or potential balance problems to step on and off the apparatus. Furthermore, a force measurement system also is needed that includes a treadmill with automatic means for regulating the speed of one or more treadmill belts in accordance with the position of the subject so that the subject maintains a generally central position on the treadmill belt(s) between the front end and the rear end of the treadmill while walking or running on the treadmill. In addition, a need exists for a force measurement system that provides a subject with biofeedback while he or she is walking or running on the treadmill so that the subject is able to monitor his or her performance, and make corrections, if required.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one aspect of the present invention, there is provided a force measurement system comprising an instrumented treadmill configured to receive a subject, the instrumented treadmill including one or more displaceable components, the one or more displaceable components having one or more respective surfaces for receiving one or more respective limbs of the subject; and at least one force transducer, the at least one force transducer configured to sense one or more measured quantities and output one or more load signals that are representative of one or more loads being applied to the one or more respective surfaces of the one or more displaceable components by the subject; a data processing device operatively coupled to the at least one force transducer of the instrumented treadmill, the data processing device configured to receive the one or more load signals that are representative of the one or more loads being applied to the one or more respective surfaces of the one or more displaceable components by the subject, to convert the one or more load signals into one or more output load components, and to determine one or more gait parameters for the subject from the one or more output load components, the data processing device further configured to compare the one or more gait parameters determined for the subject to one or more respective baseline values or to compare a first of the one or more gait parameters for the subject to a second of the one or more gait parameters for the subject, the data processing device additionally configured to determine how closely the one or more gait parameters determined for the subject conform to the one or more respective baseline values or to determine how closely the first of the one or more gait parameters for the subject conforms to the second of the one or more gait parameters for the subject, the data processing device further configured to generate a sensory output signal based upon the conformity of the one or more gait parameters of the subject to the one or more respective baseline values or to generate a sensory output signal based upon the conformity of the first of the one or more gait parameters of the subject to the second of the one or more gait parameters of the subject; and a sensory output device operatively coupled to the data processing device, the sensory output device configured to receive the sensory output signal from the data processing device, to generate at least one of a visual indicator, an audible indicator, and a tactile indicator that is based upon the sensory output signal, and to output the at least one of the visual indicator, the audible indicator, and the tactile indicator to the subject in order to provide biofeedback as to conformity of the one or more gait parameters of the subject to the one or more respective baseline values or biofeedback as to conformity of the first of the one or more gait parameters of the subject to the second of the one or more gait parameters of the subject.

In a further embodiment of this aspect of the present invention, the one or more gait parameters determined for the subject comprise at least one of: (i) a step length of the subject, (ii) a maximum sway range of a center of pressure of the subject, (iii) a maximum sway range of the center of gravity of the subject, (iv) a time duration of a single leg stance of the subject, and (v) a time duration of a single leg swing of the subject.

In yet a further embodiment, the data processing device is configured to compare the one or more gait parameters determined for the subject to one or more respective baseline values in order to determine gait deviations from a normal standard, the data processing device additionally being configured to determine how closely the one or more gait parameters determined for the subject conform to the one or more respective baseline values, and to generate the sensory output signal based upon the conformity of the one or more gait parameters of the subject to the one or more respective baseline values so as to provide biofeedback indicative of the gait deviations from the normal standard.

In still a further embodiment, the data processing device is configured to compare a first of the one or more gait parameters for the subject to a second of the one or more gait parameters for the subject in order to determine asymmetry between a right leg and a left leg of the subject, the data processing device additionally being configured to determine how closely the first of the one or more gait parameters for the subject conforms to the second of the one or more gait parameters for the subject, and to generate the sensory output signal based upon the conformity of the first of the one or more gait parameters of the subject to the second of the one or more gait parameters of the subject so as to provide biofeedback indicative of the asymmetry between a right leg and a left leg of the subject.

In yet a further embodiment, the first and second of the one or more gait parameters determined for the subject comprise at least one of: (i) first and second time durations for respective right and left leg stance phases of the subject, (ii) first and second time durations for respective right and left leg swing phases of the subject, (iii) first and second step lengths for the respective right and left legs of the subject; and (iv) first and second ground reaction forces for the respective right and left legs of the subject.

In still a further embodiment, the sensory output device comprises a visual display device having an output screen, and the visual display device is configured to generate the visual indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

In yet a further embodiment, the sensory output device comprises a light emitting device, and the light emitting device is configured to generate the visual indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

In still a further embodiment, the sensory output device comprises an audio headset configured to be worn on a head of the subject or a speaker disposed on, or proximate to the instrumented treadmill, and the audio headset or speaker is configured to generate the audible indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

In yet a further embodiment, the sensory output device comprises a vibratory device configured to be worn by the subject, and the vibratory device is configured to generate the tactile indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

In still a further embodiment, the force measurement system further includes a body position measurement system, the body position measurement system configured to detect the position of an upper body portion of the subject and output one or more position data signals that are representative of the position of the upper body portion of the subject, the upper body portion of the subject being disposed above the feet of the subject. In this further embodiment, the one or more gait parameters that the data processing device is configured to determine from the one or more load signals comprise center of pressure values for the subject. The data processing device is further configured to determine a right and left leg step length of the subject from the center of pressure values for the subject, to determine how closely the right leg step length of the subject conforms to the left leg step length of the subject, and to generate the sensory output signal for the biofeedback based upon the conformity of the right leg step length of the subject to the left leg step length of the subject. The data processing device is further operatively coupled to the body position measurement system, the data processing device being configured to receive the one or more position data signals from the body position measurement system, and to determine a center of gravity for the subject from the one or more position data signals. Also, in this further embodiment, the data processing device is further configured to determine a postural sway of the subject using the center of gravity determined from the one or more position data signals, to determine how closely the postural sway of the subject conforms to one or postural sway baseline values, and to additionally generate the sensory output signal for the biofeedback based upon the conformity of the postural sway of the subject to the one or postural sway baseline values.

In yet a further embodiment, the body position measurement system comprises at least one of: (i) an infrared detector, (ii) an ultrasonic detector, (iii) a position detection device with mechanical linkage means, (iv) one or more inertial measurement units configured to be coupled to the upper body portion of the subject, (v) one or more video cameras, and (vi) a motion capture system.

In accordance with another aspect of the present invention, there is provided a treadmill system with biofeedback, comprising a treadmill configured to receive a person, the treadmill including one or more displaceable components, the one or more displaceable components having one or more respective surfaces for receiving one or more respective limbs of the person; and one or more actuator mechanisms coupled to the one or more displaceable components, the one or more actuator mechanisms configured to displace the one or more displaceable components; a body position measurement system, the body position measurement system configured to measure a position of a body portion of the person on the treadmill and output one or more signals that are representative of the position of the body portion of the person on the treadmill; a data processing device operatively coupled to the body position measurement system, the data processing device configured to receive the one or more signals that are representative of the position of the body portion of the person, to convert the one or more signals into one or more body position values, and to determine one or more gait parameters for the person from the one or more body position values, the data processing device further configured to compare the one or more gait parameters determined for the person to one or more respective baseline values or to compare a first of the one or more gait parameters for the person to a second of the one or more gait parameters for the person, the data processing device additionally configured to determine how closely the one or more gait parameters determined for the person conform to the one or more respective baseline values or to determine how closely the first of the one or more gait parameters for the person conforms to the second of the one or more gait parameters for the person, the data processing device further configured to generate a sensory output signal based upon the conformity of the one or more gait parameters of the person to the one or more respective baseline values or to generate a sensory output signal based upon the conformity of the first of the one or more gait parameters of the person to the second of the one or more gait parameters of the person; and a sensory output device operatively coupled to the data processing device, the sensory output device configured to receive the sensory output signal from the data processing device, to generate at least one of a visual indicator, an audible indicator, and a tactile indicator that is based upon the sensory output signal, and to output the at least one of the visual indicator, the audible indicator, and the tactile indicator to the person in order to provide biofeedback as to conformity of the one or more gait parameters of the person to the one or more respective baseline values or biofeedback as to conformity of the first of the one or more gait parameters of the person to the second of the one or more gait parameters of the person.

In a further embodiment of this aspect of the present invention, the one or more gait parameters determined by the data processing device for the person comprise at least one of: (i) a step length of the person, and (ii) a maximum sway range of the center of gravity of the person.

In yet a further embodiment, the data processing device is configured to compare the one or more gait parameters determined for the person to one or more respective baseline values in order to determine gait deviations from a normal standard, the data processing device additionally being configured to determine how closely the one or more gait parameters determined for the person conform to the one or more respective baseline values, and to generate the sensory output signal based upon the conformity of the one or more gait parameters of the person to the one or more respective baseline values so as to provide biofeedback indicative of the gait deviations from the normal standard. The baseline values and the normative standard may be based upon either the subject's own previous gait data (e.g., when the subject was exhibiting typical or normal gait characteristics before an injury) or gait data from a population of other subjects (i.e., so the subject is able to be compared to typical gait data for a population of normal subjects without gait disabilities).

In still a further embodiment, the data processing device is configured to compare a first of the one or more gait parameters for the person to a second of the one or more gait parameters for the person in order to determine asymmetry between a right leg and a left leg of the person, the data processing device additionally being configured to determine how closely the first of the one or more gait parameters for the person conforms to the second of the one or more gait parameters for the person, and to generate the sensory output signal based upon the conformity of the first of the one or more gait parameters of the person to the second of the one or more gait parameters of the person so as to provide biofeedback indicative of the asymmetry between a right leg and a left leg of the person.

In yet a further embodiment, the sensory output device comprises a visual display device having an output screen, and the visual display device is configured to generate the visual indicator that provides biofeedback to the person as to conformity of the one or more gait parameters of the person to the one or more respective baseline values or biofeedback as to conformity of the first of the one or more gait parameters of the person to the second of the one or more gait parameters of the person.

In still a further embodiment, the sensory output device comprises a light emitting device, and the light emitting device is configured to generate the visual indicator that provides biofeedback to the person as to conformity of the one or more gait parameters of the person to the one or more respective baseline values or biofeedback as to conformity of the first of the one or more gait parameters of the person to the second of the one or more gait parameters of the person.

In yet a further embodiment, the sensory output device comprises an audio headset configured to be worn on a head of the person or a speaker disposed on, or proximate to the treadmill, and the audio headset or speaker is configured to generate the audible indicator that provides biofeedback to the person as to conformity of the one or more gait parameters of the person to the one or more respective baseline values or biofeedback as to conformity of the first of the one or more gait parameters of the person to the second of the one or more gait parameters of the person.

In still a further embodiment, the sensory output device comprises a vibratory device configured to be worn by the person, and the vibratory device is configured to generate the tactile indicator that provides biofeedback to the person as to conformity of the one or more gait parameters of the person to the one or more respective baseline values or biofeedback as to conformity of the first of the one or more gait parameters of the person to the second of the one or more gait parameters of the person.

In yet a further embodiment, the body position measurement system comprises at least one of: (i) an infrared detector, (ii) an ultrasonic detector, (iii) a position detection device with mechanical linkage means, (iv) one or more inertial measurement units configured to be coupled to the body portion of the person, (v) one or more video cameras, and (vi) a motion capture system.

In accordance with yet another aspect of the present invention, there is provided a force measurement system comprising an instrumented treadmill configured to receive a subject, the instrumented treadmill including one or more displaceable components, the one or more displaceable components having one or more respective surfaces for receiving one or more respective limbs of the subject; and at least one force transducer, the at least one force transducer configured to sense one or more measured quantities and output one or more load signals that are representative of one or more loads being applied to the one or more respective surfaces of the one or more displaceable components by the subject; a data processing device operatively coupled to the at least one force transducer of the instrumented treadmill, the data processing device configured to receive the one or more load signals that are representative of the one or more loads being applied to the one or more respective surfaces of the one or more displaceable components by the subject, to convert the one or more load signals into one or more output load components, and to determine one or more gait parameters for the subject from the one or more output load components, the data processing device further configured to generate at least one sensory output signal based upon the one or more gait parameters for the subject; and a sensory output device operatively coupled to the data processing device, the sensory output device configured to receive the at least one sensory output signal from the data processing device, to generate at least one of a visual indicator, an audible indicator, and a tactile indicator that is based upon the at least one sensory output signal, and to output the at least one of the visual indicator, the audible indicator, and the tactile indicator to the subject in order to provide real-time biofeedback as to a manner in which the one or more gait parameters of the subject change over time.

In a further embodiment of this aspect of the present invention, the one or more displaceable components comprise a first displaceable component and a second displaceable component, the first displaceable component having a respective first surface for receiving a respective first limb of the subject and the second displaceable component having a respective second surface for receiving a respective second limb of the subject, and the at least one force transducer comprises at least one first force transducer, the at least one first force transducer configured to sense one or more measured quantities and output one or more first load signals that are representative of forces and/or moments being applied to the first surface by the subject, and at least one second force transducer, the at least second force transducer configured to sense one or more measured quantities and output one or more second load signals that are representative of forces and/or moments being applied to the second surface by the subject. Also, in this further embodiment, the data processing device is configured to receive the one or more first load signals that are representative of forces and/or moments being applied to the first surface and to convert the one or more first load signals into one or more first output load components, and to receive the one or more second load signals that are representative of forces and/or moments being applied to the second surface and to convert the one or more second load signals into one or more second output load components, the data processing device further configured to determine one or more first gait parameters for the subject from the one or more first output load components and to determine one or more second gait parameters for the subject from the one or more second output load components, the data processing device additionally configured to generate the at least one sensory output signal based upon the one or more first gait parameters and the one or more second gait parameters; and the sensory output device is configured to generate at least one of a first visual indicator, a first audible indicator, and a first tactile indicator for the one or more first gait parameters of the subject based upon the at least one sensory output signal and at least one of a second visual indicator, a second audible indicator, and a second tactile indicator for the one or more second gait parameters of the subject based upon the at least one sensory output signal, and output the at least one of the first visual indicator, the first audible indicator, and the first tactile indicator and the at least one of the second visual indicator, the second audible indicator, and the second tactile indicator to the subject in order to provide real-time biofeedback as to a manner in which the one or more first and second gait parameters of the subject change over time.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

A. First Embodiment

Figure 1:
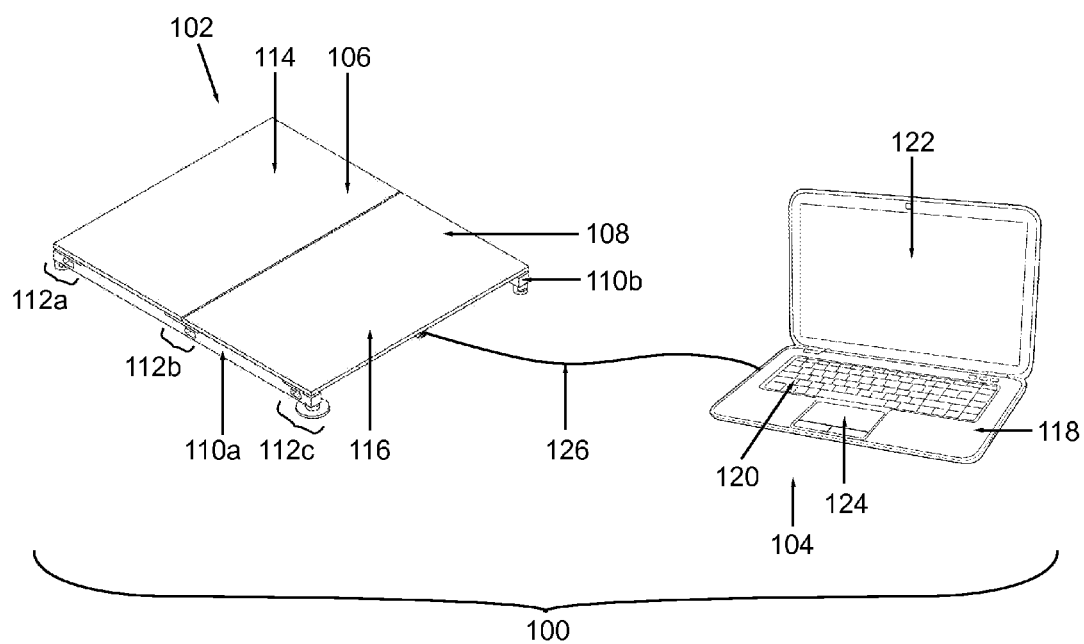
FIG. 1 is a perspective view of a dual force plate system according to a first embodiment of the invention.

A first embodiment of a dual force plate system is seen generally at 100 in FIG. 1. The dual force plate system 100 generally comprises a dual force plate assembly 102 operatively coupled to a data acquisition/data processing device 104 (i.e., a data acquisition and processing device) by virtue of an electrical cable 126. In the first embodiment, the dual force plate assembly 102 for receiving a subject utilizes a continuous force transducer beam design. In a preferred embodiment of the invention, the electrical cable 126 is used for data transmission, as well as for providing power to the dual force plate assembly 102. Preferably, the electrical cable 126 contains a plurality of electrical wires bundled together, with at least one wire being used for power and at least another wire being used for transmitting data. The bundling of the power and data transmission wires into a single electrical cable 126 advantageously creates a simpler and more efficient design. In addition, it enhances the safety of the testing environment when human subjects are being tested on the dual force plate assembly 102. However, it is to be understood that the dual force plate assembly 102 can be operatively coupled to the data acquisition/data processing device 104 using other signal transmission means, such as a wireless data transmission system. If a wireless data transmission system is employed, it is preferable to provide the dual force plate assembly 102 with a separate power supply in the form of an internal power supply or a dedicated external power supply.

Referring again to FIG. 1, it can be seen that the dual force plate assembly 102 according to the first embodiment of the invention, includes a first plate component 106, a second plate component 108, and continuous force transducer beams 110a, 110b mounted on opposite lateral sides of the first plate component 106 and second plate component 108. As depicted in FIG. 1, the continuous force transducer beams 110a, 110b extend substantially the combined width of the first plate component 106 and second plate component 108. Each continuous force transducer beam 110a, 110b includes a plurality of force transducer elements 112a, 112b, 112c disposed along the length thereof. The first plate component 106 has a top surface 114 that is configured to receive a first portion of a body of a subject. Similarly, the second plate component 108 has a top surface 116 that is configured to receive a second portion of a body of a subject. In a preferred embodiment, a subject stands in an upright position on the dual force plate assembly 102 and each foot of the subject is placed on the top surfaces 114, 116 of a respective plate component 106, 108 (i.e., one foot on the top surface 114 of the first plate component 106 and the other foot on the top surface 116 of the second plate component 108).

As shown in FIG. 1, the data acquisition/data processing device 104 (e.g., in the form of a laptop digital computer) generally includes a base portion 118 with a central processing unit (CPU) disposed therein for collecting and processing the data that is received from the dual force plate assembly 102, and a plurality of devices 120-124 operatively coupled to the central processing unit (CPU) in the base portion 118. Preferably, the devices that are operatively coupled to the central processing unit (CPU) comprise user input devices 120, 124 in the form of a keyboard 120 and a touchpad 124, as well as a graphical user interface in the form of a laptop LCD screen 122. While a laptop type computing system is depicted in FIG. 1, one of ordinary skill in the art will appreciate that another type of data acquisition/data processing device 104 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse). In addition, rather than providing a data acquisition/data processing device 104, it is to be understood that, in other embodiments, only a data acquisition device could be provided without departing from the spirit and the scope of the claimed invention.

Figure 2:
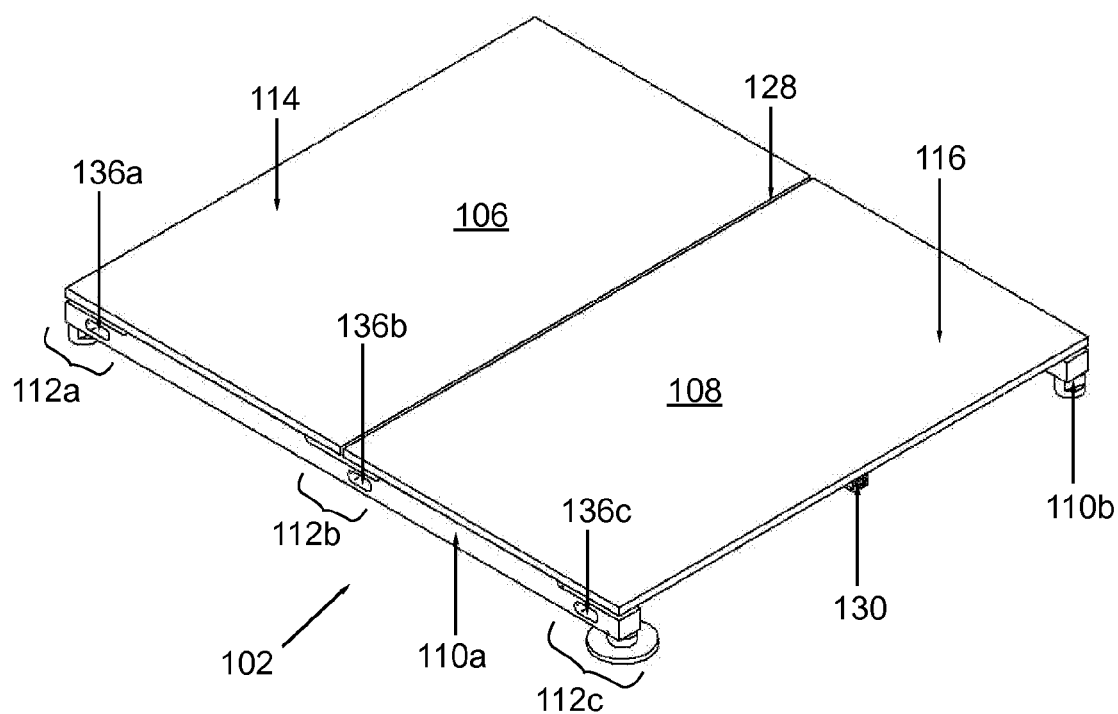
FIG. 2 is a perspective view of a dual force plate assembly of the dual force plate system according to the first embodiment of the invention.
Figure 3:
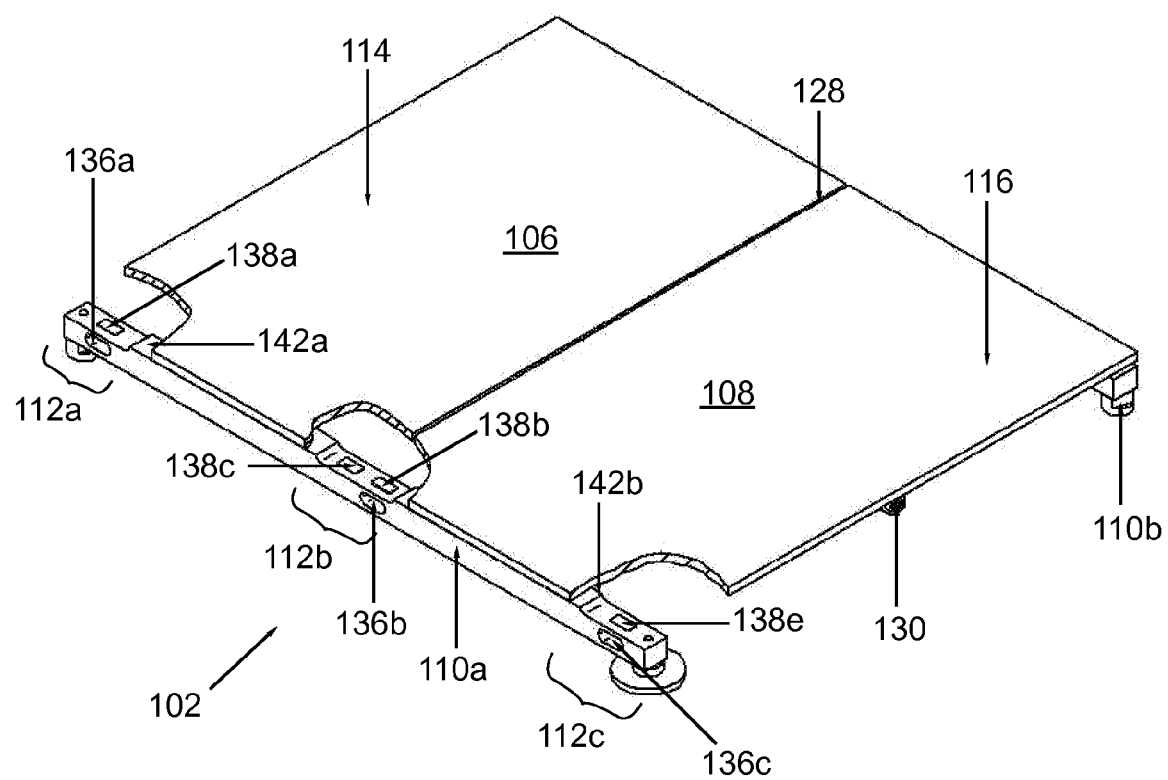
FIG. 3 is a cut-away perspective view of the dual force plate assembly of the dual force plate system according to the first embodiment of the invention.

Now, turning to FIGS. 2-4, the dual force plate assembly 102 will now be described in more detail. As described above, the dual force plate assembly 102 includes a first plate component 106 with a top surface 114 and a second plate component 108 with a top surface 116. A narrow gap 128 is provided between the first plate component 106 and the second plate component 108 so as to prevent interaction between the two plate components 106, 108. In a preferred embodiment, the narrow gap is between approximately 2 mm and approximately 3 mm, and more preferably, between 2 mm and 3 mm. As best shown in FIGS. 2 and 3, the gap 128 is continuous and completely separates the first plate component 106 from the second plate component 108 (i.e., the plate components 106, 108 do not contact one another at any location along the gap 128). In a preferred embodiment of the invention, the first and second plate components 106, 108 have a composite structure that includes an inverted top tray, structural steel members disposed inside the tray, and a metallic bottom sheet (e.g., an aluminum sheet). Alternatively, the first and second plate components 106, 108 could be provided with a composite structure that utilizes an aluminum honeycomb core inside the inverted top tray, rather than the structural steel members. In this variant of the invention, the honeycomb core is secured to the top tray and the bottom aluminum sheet using a metallic adhesive. This design allows the surface to be very stiff without adding excessive weight. In another variant of the invention, the first and second plate components 106, 108 are formed from a solid plate of material (e.g., a solid aluminum plate or a solid steel plate) with a high stiffness value. Regardless of the precise manner in which the first and second plate components 106, 108 are formed, it is highly desirable for the plate components 106, 108 to have a high stiffness value so as to ensure the structural integrity of the dual force plate assembly 102 when a subject having a substantial weight is disposed thereon. In an exemplary embodiment, the dual force plate assembly 102 is designed to have a natural frequency of at least 100 Hz and is capable of withstanding a subject weight of up to 2,225 Newtons (500 lbs.).

Advantageously, in a preferred embodiment, the dual force plate system 100, which includes dual force plate assembly 102, utilizes substantially the same number of components as a single force plate used in balance assessment.

Figure 4:
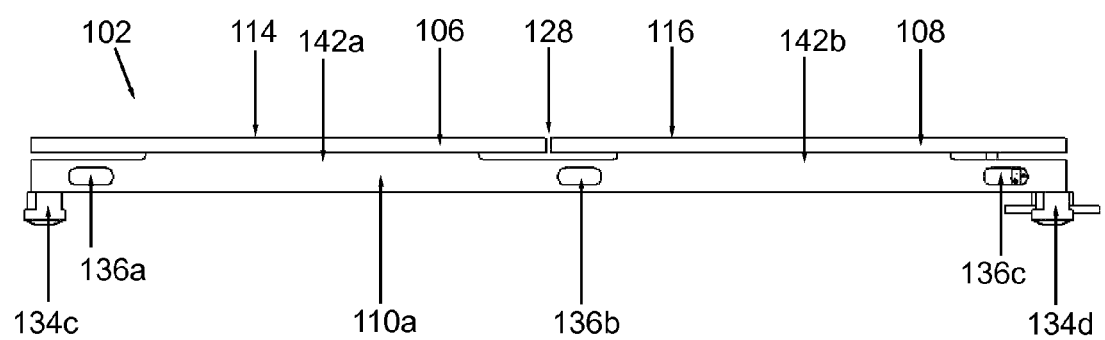
FIG. 4 is a side view of the dual force plate assembly of the dual force plate system according to the first embodiment of the invention.

Referring to FIGS. 2 and 4, it can be seen that each continuous force transducer beam 110a, 110b is attached to the underside of the first and second plate components 106, 108. In particular, as best shown in FIGS. 3 and 4, it can be seen that the top surface of each continuous force transducer beam 110a, 110b is provided with two protruding portions 142a, 142b. The protruding portions 142a, 142b are spaced apart from one another along the length of each continuous force transducer beam 110a, 110b. The top surface of the first protruding portion 142a on each of the continuous force transducer beams 110a, 110b is fixedly attached to the bottom surface of the first plate component 106, whereas the top surface of the second protruding portion 142b on each of the continuous force transducer beams 110a, 110b is fixedly attached to the bottom surface of the second plate component 108. It is highly advantageous that the first and second plate components 106, 108 only be connected to the protruding portions 142a, 142b of the continuous force transducer beams 110a, 110b so as to ensure that the total load applied to the top surfaces 114, 116 of the plate components 106, 108 is only transmitted through the force transducer elements 112a, 112b, 112c. Each force transducer beam 110a, 110b can be fixedly attached to each plate component 106, 108 by utilizing a plurality of different attachment means such as, but not limited to, threaded fasteners (e.g., screws) or different types of suitable adhesives (e.g., an adhesive designed for bonding metallic components to one another).

Figure 5:
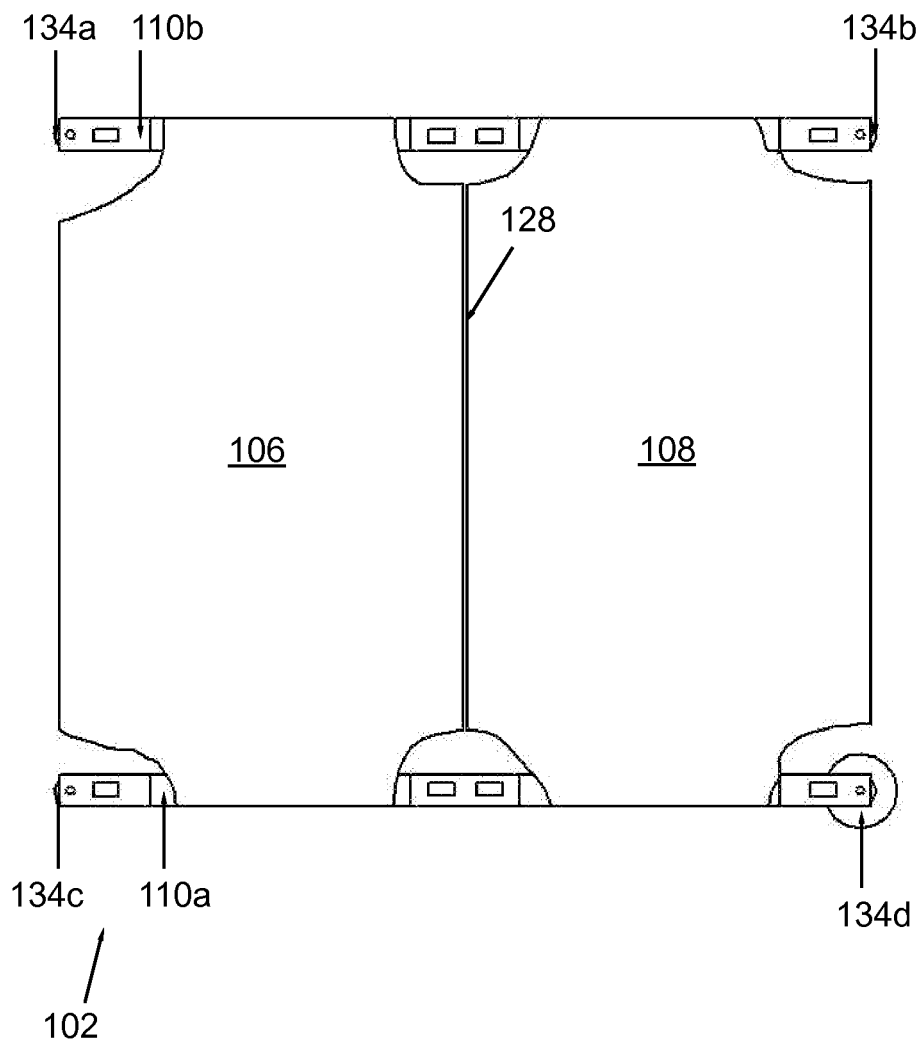
FIG. 5 is a cut-away top view of the dual force plate assembly of the dual force plate system according to the first embodiment of the invention.
Figure 6:
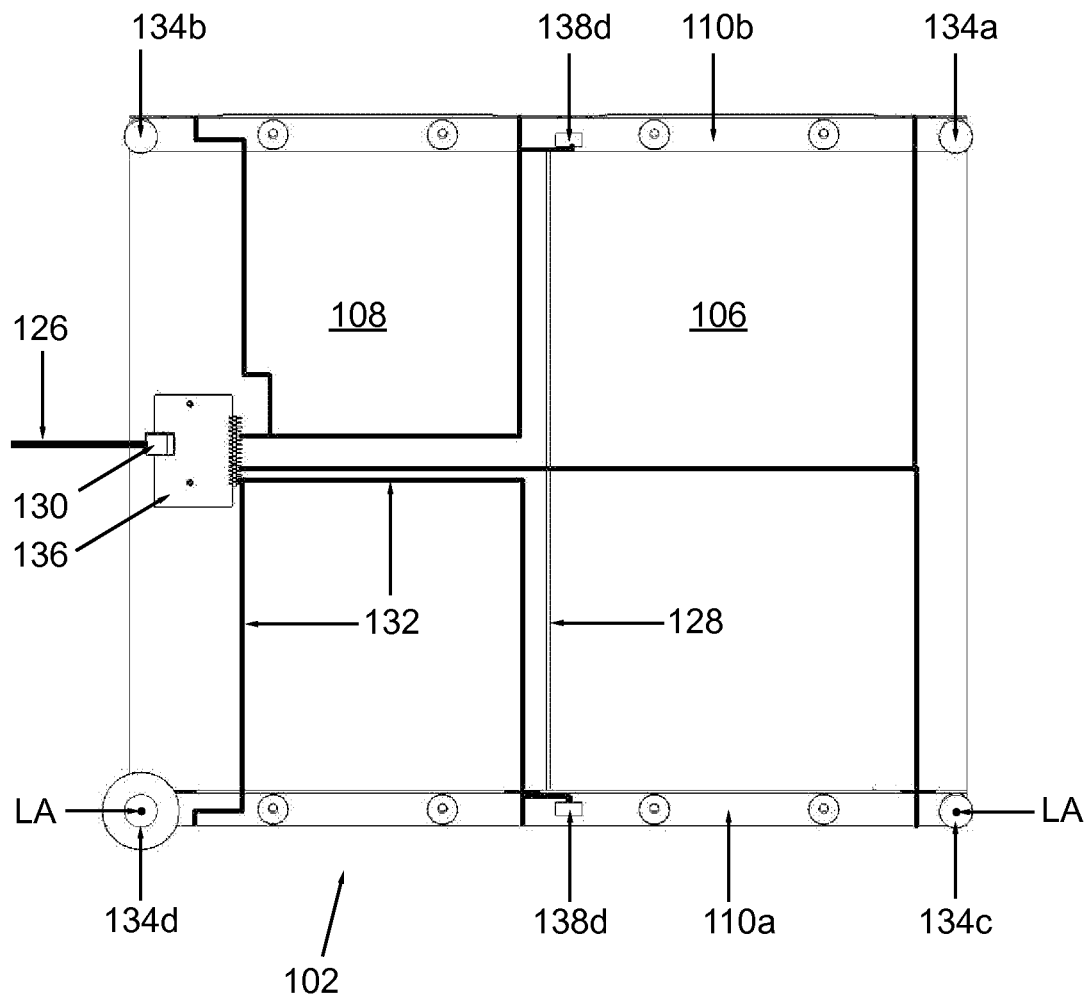
FIG. 6 is a bottom view of the dual force plate assembly of the dual force plate system according to the first embodiment of the invention.

As best illustrated in FIGS. 5 and 6, each force transducer beam 110a, 110b is provided with respective support feet 134c, 134d and 134a, 134b disposed at opposed longitudinal ends thereof. In the illustrated embodiment, the first of the two transducer beams 110a is provided with one non-adjustable support foot 134c near a first longitudinal end thereof and one adjustable support foot 134d near the other longitudinal end thereof, while the second of the two force transducer beams 110b is provided with two (2) non-adjustable support feet 134a, 134b disposed at opposed longitudinal ends thereof. The dual force plate assembly 102 is designed to be installed on a floor of a building or on any other rigid surface. The adjustable support foot 134d facilitates the leveling of the dual force plate assembly 102 on an uneven surface.

Referring again to FIGS. 5 and 6, the dual force plate assembly 102 is provided with a preamplifier board 136 mounted to the underside of the second plate component 108. As diagrammatically illustrated in FIG. 6, the preamplifier board 136 is operatively coupled to the pluralities of strain gages 138a-138e via a network of electrical wiring 132. In the depicted embodiment, the preamplifier board 136 is provided with a port 130 for receiving the end of the electrical cable 126 that operatively couples the force plate assembly 102 to the data acquisition/data processing device 104. The preamplifier board 136 is used to increase the magnitudes of the transducer analog voltages, and preferably, to convert the analog voltage signal(s) into digital voltage signal(s) as well. Advantageously, the preamplifier 136 is placed in close proximity to the two sets of force transducer elements 112a-112c in order to amplify the output voltage signal(s) before they are degraded by the effects of noise and interference while being transmitted over the substantial distance from the dual force plate assembly 102 to the data acquisition/data processing device 104. While the preamplifier board 136 is depicted as being mounted on the underside of the second plate component 108 in the illustrated embodiment of the invention, it is to be understood that, in other embodiments of the invention, the preamplifier board 136 could be alternatively mounted on the underside of the first plate component 106 or could be provided in the form of a standalone unit. Also, in yet another embodiment, an analog voltage signal(s) could be outputted from the preamplifier board 136 and then, subsequently converted to a digital voltage signal(s) at the data acquisition/data processing device 104.

In the cut-away perspective view illustrated in FIG. 3, it can be seen that the first of the two transducer beams 110a is provided with three force transducer elements 112a, 112b, 112c disposed along the length thereof. The first transducer element 112a is disposed at a first longitudinal end of the first transducer beam 110a. In a preferred embodiment of the invention, the first transducer element 112a comprises a longitudinal segment of the force transducer beam 110a, an aperture 136a disposed through the longitudinal segment of the force transducer beam 110a, and a plurality of strain gages 138a secured to the outer, top surface of the longitudinal segment of the force transducer beam 110a and substantially centered on the aperture 136a. The outer, top surface of the first transducer element 112a on which the plurality of strain gages 138a is disposed is generally opposite to the inner top surface of the aperture 136a. When a load is applied to the first plate component 106, the load is transferred to the longitudinal segment of the force transducer beam 110a that is associated with the first transducer element 112a, which operates as an elastically deformable structural member. The plurality of strain gages 138a is used to measure the deformation of the elastically deformable structural member (i.e., the longitudinal segment of the force transducer beam 110a) resulting from the vertical shear forces imparted on the member from the applied load. While in a preferred embodiment, the longitudinal segment of the force transducer beam 110a is provided with the aperture 136a therein to maximize the shear effect when the load is applied to the first plate component 106 by reducing the cross-sectional area of the beam 110a at the location of the aperture 136a, it is to be understood that the invention is not so limited. Rather, in other embodiments of the invention, the longitudinal segment of the force transducer beam 110a, which forms a component of the first transducer element 112a, is not provided with an aperture disposed therein.

As shown in FIG. 3, the second transducer element 112b is disposed in a central region of the force transducer beam 110a. In FIG. 2, it can be seen that the second force transducer element 112b extends across the gap 128 between the first plate component 106 and the second plate component 108 (i.e., the second force transducer element 112b bridges the gap 128 between the first plate component 106 and the second plate component 108). In particular, the second force transducer element 112b extends underneath the gap 128 between the first plate component 106 and the second plate component 108. Similar to the first transducer element 112a, the second transducer element 112b comprises a longitudinal segment of the force transducer beam 110a, an aperture 136b disposed through the longitudinal segment of the force transducer beam 110a, and a plurality of strain gages 138b secured to the outer, top surface of the longitudinal segment of the force transducer beam 110a and substantially centered on the aperture 136b. Also, as with the first transducer element 112a, the outer, top surface of the second transducer element 112b on which the plurality of strain gages 138b is mounted is oriented generally opposite to the inner top surface of the aperture 136b. However, unlike the first transducer element 112a, the second transducer element 112b also contains two additional pluralities of strain gages 138c, 138d mounted thereon for measuring the bending imparted on second transducer element 112b by a load applied to first plate component 106 and second plate component 108 (see FIGS. 3 and 6). The first additional plurality of strain gages 138c is mounted on the outer, top surface of the second transducer element 112b, horizontally spaced apart from the plurality of strain gages 138b. The second additional plurality of strain gages 138d is mounted on the outer, bottom surface of the second transducer element 112b, and is substantially vertically aligned with the first additional plurality of strain gages 138c (see FIG. 6). When the second transducer element 112b undergoes bending due to the application of a load on plate components 106, 108, the first additional plurality of strain gages 138c is configured to measure the deformation of the segmental portion of the force transducer beam 110a due to compression, while the second additional plurality of strain gages 138d is configured to measure the deformation of the segmental portion of the force transducer beam 110a due to tension. The shear force measurement performed by the plurality of strain gages 138b is analogous to that described above for the plurality of strain gages 138a of the first transducer element 112a. In addition, as described above for the first transducer element 112a, the aperture 136b is omitted from the second transducer element 112b in some embodiments of the invention.

Referring again to FIG. 3, it can be seen that a third transducer element 112c is disposed at a second longitudinal end of the first transducer beam 110a, which is opposite to its first longitudinal end on which the first transducer element 112a is disposed. In other words, the third transducer element 112c is generally in a mirrored relationship with respect to the first transducer element 112a. Like the first transducer element 112a, the third transducer element 112c comprises a longitudinal segment of the force transducer beam 110a, an aperture 136c disposed through the longitudinal segment of the force transducer beam 110a, and a plurality of strain gages 138e secured to the outer, top surface of the longitudinal segment of the force transducer beam 110a and substantially centered on the aperture 136c. The third transducer element 112c functions in the same manner as described above for the first transducer element 112a, except that the third transducer element 112c measures the shear force resulting from a load being applied to the second plate component 108, rather than the first plate component 106.

As shown in FIGS. 2-4, a second force transducer beam 110b is mounted on a side of the bottom surface of the first and second plate components 106, 108 that is opposite to the side of the bottom surface on which the first force transducer beam 110a is mounted. The second force transducer beam 110b is generally a mirror image of the first force transducer beam 110a. Like the first force transducer beam 110a, the second force transducer beam 110b contains first, second, and third force transducer elements 112a, 112b, 112c with respective apertures 136a, 136b, 136c disposed along the length thereof and pluralities of strain gages 138a-138e.

Figure 7:
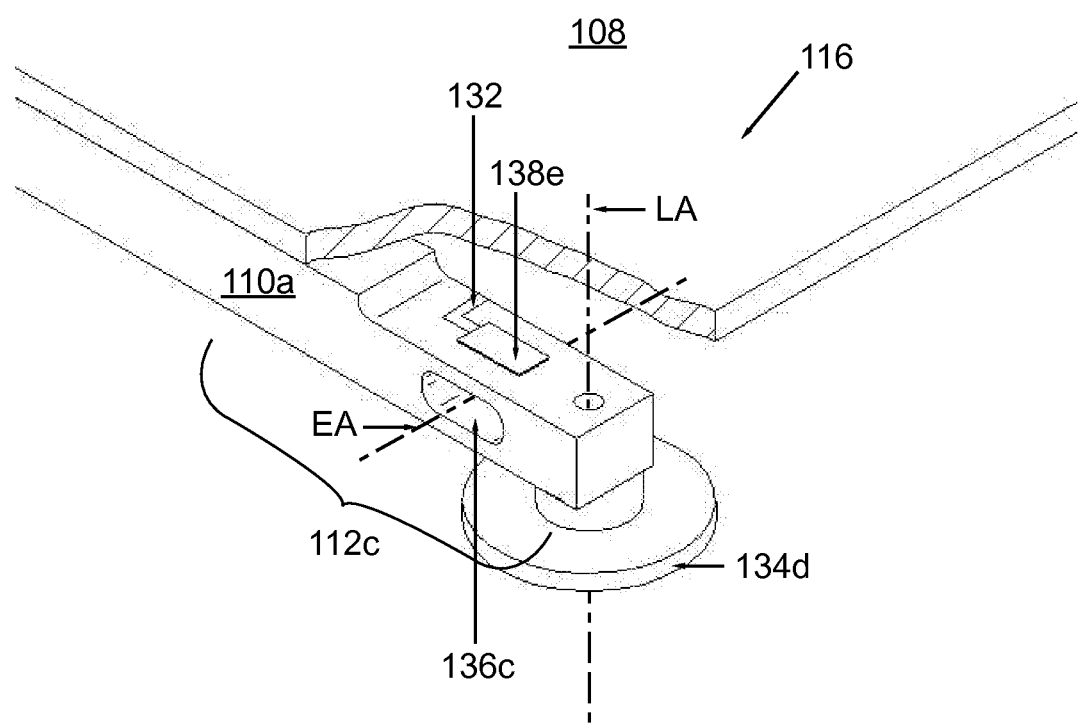
FIG. 7 is an enlarged, cut-away perspective view of a force transducer element of the dual force plate assembly according to the first embodiment of the invention, which depicts the placement of a strain gage thereon.

FIG. 7 depicts an enlarged view of force transducer element 112c. As shown in FIG. 7, the support foot 134d has a longitudinal axis LA that is disposed centrally therethrough, while the aperture 136c of the force transducer element 112c has an axis EA disposed centrally therethrough. In one or more embodiments, the structural arrangement of components illustrated in FIG. 7 is typically for each of the first and third transducer elements. The longitudinal axis LA of the support foot 134d is disposed substantially perpendicular to the extending direction of the aperture (i.e., substantially perpendicular to the axis EA). While the force transducer elements 112a, 112b, 112c shown in the drawings are beam-type force transducers, which have a generally elongated shape, one of ordinary skill in the art will appreciate that the present invention can be practiced with other types of force transducers such as, but not limited to, pylon-type force transducers. Typically, pylon-type force transducers have a plurality of strain gages adhered to the outer periphery of a cylindrically-shaped force transducer sensing element. In such a case, the force transducer elements 112a, 112c, which are disposed at opposite corners of the first and second plate components 106, 108, would be replaced with four (4) pylon-type force transducers disposed at each of the four (4) corners of the dual force plate assembly 102 (i.e., one (1) at each of the outer two corners of first plate component 106 and one (1) at each of the outer two corners of second plate component 108). In such an alternative arrangement, two force transducer elements, which are similar to force transducer elements 112b, would still be required for measuring the load transferred between the first plate component 106 and the second plate component 108.

Figure 8:
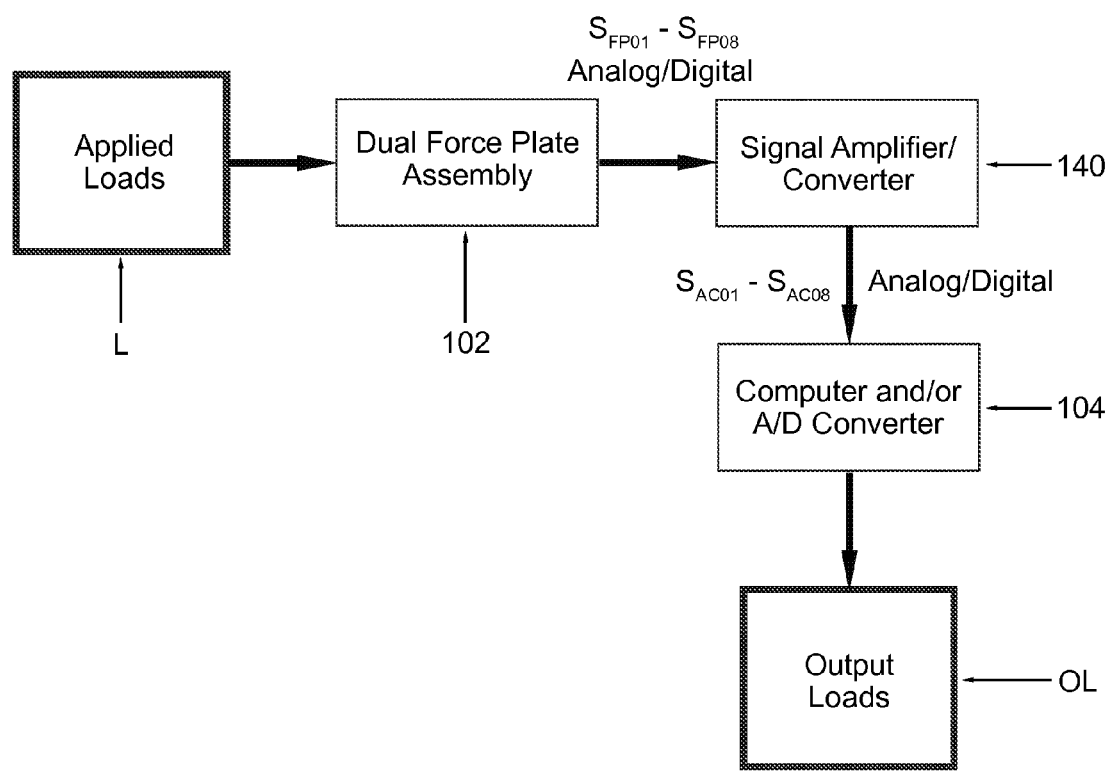
FIG. 8 is a block diagram illustrating a data acquisition/data processing system utilized in the embodiments of the force plate systems described herein.

FIG. 8 graphically illustrates the acquisition and processing of the load data carried out by the dual force plate system 100. Initially, as shown in FIG. 8, a load L is applied to the dual force plate assembly 102 by a subject disposed thereon. The load is transmitted from the first and second plate components 106, 108 to the two sets of force transducer elements 112a-112c. In a preferred embodiment of the invention, each of the force transducer elements 112a, 112c includes a plurality of strain gages wired in a Wheatstone bridge configuration, wherein the electrical resistance of each strain gage is altered when the associated longitudinal segment of the associated force transducer beam 110a, 110b undergoes deformation resulting from the load (i.e., forces and/or moments) acting on the first and second plate components 106, 108. In a preferred embodiment, the centrally-disposed force transducer elements 112b each include two (2) pluralities of strain gages wired in a Wheatstone bridge configuration, one for measuring shear and the other for measuring bending. Alternatively, rather than measuring both the shear force and bending moment, each centrally disposed transducer element 112b can measure a first bending moment at a first location along the length of the transducer element 112b and a second bending moment at a second location along the length of the transducer element 112b, the first location being spaced apart from the second location. For each plurality of strain gages disposed on the force transducer elements 112a-112c, the change in the electrical resistance of the strain gages brings about a consequential change in the output voltage of the Wheatstone bridge (i.e., a quantity representative of the load being applied to the measurement surface). Thus, the two sets of outer force transducer elements 112a, 112c transmit a total of four (4) analog output voltages (signals) to the preamplifier board 136, and the two centrally-disposed force transducer elements 112b also transmit a total of four (4) analog output voltages (signals) to the preamplifier board 136. As described above, the preamplifier board 136 is used to increase the magnitudes of the transducer analog voltages, and preferably, to convert the analog voltage signals into digital voltage signals as well. After which, the dual force plate assembly 102 transmits the force plate output signals $S_{FPO1}$-$S_{FPO8}$ to a main signal amplifier/converter 140. Depending on whether the preamplifier board 136 also includes an analog-to-digital (A/D) converter, the force plate output signals $S_{FPO1}$-$S_{FPO8}$ could be either in the form of analog signals or digital signals. The main signal amplifier/converter 140 further magnifies the force plate output signals $S_{FPO1}$-$S_{FPO8}$, and if the signals $S_{FPO1}$-$S_{FPO8}$ are of the analog-type (for a case where the preamplifier board 136 did not include an analog-to-digital (A/D) converter), it may also convert the analog signals to digital signals. Then, the signal amplifier/converter 140 transmits either the digital or analog signals $S_{ACO1}$-$S_{ACO8}$ to the data acquisition/data processing device 104 so that the forces and/or moments that are being applied to the surfaces of the dual force plate assembly 102 can be outputted to a user (i.e., the output load OL). In addition to a computer, which generally includes a central processing unit (CPU) in a base portion 118, a graphical user interface 122, and a plurality of user input devices 120, 124, the data acquisition/data processing device 104 may further comprise an analog-to-digital (A/D) converter if the signals $S_{ACO1}$-$S_{ACO8}$ are in the form of analog signals. In such a case, the analog-to-digital converter will convert the analog signals into digital signals for processing by a central processing unit (CPU).

When the data acquisition/data processing device 104 receives the voltage signals $S_{ACO1}$-$S_{ACO8}$, it transforms the signals into output forces and/or moments by multiplying the voltage signals $S_{ACO1}$-$S_{ACO8}$ by a calibration matrix. After which, the force $F_L$ exerted on the surface of the first force plate by the left foot of the subject, the force $F_R$ exerted on the surface of the second force plate by the right foot of the subject, and the center of pressure for each foot of the subject (i.e., the x and y coordinates of the point of application of the force applied to the measurement surface by each foot) are determined by the data acquisition/data processing device 104. The computations performed in the determination of the forces and center of pressure are described hereinafter.

While, in a preferred embodiment of the invention, the data acquisition/data processing device 104 determines the forces $F_L$, $F_R$ exerted on the surface of the first and second force plates by the feet of the subject and the center of pressure for each foot of the subject, it is to be understood that the invention is not so limited. Rather, in other embodiments of the invention, the output forces of the data acquisition/data processing device 104 could include all three (3) orthogonal components of the resultant forces acting on the two plate components 106, 108. In yet other embodiments of the invention, the output forces and moments of the data acquisition/data processing device 104 can be in the form of other forces and moments as well.

B. Second Embodiment

Figure 9:
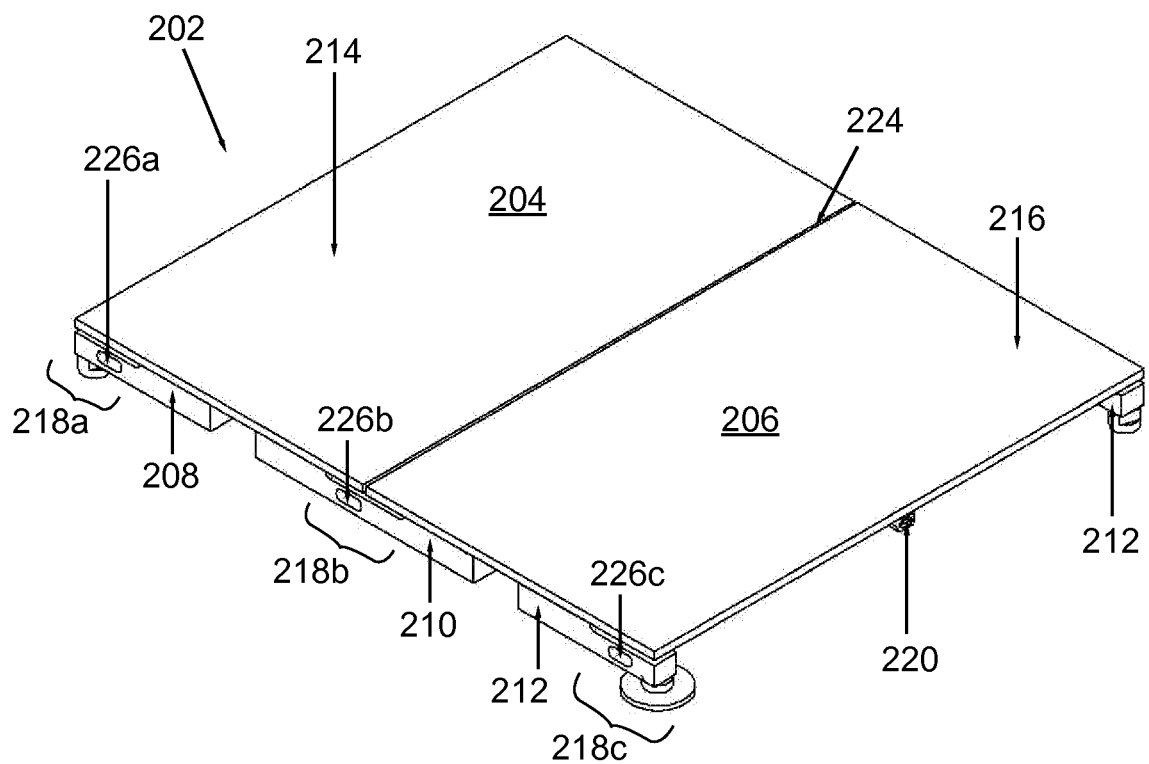
FIG. 9 is a perspective view of a dual force plate assembly of the dual force plate system according to a second embodiment of the invention.
Figure 10:
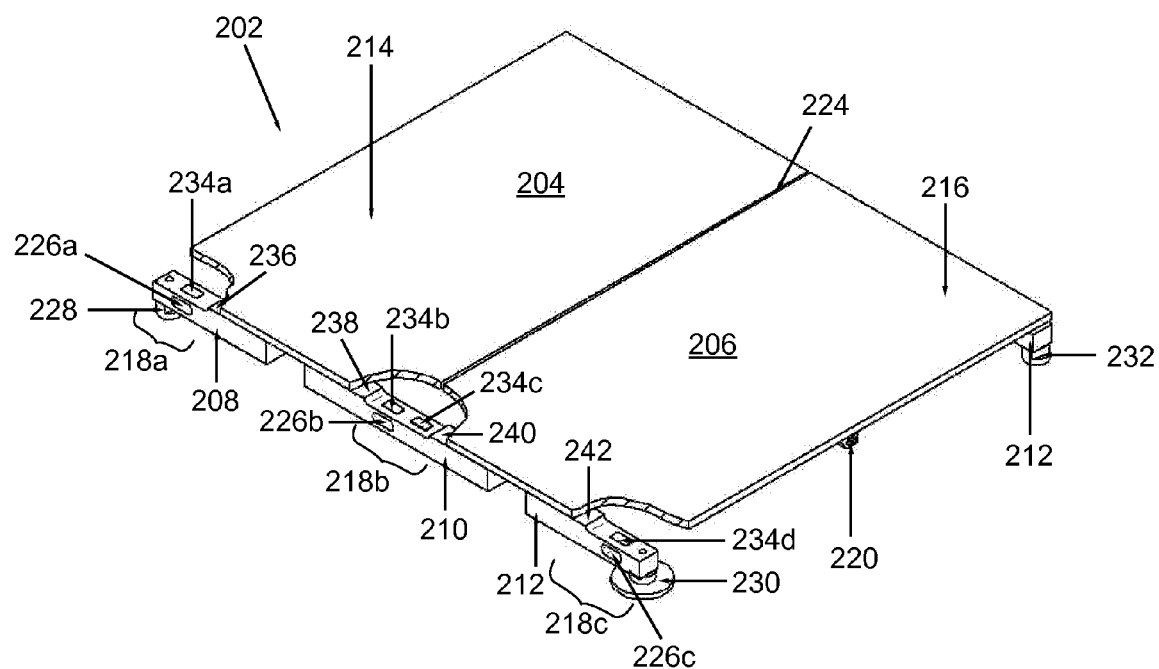
FIG. 10 is a cut-away perspective view of the dual force plate assembly of the dual force plate system according to the second embodiment of the invention.
Figure 11:
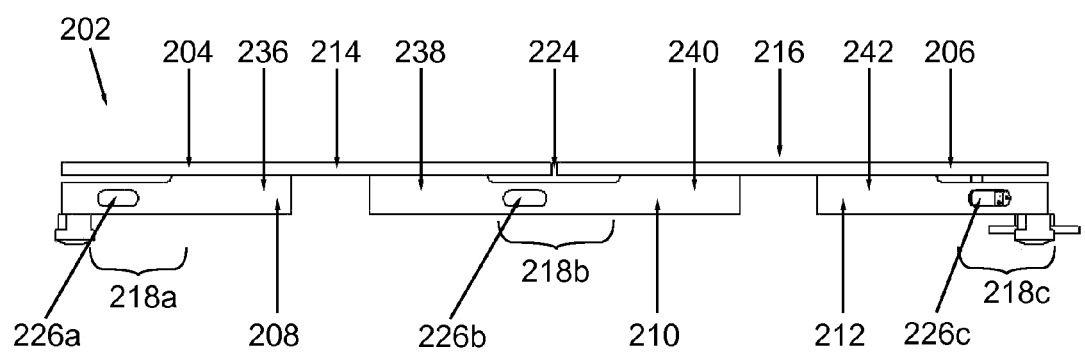
FIG. 11 is a side view of the dual force plate assembly of the dual force plate system according to the second embodiment of the invention.

A second embodiment of the dual force plate assembly is seen generally at 202 in FIG. 9, and in FIGS. 10 and 11. In accordance with the second embodiment of the invention, a dual force plate system generally comprises the dual force plate assembly 202 of FIG. 9 operatively coupled to a data acquisition/data processing device 104 by virtue of an electrical cable 126 (as illustrated in FIG. 1 for the dual force plate assembly 102). In the second embodiment, the dual force plate assembly 202 for receiving a subject utilizes a plurality of spaced apart, short transducer beams 208, 210, 212 disposed underneath, and near opposite lateral sides of, a first plate component 204 and a second plate component 206. Because the data acquisition/data processing device 104 and the electrical cable 126 are the same as that described above with regard to the first embodiment, a description of these components 104, 126 will not be repeated for this embodiment Like the dual force plate assembly 102 of the first embodiment, the dual force plate assembly 202 also includes a preamplifier board (not explicitly shown in FIG. 9) mounted to the underside of the second plate component 206. In addition, similar to the preceding embodiment, the preamplifier board is provided with a port 220 for receiving the end of the electrical cable 126 that operatively couples the force plate assembly 202 to the data acquisition/data processing device 104.

Advantageously, the use of three discrete transducer beams 208, 210, 212 on each side of the dual force plate assembly 202, rather than two continuous beams on each side thereof, reduces the overall amount of stock materials that are required in the fabrication of the plate assembly 202. This is particularly important for dual force plate assemblies that have a large footprint.

As illustrated in FIG. 9, the dual force plate assembly 202 according to the second embodiment of the invention includes a first plate component 204, a second plate component 206, and two sets of spaced apart, short transducer beams 208, 210, 212 disposed underneath, and near opposite lateral sides of, the first plate component 204 and second plate component 206. As depicted in FIG. 9, the first short transducer beam 208 is disposed in a first corner of the dual force plate assembly 202 and includes a first force transducer element 218a. The second short transducer beam 210 is connected to both the first plate component 204 and the second plate component 206 and comprises a second force transducer element 218b, while the third short transducer beam 212 is disposed in a second corner of the dual force plate assembly 202 and includes a third force transducer element 218c. As in the first embodiment, the first plate component 204 has a top surface 214 that is configured to receive a first portion of a body of a subject. Similarly, the second plate component 206 has a top surface 216 that is configured to receive a second portion of a body of a subject. Also, similar to the first embodiment described above, a narrow gap 224 is provided between the first plate component 204 and the second plate component 206 so as to prevent interaction between the two plate components 204, 206.

Because the short transducer beams 208, 210, 212 disposed underneath, and near opposite lateral sides of, the first plate component 204 and second plate component 206 are structurally identical to one another, only one set of force transducer beams 208, 210, 212 will be described with regard to the second embodiment. As depicted in FIGS. 10 and 11, each short transducer beam 208 has a top protruding portion 236 that is fixedly attached to the bottom surface of the first plate component 204. Similarly, each oppositely disposed, short transducer beam 212 has a top protruding portion 242 that is fixedly attached to the bottom surface of the second plate component 206. Each centrally disposed short transducer beam 210, each of which extends below the gap 224, comprises a first protruding portion 238 that is fixedly attached to the bottom surface of the first plate component 204 and a second protruding portion 240 that is fixedly attached to the bottom surface of the second plate component 206. Similar to the first embodiment described above, the short transducer beams 208, 210, 212 comprise respective transducer elements 218a, 218b, 218c (which are formed by respective longitudinal segments of the force transducer beams 208, 210, 212) and respective apertures 226a, 226b, 226c disposed therethrough. Also, as in the first embodiment, the outer transducer elements 218a, 218c measure the vertical shear forces exerted on the first and second plate components 204, 206, respectively, whereas the centrally disposed transducer elements 218b measure both the vertical shear force and bending moment resulting from a load being applied to the first and second plate components 204, 206. Alternatively, rather than measuring both the vertical shear force and bending moment, each centrally disposed transducer element 218b can measure a first bending moment at a first location along the length of the transducer element 218b and a second bending moment at a second location along the length of the transducer element 218b, the first location being spaced apart from the second location.

Like the force transducer element 112a described with regard to the first embodiment of the invention, the force transducer element 218a is provided with a plurality of strain gages 234a secured to the outer, top surface of the longitudinal segment of the force transducer beam 208 and substantially centered on the aperture 226a (see FIG. 10). Also, similar to the force transducer element 112c of the first embodiment, the force transducer element 218c is provided with a plurality of strain gages 234d secured to the outer, top surface of the longitudinal segment of the force transducer beam 212 and substantially centered on the aperture 226c. In addition, like the force transducer element 112b of the first embodiment of the invention, the force transducer element 218b is provided with a plurality of strain gages 234b secured to the outer, top surface of the longitudinal segment of the force transducer beam 210 and substantially centered on the aperture 226b, a first additional plurality of strain gages 234c mounted on the outer, top surface of the second transducer element 218b, horizontally spaced apart from the plurality of strain gages 234b, and a second additional plurality of strain gages (not shown) mounted on the outer, bottom surface of the second transducer element 218b, and substantially vertically aligned with the first additional plurality of strain gages 234c.

As explained above with regard to the first embodiment of the invention, it is highly advantageous that the first and second plate components 204, 206 only be connected to the protruding portions 236, 238, 240, 242 of the short force transducer beams 208, 210, 212 so as to ensure that the total load applied to the top surfaces 214, 216 of the plate components 204, 206 is only transmitted through the force transducer elements 218a, 218b, 218c of the force transducer beams 208, 210, 212.

In the second embodiment of the invention, each short force transducer beam 208, 212 is provided with a respective support foot disposed near an outer end thereof. In FIG. 10, it can be seen that the first of the two short force transducer beams 208 is provided with one non-adjustable support foot 228 near the outer end thereof, whereas the first of the two short force transducer beams 212 is provided with one adjustable support foot 230 near the outer end thereof. Also, as depicted in FIG. 10, the second of the two short transducer beams 212 is provided with a non-adjustable support foot 232, which is substantially the same as non-adjustable support foot 228. The second of the two force transducer beams 208 is not explicitly shown in FIG. 10, but it is provided with a non-adjustable support foot disposed near an outer end thereof, which is generally the same as non-adjustable support feet 228, 232. Like the dual force plate assembly 102 in the first embodiment of the invention, the dual force plate assembly 202 is designed to be installed on a floor of a building or on any other rigid surface. The adjustable support foot 230 facilitates the leveling of the dual force plate assembly 202 on an uneven surface.

C. Third Embodiment

Figure 12:
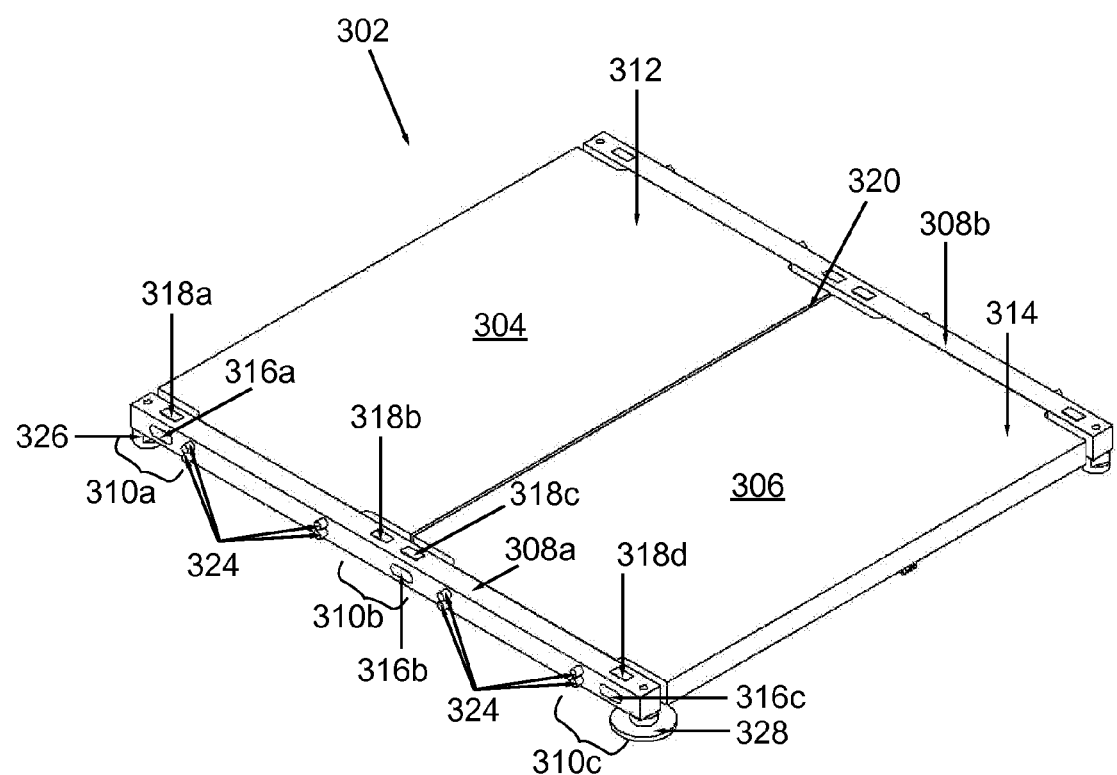
FIG. 12 is a perspective view of a dual force plate assembly of the dual force plate system according to a third embodiment of the invention.
Figure 13:
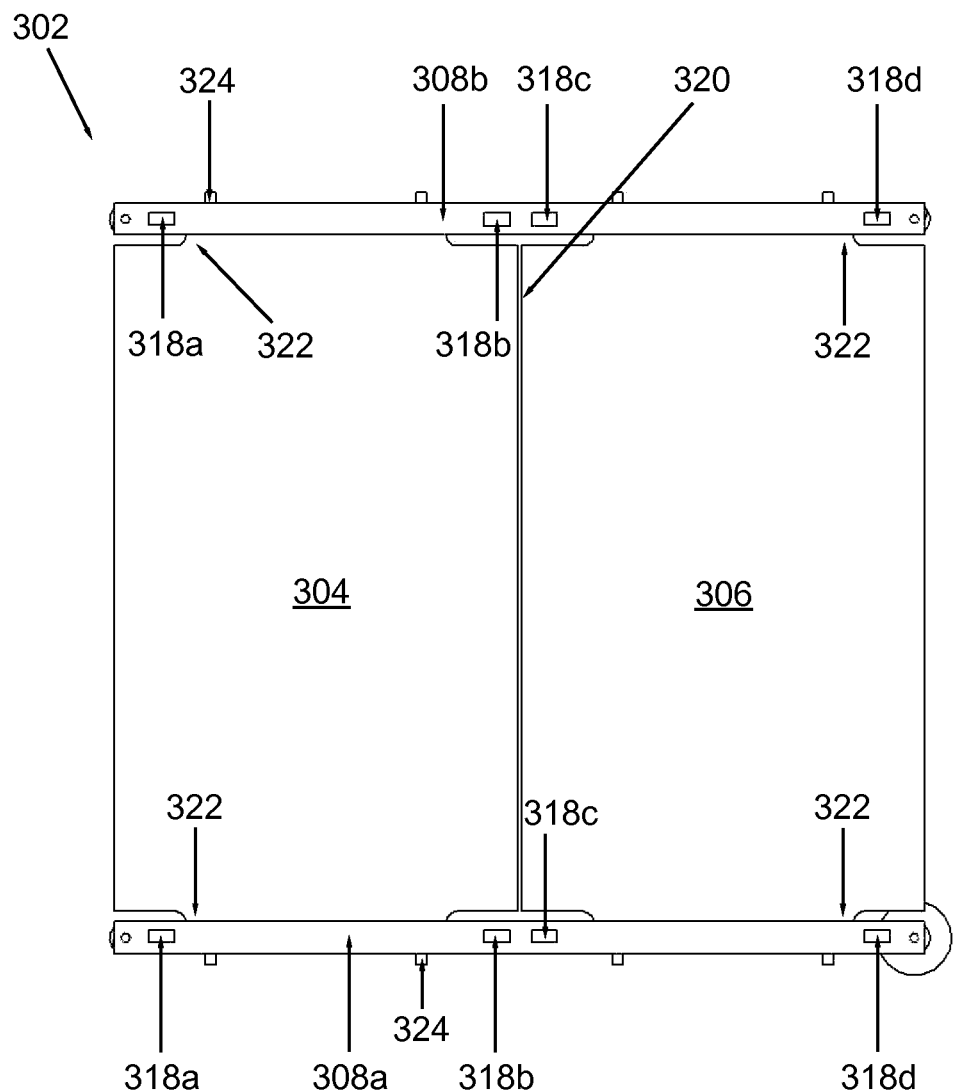
FIG. 13 is a top view of the dual force plate assembly of the dual force plate system according to the third embodiment of the invention.

A third embodiment of the dual force plate assembly is seen generally at 302 in FIGS. 12 and 13. In accordance with the third embodiment of the invention, the dual force plate assembly 302 for receiving a subject utilizes continuous force transducer beams 308a, 308b disposed on opposite lateral sides of the first and second plate components 304, 306, rather than force transducer beams disposed underneath the first and second plate components as described with regard to the first and second embodiments of the invention. As explained above in conjunction with the preceding two embodiments, the first plate component 304 has a top surface 312 that is configured to receive a first portion of a body of a subject. Similarly, the second plate component 306 has a top surface 314 that is configured to receive a second portion of a body of a subject. Also, similar to the first two embodiments described above, a continuous narrow gap 320 is provided between the first plate component 304 and the second plate component 306 so as to prevent interaction between the two plate components 304, 306.

Advantageously, in a preferred embodiment, the dual force plate assembly 302 has an overall height that is significantly lower than conventional force plates used in balance assessment. This reduction in height is made possible, in part, by the mounting of the continuous force transducer beams 308a, 308b on the lateral sides of the first and second plate components 304, 306.

Referring to FIG. 12, it can be seen that each continuous force transducer beam 308a, 308b includes a plurality of force transducer elements 310a, 310b, 310c disposed along the length thereof. Also, similar to the preceding two embodiments of the invention, each of the plurality of force transducer elements 310a, 310b, 310c is provided with a respective aperture 316a, 316b, 316c disposed therethrough. Moreover, as in the preceding embodiments, the outer transducer elements 310a, 310c measure the vertical shear forces exerted on the first and second plate components 304, 306, respectively, whereas the centrally disposed transducer elements 310b measure both the vertical shear force and bending moment resulting from a load being applied to the first and second plate components 304, 306. Alternatively, rather than measuring both the vertical shear force and bending moment, each centrally disposed transducer element 310b can measure a first bending moment at a first location along the length of the transducer element 310b and a second bending moment at a second location along the length of the transducer element 310b, the first location being spaced apart from the second location.

Like the force transducer elements 112a, 218a described with regard to the first two embodiments of the invention, each first force transducer element 310a is provided with a plurality of strain gages 318a secured to the outer, top surface of its associated force transducer beam 308a, 308b, and substantially centered on the aperture 316a (see FIG. 12). Also, similar to the force transducer elements 112c, 218c of the first two embodiments, each force transducer element 310c is provided with a plurality of strain gages 318d secured to the outer, top surface of its associated force transducer beam 308a, 308b, and substantially centered on the aperture 316c. In addition, like the force transducer elements 112b, 218b of the first two embodiments of the invention, each force transducer element 310b is provided with a plurality of strain gages 318c secured to the outer, top surface of its associated force transducer beam 308a, 308b and substantially centered on the aperture 316b, a first additional plurality of strain gages 318b mounted on the outer, top surface of the second transducer element 310b, horizontally spaced apart from the plurality of strain gages 318c, and a second additional plurality of strain gages (not shown) mounted on the outer, bottom surface of the second transducer element 310b, and substantially vertically aligned with the first additional plurality of strain gages 318b. In FIG. 12, it can be seen that the second force transducer element 310b extends across the gap 320 between the first plate component 304 and the second plate component 306 (i.e., the second force transducer element 310b bridges the gap 320 between the first plate component 304 and the second plate component 306).

Referring to FIGS. 12 and 13, it can be seen that each continuous force transducer beam 308a, 308b is fixedly attached to adjacent lateral sides of the first and second plate components 304, 306 using a plurality of screws 324. In particular, as best shown in the top view of FIG. 13, each force transducer beam 308a, 308b is attached to a respective centrally disposed protruding portion 322 on opposite lateral sides of the first plate component 304 and the second plate component 306. It is highly advantageous that the force transducer beams 308a, 308b only be connected to the centrally disposed protruding portions 322 of the first and second plate component 304, 306 so as to ensure that the total load applied to the top surfaces 312, 314 of the plate components 304, 306 is only transmitted through the force transducer elements 310a, 310b, 310c on each side thereof. In FIG. 12, a total of four (4) screws 324 are used to connect each force transducer beam 308a, 308b to each plate component 304, 306. However, it is to be understood that the invention is not so limited. Rather, in other embodiments of the invention, more than four screws or less than four screws could be used to fixedly attach each force transducer beam 308a, 308b to each force plate component 304, 306. In yet other embodiments of the invention, the force transducer beams 308a, 308b could be connected to plate components 304, 306 by using different types of suitable adhesives (e.g., an adhesive designed for bonding metallic components to one another).

As best depicted in FIG. 12, the top surface 312 of the first plate component 304 and the top surface 314 of the second plate component 306 are both substantially aligned with the top surfaces of the transducer beams 308a, 308b (i.e., they are substantially flush with the top surfaces of the transducer beams 308a, 308b) in a preferred embodiment of the invention. This design feature enables the profile of the dual force plate assembly 302 to be minimized so that subjects are able to easily step on and off the dual force plate assembly 302. Also, it prevents the transducer beams 308a, 308b from posing a tripping hazard to subjects, as would be the case if the top surfaces of the transducer beams 308a, 308b were disposed above the top surfaces 312, 314 of the first and second plate components 304, 306. However, it is to be understood that the invention is not so limited. For example, in other embodiments of the invention, the top surfaces of the transducer beams 308a, 308b could be disposed below the top surfaces 312, 314 of the first and second plate components 304, 306.

In the third embodiment of the invention, each force transducer beam 308a, 308b is provided with respective support feet disposed at opposed longitudinal ends thereof. In FIG. 12, it can be seen that the first of the two transducer beams 308a is provided with one non-adjustable support foot 326 near a first longitudinal end thereof and one adjustable support foot 328 near the other longitudinal end thereof. The bottom portion of the second of the two force transducer beams 308b is not explicitly shown in FIG. 12, but it is provided with two (2) non-adjustable support feet disposed at opposed longitudinal ends thereof, both of which are generally the same as non-adjustable support foot 326. The dual force plate assembly 302 is designed to be installed on a floor of a building or on any other rigid surface. The adjustable support foot 328 facilitates the leveling of the dual force plate assembly 302 on an uneven surface.

D. Fourth Embodiment

Figure 14:
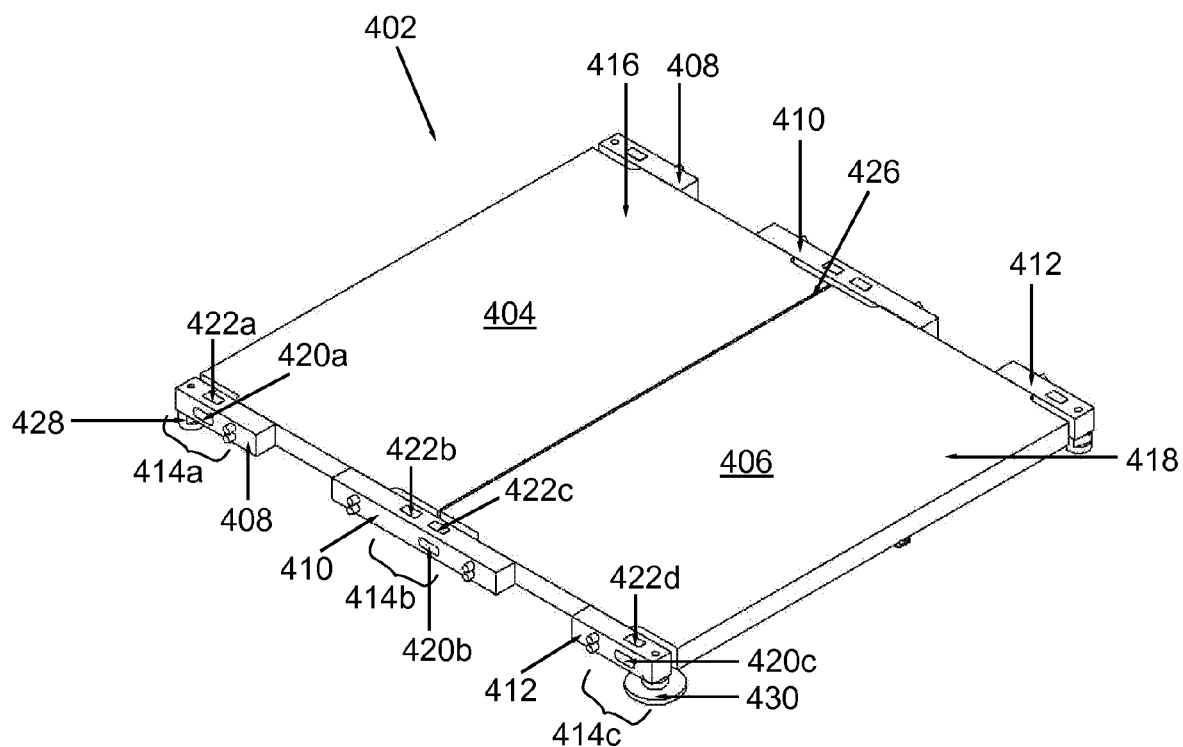
FIG. 14 is a perspective view of a dual force plate assembly of the dual force plate system according to a fourth embodiment of the invention.
Figure 15:
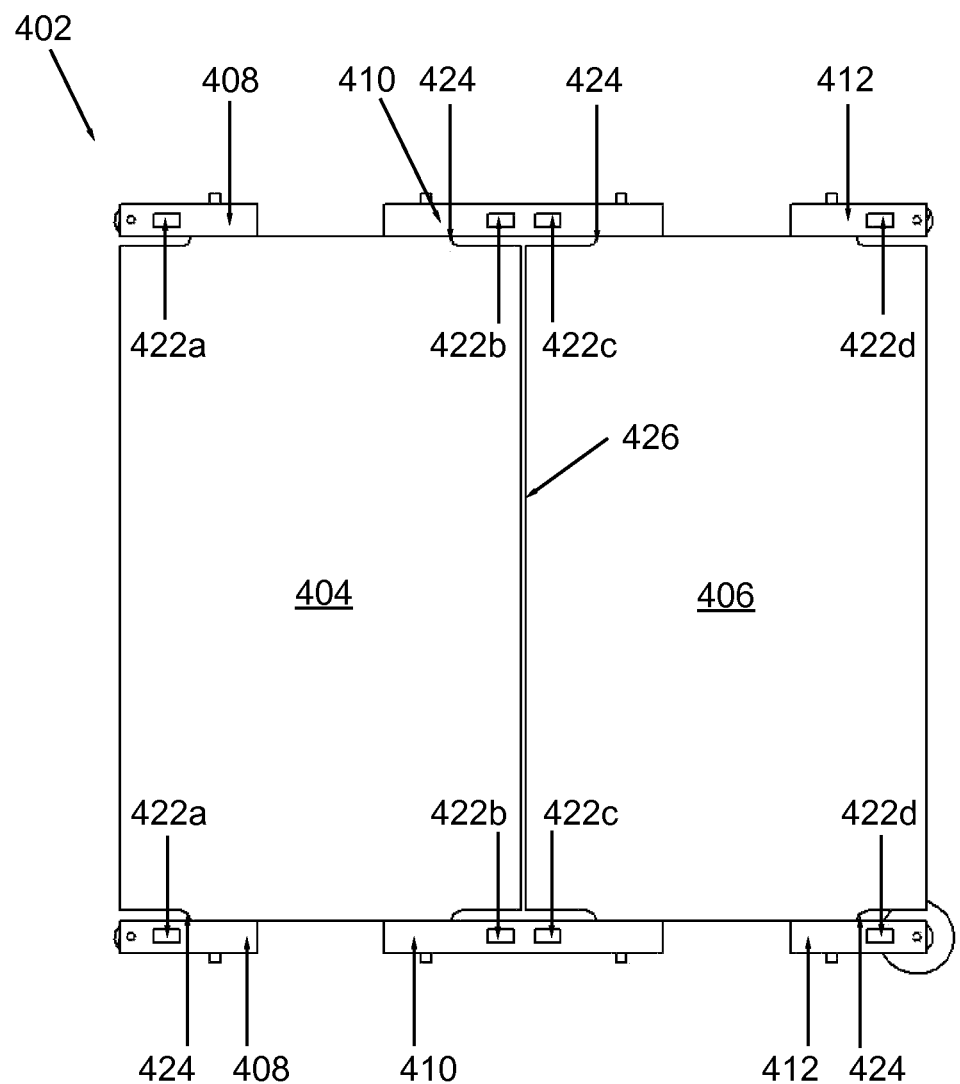
FIG. 15 is a top view of the dual force plate assembly of the dual force plate system according to the fourth embodiment of the invention.

A fourth embodiment of the dual force plate assembly is seen generally at 402 in FIGS. 14 and 15. In accordance with the fourth embodiment of the invention, the dual force plate assembly 402 for receiving a subject utilizes two sets of spaced apart, short transducer beams 408, 410, 412 disposed on opposite lateral sides of first and second plate components 404, 406, rather than the continuous transducer beams 308a, 308b described with respect to the third embodiment of the invention. As explained above in conjunction with the preceding three embodiments, the first plate component 404 has a top surface 416 that is configured to receive a first portion of a body of a subject. Similarly, the second plate component 406 has a top surface 418 that is configured to receive a second portion of a body of a subject. Also, similar to the first three embodiments described above, a continuous narrow gap 426 is provided between the first plate component 404 and the second plate component 406 so as to prevent interaction between the two plate components 404, 406. Similar to the preceding embodiments described above, the short transducer beams 408, 410, 412 comprise respective transducer elements 414a, 414b, 414c (which are formed by respective longitudinal segments of the force transducer beams 408, 410, 412) and respective apertures 420a, 420b, 420c disposed therethrough. Also, as in the preceding embodiments, the outer transducer elements 414a, 414c measure the vertical shear forces exerted on the first and second plate components 404, 406, respectively, whereas the centrally disposed transducer elements 414b measure both the vertical shear force and bending moment resulting from a load being applied to the first and second plate components 404, 406. Alternatively, rather than measuring both the vertical shear force and bending moment, each centrally disposed transducer element 414b can measure a first bending moment at a first location along the length of the transducer element 414b and a second bending moment at a second location along the length of the transducer element 414b, the first location being spaced apart from the second location.

Like the force transducer elements 112a, 218a, 310a described with regard to the first three embodiments of the invention, the first force transducer element 414a is provided with a plurality of strain gages 422a secured to the outer, top surface of the force transducer beam 408 and substantially centered on the aperture 420a (see FIG. 14). Also, similar to the force transducer elements 112c, 218c, 310c of the first three embodiments, the force transducer element 414c is provided with a plurality of strain gages 422d secured to the outer, top surface of the force transducer beam 412 and substantially centered on the aperture 420c. In addition, like the force transducer elements 112b, 218b, 310b of the first three embodiments of the invention, the force transducer element 414b is provided with a plurality of strain gages 422c secured to the outer, top surface of the force transducer beam 410 and substantially centered on the aperture 420b, a first additional plurality of strain gages 422b mounted on the outer, top surface of the second transducer element 414b, horizontally spaced apart from the plurality of strain gages 422c, and a second additional plurality of strain gages (not shown) mounted on the outer, bottom surface of the second transducer element 414b, and substantially vertically aligned with the first additional plurality of strain gages 422b.

Now, referring to FIGS. 14 and 15, it can be seen that each first short transducer beam 408 is fixedly attached to the outer end portion of a respective centrally disposed protruding portion 424 on opposite lateral sides of the first plate component 404. Similarly, each third short transducer beam 412 is fixedly attached to the outer end portion of a respective centrally disposed protruding portion 424 on opposite lateral sides of the second plate component 406. Also, as depicted in FIGS. 14 and 15, each second short transducer beam 410 is fixedly attached to both the inner end portion of a respective centrally disposed protruding portion 424 on a lateral side of the first plate component 404 and the inner end portion of a respective centrally disposed protruding portion 424 on an adjacent lateral side of the second plate component 406. As described above with regard to the third embodiment, it is highly advantageous that the spaced apart, short transducer beams 408, 410, 412 only be connected to the first and second plate components 404, 406 by means of the centrally disposed protruding portions 424 so as to ensure that the total load applied to the top surfaces 416, 418 of the plate components 404, 406 is only transmitted through the force transducer elements 414a, 414b, 414c.

In the fourth embodiment of the invention, each short force transducer beam 408, 412 is provided with a respective support foot disposed near an outer end thereof. In FIG. 14, it can be seen that the first of the two short force transducer beams 408 is provided with one non-adjustable support foot 428 near the outer end thereof, whereas the first of the two short force transducer beams 412 is provided with one adjustable support foot 430 near the outer end thereof. Also, while not explicitly shown in FIG. 14, the second of the two short force transducer beams 408 is provided with a non-adjustable support foot near an outer end thereof, which is substantially the same as non-adjustable support foot 428. Also, referring to FIG. 14, the second of the two short force transducer beams 412 is provided with a non-adjustable support foot near an outer end thereof, which is generally equivalent to non-adjustable support foot 428. Like the dual force plate assemblies described in the preceding embodiments of the invention, the dual force plate assembly 402 is designed to be installed on a floor of a building or on any other rigid surface. The adjustable support foot 430 facilitates the leveling of the dual force plate assembly 402 on an uneven surface.

E. Fifth Embodiment

Figure 16:
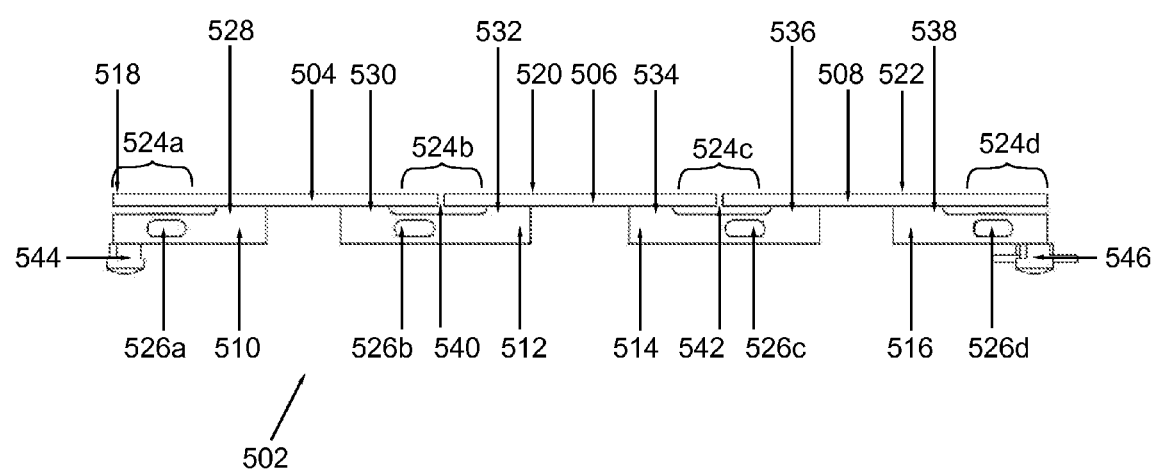
FIG. 16 is a side view of a triple force plate assembly of a triple force plate system according to a fifth embodiment of the invention.

A fifth embodiment of the dual force plate assembly is seen generally at 502 in FIG. 16. In accordance with the fifth embodiment of the invention, the dual force plate assembly 502 for receiving a subject utilizes three plate components 504, 506, 508, rather than two plate components as employed in the previous embodiments of the invention. Two sets of spaced apart, short transducer beams 510, 512, 514, 516 are disposed underneath, and near opposite sides of, the first, second, and third plate components 504, 506, 508. As depicted in FIG. 16, each short transducer beam 510 has a top protruding portion 528 that is fixedly attached to the bottom surface of the first plate component 504. Similarly, each oppositely disposed, short transducer beam 516 has a top protruding portion 538 that is fixedly attached to the bottom surface of the third plate component 508. Each short transducer beam 512, which extends below a continuous gap 540 between the first and second plate components 504, 506, comprises a first protruding portion 530 that is fixedly attached to the bottom surface of the first plate component 504 and a second protruding portion 532 that is fixedly attached to the bottom surface of the second plate component 506. Similarly, each short transducer beam 514, which extends below a continuous gap 542 between the second and third plate components 506, 508, comprises a first protruding portion 534 that is fixedly attached to the bottom surface of the second plate component 506 and a second protruding portion 536 that is fixedly attached to the bottom surface of the third plate component 508. Like the preceding embodiments described above, the short transducer beams 510, 512, 514, 516 comprise respective transducer elements 524a, 524b, 524c, 524d and respective apertures 526a, 526b, 526c, 526d disposed therethrough. Also, similar to that described with regard to the preceding embodiments, the outer transducer elements 524a, 524d measure the vertical shear forces exerted on the first and third plate components 504, 508, respectively, whereas the centrally disposed transducer elements 524b measure both the vertical shear force and bending moment resulting from a load being applied to the first and second plate components 504, 506 and the centrally disposed transducer elements 524c measure both the vertical shear force and bending moment resulting from a load being applied to the second and third plate components 506, 508. Alternatively, rather than measuring both the vertical shear force and bending moment, each centrally disposed transducer element 524b, 524c can measure a first bending moment at a first location along the length of the transducer element 524b, 524c and a second bending moment at a second location along the length of the transducer element 524b, 524c, the first location being spaced apart from the second location.

As explained above with regard to the preceding embodiments of the invention, it is highly advantageous that the first, second, and third plate components 504, 506, 508 only be connected to the protruding portions 528, 530, 532, 534, 536, 538 of the short force transducer beams 510, 512, 514, 516 so as to ensure that the total load applied to the top surfaces 518, 520, 522 of the plate components 504, 506, 508 is only transmitted through the force transducer elements 524a, 524b, 525c, 524d of the force transducer beams 510, 512, 514, 516.

In the fifth embodiment of the invention, each short force transducer beam 510 is provided with a non-adjustable support foot 544 near the outer longitudinal end thereof. One of the two short force transducer beams 516 is also provided with a non-adjustable support foot 544 near the outer longitudinal end thereof (not visible in FIG. 16), whereas the other of the two short force transducer beams 516 is provided with an adjustable support foot 546 to permit the leveling of the dual force plate assembly 502 on an uneven surface.

F. Computations Performed by the Data Acquisition/Data Processing Device 104

Now, the manner in which the data acquisition/data processing device 104 calculates the applied forces and the center of pressure for each of the subject's two feet will be described in detail. The center of pressure for each foot of the subject comprises the x and y coordinates of the point of application of the force applied to the measurement surface by that foot. During the balance assessment of a patient, the variation in the center of pressure (i.e., the sway of the patient) is monitored so as to determine the overall stability of that patient. Initially, referring to FIGS. 17A-17D, the mathematical determination of the x-coordinates for each foot of the subject will be explained. Then, with reference to FIG. 18, the determination of the y-coordinates for each foot of the subject will be described.

Figures 17A, 17B, 17C, 17D:
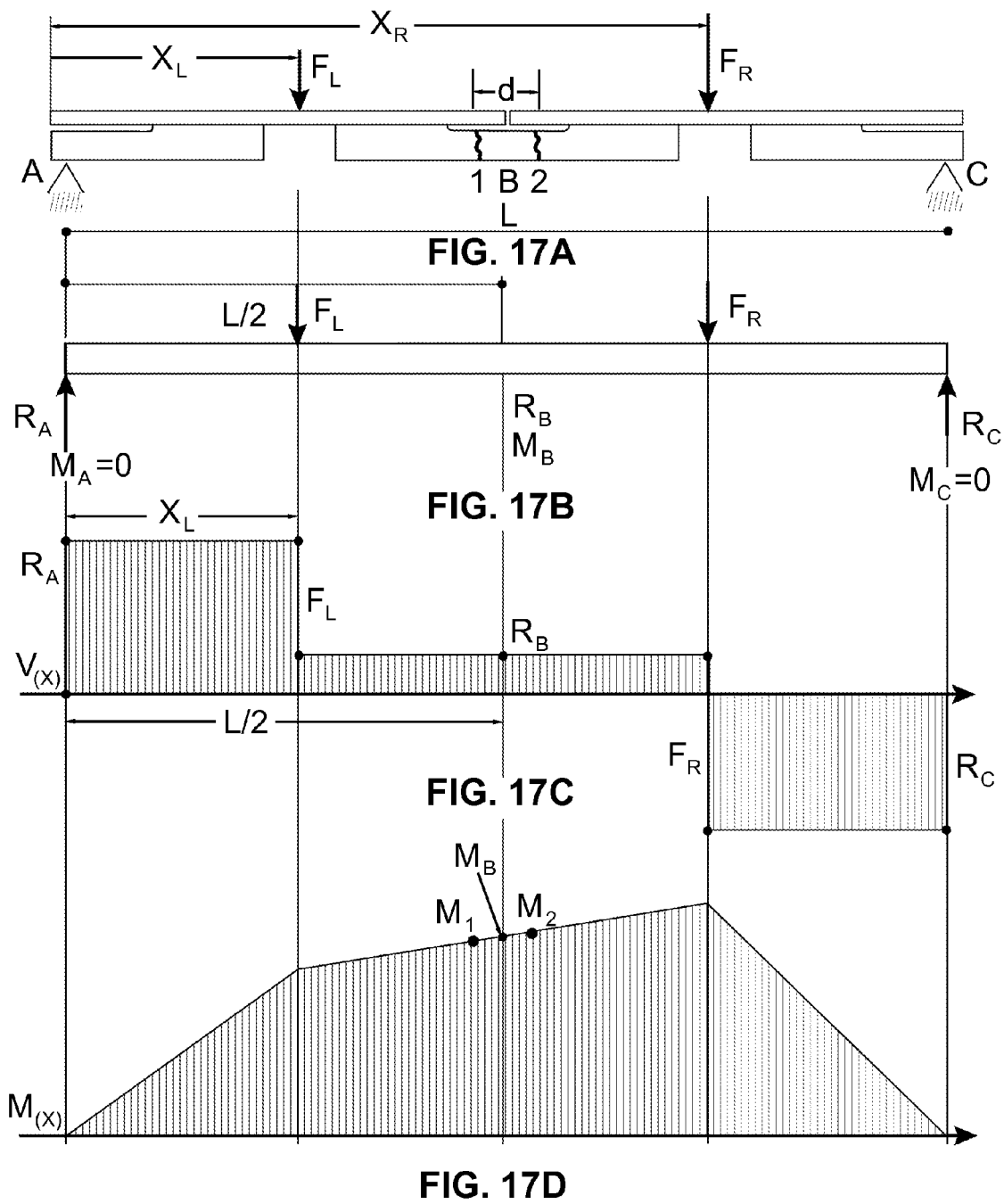
FIG. 17A is a side view of a dual force plate assembly of a dual force plate system according to an exemplary embodiment of the invention with exemplary applied forces depicted thereon so as to illustrate the manner in which the x-coordinates of the center-of-pressure are determined.
FIG. 17B is a free body diagram that diagrammatically represents the forces and moments acting on the dual force plate assembly according to an exemplary embodiment of the invention.
FIG. 17C is a shear diagram that diagrammatically represents the shear forces acting on the dual force plate assembly according to an exemplary embodiment of the invention.
FIG. 17D is a moment diagram that diagrammatically represents the moments acting on the dual force plate assembly according to an exemplary embodiment of the invention.

FIG. 17A depicts a side view of a dual force plate assembly of a dual force plate system, wherein the unknown parameters to be determined are diagrammatically depicted thereon. The first set of unknown parameters comprises: (i) the force $F_L$ applied to the first measurement surface of the first force plate by the left foot of the subject, and (ii) the force $F_R$ applied to the second measurement surface of the second force plate by the right foot of the subject. The second set of unknown parameters comprises: (i) the distance $x_L$ measured from a reference point at the outer edge of the first force plate to the point of application of the force $F_L$ exerted on the first measurement surface by the left foot of the subject, and (ii) the distance $x_R$ measured from a reference point at the outer edge of the first force plate to the point of application of the force $F_R$ exerted on the second measurement surface by the right foot of the subject (i.e., the x-coordinates of the center of pressure for each foot of the subject). Thus, initially there are a total of four unknown parameters that need to be determined.

In FIG. 17A, the dual force plate assembly is diagrammatically depicted as being supported on simple supports, which are otherwise known as knife-edge supports. This model is appropriate for the typical arrangement of the dual force plate assembly in which the feet of the assembly are simply resting on the surface of the floor, and thus, there is no moment reaction at the supports. However, it is to be understood that the invention is not so limited. Rather, in other embodiments of the invention, the feet of the dual force plate assembly are fixedly attached to the floor, and therefore, the connections between the force plate assembly and the floor are capable of transmitting moments. The mathematical analysis for such an arrangement would be similar to that provided below except that non-zero moments would be present at each support.

In FIG. 17B, a free diagram body of the dual force plate assembly is shown in order to graphically illustrate measured parameters of the system. Referring to this figure, it can be seen that the dual force plate assembly is being modeled as one continuous, simply supported beam. The dual force plate assembly can be accurately modeled as a single beam because the center transducer beams, each of which operatively connects the first plate to the second plate, are fixedly attached to the bottom surfaces of the first and second plates. Thus, even though separate components are utilized in the actual assembly, the dual force plate operates as if it is a single structure. As depicted in FIG. 17B, the shear force $R_A$ acting on the left end of the assembly is sensed by a first force transducer element, while the shear force $R_C$ acting on the right end of the assembly is measured by a second force transducer element. The third force transducer element, which is disposed on the center transducer beam, measures both the shear force $R_B$ and the moment $M_B$ (i.e., it measures the load transferred between the first and second plates).

Now that both the unknown parameters and the measured parameters of the dual force plate system have been defined, the mathematical equations for determining the unknown parameters of the system can be formulated. The forces exerted on the first and second force plates by the respective left and right feet of the subject are described by the following two equations:

$$F_L = R_A - R_B \quad (1)$$

$$F_R = R_B + R_C \quad (2)$$

where:

$F_L$: force exerted on the surface of the first force plate by the left foot of the subject;

$F_R$: force exerted on the surface of the second force plate by the right foot of the subject;
$R_A$: vertical force measured by the first force transducer element;
$R_B$: vertical force measured by the third force transducer element (i.e. between the two plates); and
$R_C$: vertical force measured by the second force transducer element.

Thus, applied forces can be obtained by plugging the shear forces $R_A$, $R_B$, and $R_C$, which are measured by the force transducer elements, into equations (1) and (2) and then, solving for forces $F_L$ and $F_R$.

Alternatively, if each centrally disposed transducer element measures a first and second bending moment $M_1$, $M_2$, rather than the shear force and a single bending moment, then the shear force $R_B$ can be determined by utilizing the following equation:

$$R_B = \frac{(M_2 - M_1)}{d} \qquad (3)$$

where:
$M_1$: first bending moment measured at a first location along the length of the third transducer element (e.g., see FIG. 17A, centrally located transducer beam);
$M_2$: second bending moment measured at a second location along the length of the third transducer element (e.g., see FIG. 17A, centrally located transducer beam); and
d: distance between the first location and the second location along the length of the third transducer element (e.g., see FIG. 17A, centrally located transducer beam).

Then, the applied forces $F_L$, $F_R$ can be determined from equations (1) and (2) by using the computed shear force $R_B$ together with the measured shear forces $R_A$ and $R_C$.

Next, turning to the shear diagram depicted in FIG. 17C, the moment $M_B$ is equal to the area under the shear force curves as follows:

$$M_B = \left(R_B \cdot \left(\frac{L}{2}\right)\right) + (F_L \cdot x_L) \qquad (4)$$

where:
$M_B$ moment about point B;
$R_B$: shear force measured by the third force transducer element (i.e. between the two plates) or computed;
L: overall length of the dual force plate assembly (i.e., combined length of the first and second force plates);
$F_L$: force exerted on the surface of the first force plate by the left foot of the subject; and
$x_L$: distance measured from a reference point at the outer edge of the first force plate to the point of application of the force $F_L$ exerted on the first measurement surface by the left foot of the subject;

The moment $M_B$ is graphically depicted in the moment diagram of FIG. 17D. Then, in order to solve for the desired unknown quantity, the terms of equation (4) are rearranged as follows:

$$x_L = \frac{M_B - \left(R_B \cdot \left(\frac{L}{2}\right)\right)}{F_L} \qquad (5)$$

Similarly, the unknown coordinate $x_R$ can be determined from the following moment balance equation, wherein the moments are summed about point A in a clockwise direction:

$$(x_L \cdot F_L) + (x_R \cdot F_R) - (L \cdot R_C) = 0 \qquad (6)$$

where:
$x_R$: distance measured from a reference point at the outer edge of the first force plate to the point of application of the force $F_R$ exerted on the second measurement surface by the right foot of the subject.

Then, in order to solve for the desired unknown quantity $x_R$, the terms of equation (6) are rearranged as follows:

$$x_R = \frac{(L \cdot R_C) - (x_L \cdot F_L)}{F_R} \qquad (7)$$

Figure 18:
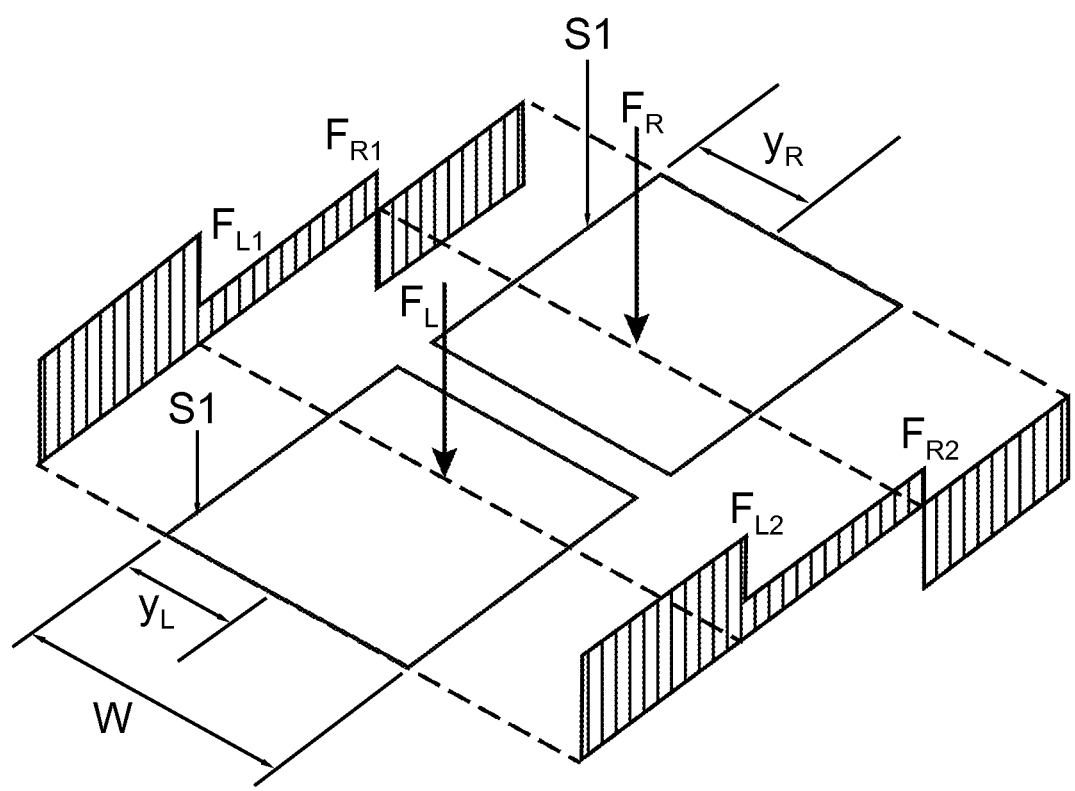
FIG. 18 is a three-dimensional (3-D) free body diagram/shear diagram that diagrammatically represents the forces acting on the dual force plate assembly according to an exemplary embodiment of the invention so as to illustrate the manner in which the y-coordinates of the center-of-pressure are determined.

Once the forces $F_L$ and $F_R$ and the x-coordinates of the center of pressure for each foot of the subject have been determined in the manner delineated above, a computational method that can be carried out by the data acquisition/data processing device 104 to compute the y-coordinates of the center of pressure for each foot of the subject will be explained with reference to the three-dimensional (3-D) free body diagram/shear diagram of FIG. 18. When broken down into their constituent components, the forces exerted on the first and second force plates by the respective left and right feet of the subject are described by the following two equations:

$$F_L = F_{L1} + F_{L2} \qquad (8)$$

$$F_R = R_{R1} + R_{R2} \qquad (9)$$

where:
$F_L$: force exerted on the surface of the first force plate by the left foot of the subject;
$F_{L1}$: first constituent component of the force exerted on the surface of the first force plate by the left foot of the subject;
$F_{L2}$: second constituent component of the force exerted on the surface of the first force plate by the left foot of the subject;
$F_R$: force exerted on the surface of the second force plate by the right foot of the subject;
$F_{R1}$: first constituent component of the force exerted on the surface of the second force plate by the right foot of the subject; and
$F_{R2}$: second constituent component of the force exerted on the surface of the second force plate by the right foot of the subject.

Then, the unknown coordinate $y_L$ can be determined from the following moment balance equation, wherein the moments are summed about a point on a first side S1 of the first force plate in a clockwise direction:

$$(F_L \cdot y_L) - (F_{L2} \cdot W) = 0 \qquad (10)$$

where:
$y_L$: distance measured from a reference point on the first side S1 of the first force plate to the point of application of the force $F_L$ exerted on the measurement surface by the left foot of the subject; and
W: width of the dual force plate assembly.

Next, in order to solve for the desired unknown quantity $y_L$, the terms of equation (10) are rearranged as follows:

$$y_L = W \cdot \left(\frac{F_{L2}}{F_L}\right) \quad (11)$$

Following a similar procedure, the last unknown parameter $y_R$ can be determined from the following moment balance equation, wherein the moments are summed about a point on a first side S1 of the second force plate in a clockwise direction:

$$(F_R \cdot y_R) - (F_{R2} \cdot W) = 0 \quad (12)$$

where:
$y_R$: distance measured from a reference point on the first side S1 of the second force plate to the point of application of the force $F_R$ exerted on the second measurement surface by the right foot of the subject.

Next, in order to solve for the desired unknown quantity $y_R$, the terms of equation (12) are rearranged as follows:

$$y_R = W \cdot \left(\frac{F_{R2}}{F_R}\right) \quad (13)$$

Therefore, all of the unknown parameters of the dual force plate system are mathematically determined in the manner explained above by the data acquisition/data processing device 104. In a preferred embodiment of the invention, the data acquisition/data processing device 104 is specially programmed to perform all of these above described calculations.

G. Sixth Embodiment

Figure 19:
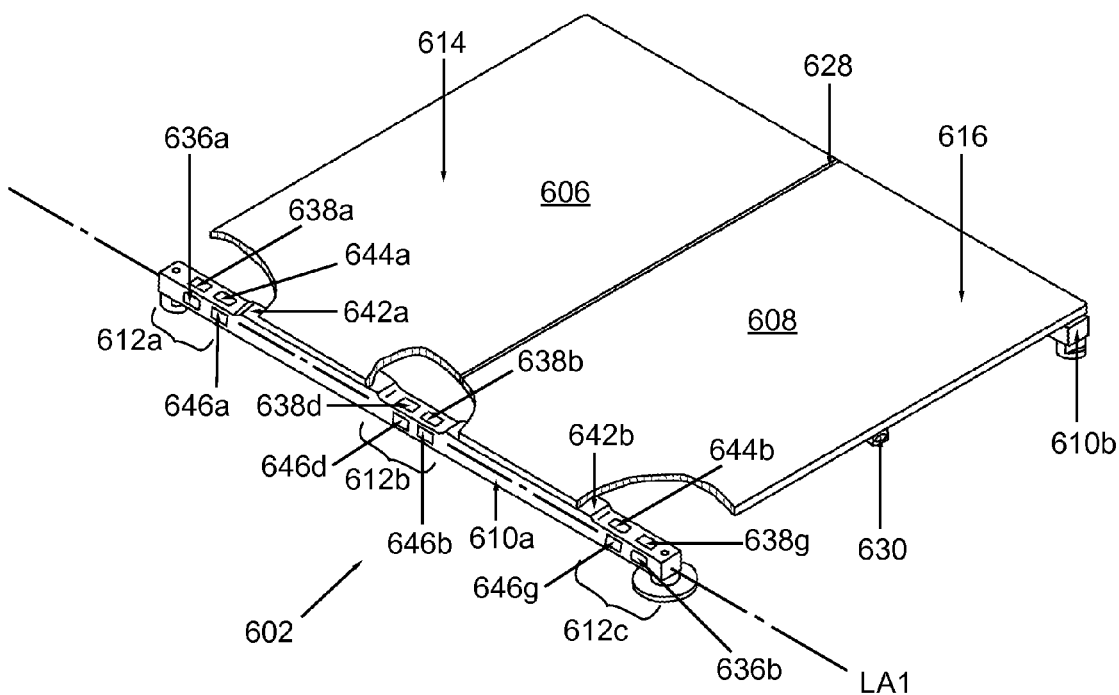
FIG. 19 is a cut-away perspective view of the dual force plate assembly of the dual force plate system according to a sixth embodiment of the invention.
Figure 20:
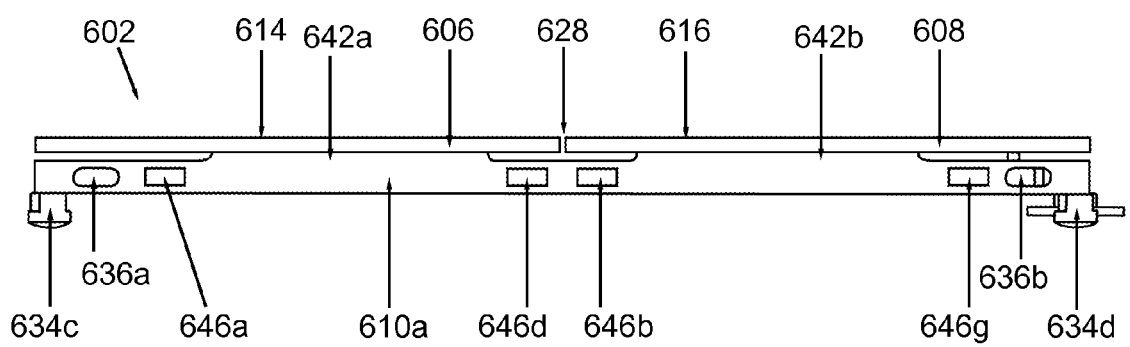
FIG. 20 is a side view of the dual force plate assembly of the dual force plate system according to the sixth embodiment of the invention.
Figure 21:
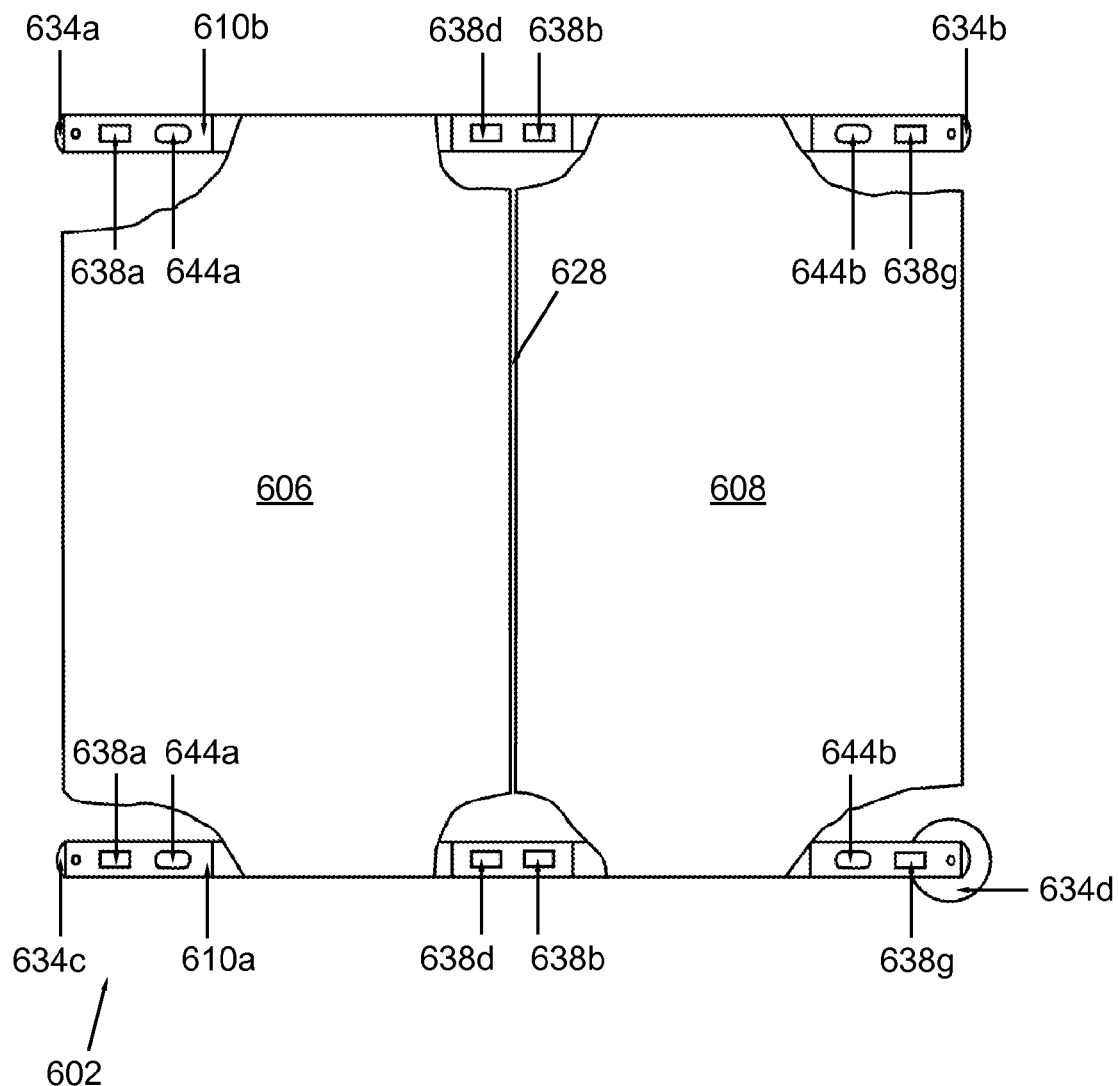
FIG. 21 is a cut-away top view of the dual force plate assembly of the dual force plate system according to the sixth embodiment of the invention.

A sixth embodiment of the dual force plate assembly is seen generally at 602 in FIGS. 19-21. In accordance with the sixth embodiment of the invention, the dual force plate assembly 602 for receiving a subject includes a first plate component 606, a second plate component 608, and continuous force transducer beams 610a, 610b mounted on opposite lateral sides of the first plate component 606 and second plate component 608. Unlike the force transducer beams described in conjunction with the aforedescribed embodiments of the invention, the force transducer beams 610a, 610b are capable of measuring the vertical force components and moments, as well as shear force components and moments. As explained above in conjunction with the preceding embodiments, the first plate component 606 has a top surface 614 that is configured to receive a first portion of a body of a subject. Similarly, the second plate component 608 has a top surface 616 that is configured to receive a second portion of a body of a subject. Also, similar to the embodiments described above, a narrow gap 628 is provided between the first plate component 606 and the second plate component 608 so as to prevent interaction between the two plate components 606, 608. Similar to the preceding embodiments, the dual force plate assembly 602 contains a port 630 for receiving the electrical cable 126.

Referring to FIGS. 19-21, it can be seen that each continuous force transducer beam 610a, 610b is attached to the underside of the first and second plate components 606, 608. In particular, as best shown in FIGS. 19 and 20, it can be seen that the top surface of each continuous force transducer beam 610a, 610b is provided with two protruding portions 642a, 642b. The protruding portions 642a, 642b are spaced apart from one another along the length of each continuous force transducer beam 610a, 610b. The top surface of the first protruding portion 642a on each of the continuous force transducer beams 610a, 610b is fixedly attached to the bottom surface of the first plate component 606, whereas the top surface of the second protruding portion 642b on each of the continuous force transducer beams 610a, 610b is fixedly attached to the bottom surface of the second plate component 608. It is highly advantageous that the first and second plate components 606, 608 only be connected to the protruding portions 642a, 642b of the continuous force transducer beams 610a, 610b so as to ensure that the total load applied to the top surfaces 614, 616 of the plate components 606, 608 is only transmitted through the force transducer components 612a, 612b, 612c. As explained above, each force transducer beam 610a, 610b can be fixedly attached to each plate component 606, 608 by utilizing a plurality of different attachment means such as, but not limited to, threaded fasteners (e.g., screws) or different types of suitable adhesives (e.g., an adhesive designed for bonding metallic components to one another).

As best illustrated in FIGS. 20 and 21, each force transducer beam 610a, 610b is provided with respective support feet 634c, 634d and 634a, 634b disposed at opposed longitudinal ends thereof. In the illustrated embodiment, the first of the two transducer beams 610a is provided with one non-adjustable support foot 634c near a first longitudinal end thereof and one adjustable support foot 634d near the other longitudinal end thereof, while the second of the two force transducer beams 610b is provided with two (2) non-adjustable support feet 634a, 634b disposed at opposed longitudinal ends thereof. The dual force plate assembly 602 is designed to be installed on a floor of a building or on any other rigid surface. The adjustable support foot 634d facilitates the leveling of the dual force plate assembly 602 on an uneven surface.

In the cut-away perspective view illustrated in FIG. 19, it can be seen that the first of the two transducer beams 610a is provided with three force transducer components 612a, 612b, 612c disposed along the length thereof. As shown in this figure, each of these three force transducer components 612a, 612b, 612c is linearly arranged along a longitudinal axis LA1, and each of these three force transducer components 612a, 612b, 612c intersects the longitudinal axis LA1. The first transducer component 612a is disposed at a first longitudinal end of the first transducer beam 610a. In the illustrated embodiment of the invention, the first transducer component 612a comprises a longitudinal segment of the force transducer beam 610a, a first aperture 636a disposed generally transversely through the longitudinal segment of the force transducer beam 610a, a second aperture 644a disposed generally vertically through the longitudinal segment of the force transducer beam 610a, a first plurality of strain gages 638a secured to the outer, top surface of the longitudinal segment of the force transducer beam 610a and substantially centered on the aperture 636a, and a second plurality of strain gages 646a secured to the outer, side surface of the longitudinal segment of the force transducer beam 610a and substantially centered on the aperture 644a. The first plurality of strain gages 638a together with the longitudinal segment of the force transducer beam 610a containing the first aperture 636a forms the vertical force transducer element of the first transducer component 612a, while the second plurality of strain gages 646a together with the longitudinal segment of the force transducer beam 610a containing the second aperture 644a forms the shear force transducer element of the first transducer component 612a.

The outer, top surface of the first transducer component 612a on which the first plurality of strain gages 638a is disposed is generally opposite to the inner top surface of the aperture 636a, while the outer, side surface of the first transducer component 612a on which the second plurality of strain gages 646a is disposed is generally opposite to the inner side surface of the aperture 644a. When a load is applied to the first plate component 606, the load is transferred to the longitudinal segment of the force transducer beam 610a that is associated with the first transducer component 612a; the longitudinal segment of the force transducer beam 610a operates as an elastically deformable structural member. The plurality of strain gages 638a is used to measure the deformation of the elastically deformable structural member (i.e., the longitudinal segment of the force transducer beam 610a) resulting from the vertical force applied to surface 614 of the plate component 606, while the plurality of strain gages 646a is used to measure the deformation of the elastically deformable structural member (i.e., the longitudinal segment of the force transducer beam 610a) resulting from the shear force applied to surface 614 of the plate component 606. While in the illustrated embodiment, the longitudinal segment of the force transducer beam 610a is provided with the first and second apertures 636a, 644a therein to maximize the beam deformation when the load is applied to the first plate component 606 by reducing the cross-sectional area of the beam 610a at the locations of the apertures 636a, 644a, it is to be understood that the invention is not so limited. Rather, in other embodiments of the invention, the longitudinal segment of the force transducer beam 610a, which forms a component of the first transducer component 612a, is not provided with apertures disposed therein.

As shown in FIG. 19, the second transducer component 612b is disposed in a central region of the force transducer beam 610a. The second transducer component 612b includes: (i) a longitudinal segment of the force transducer beam 610a; (ii) first and second pluralities of strain gages 638b, 638c secured to the respective outer top and bottom surfaces of the longitudinal segment of the force transducer beam 610a; (iii) third and fourth pluralities of strain gages 638d, 638f, which are longitudinally spaced apart from the first and second pluralities of strain gages 638b, 638c, secured to the respective outer top and bottom surfaces of the longitudinal segment of the force transducer beam 610a; (iv) fifth and sixth pluralities of strain gages 646b, 646c secured to the respective outer and inner side surfaces of the longitudinal segment of the force transducer beam 610a; (v) seventh and eighth pluralities of strain gages 646d, 646f, which are longitudinally spaced apart from the fifth and sixth pluralities of strain gages 646b, 646c, secured to the respective outer and inner side surfaces of the longitudinal segment of the force transducer beam 610a. The first and second pluralities of strain gages 638b, 638c measure the bending moment imparted on second transducer component 612b at a first location by a vertical force applied to first plate component 606 and second plate component 608 (see FIGS. 19 and 22). Similarly, the third and fourth pluralities of strain gages 638d, 638f measure the bending moment imparted on second transducer component 612b at a second location by a vertical force applied to first plate component 606 and second plate component 608 (see FIGS. 19 and 22). In contrast, fifth and sixth pluralities of strain gages 646b, 646c measure the bending moment imparted on second transducer component 612b at a first location by a shear force applied to first plate component 606 and second plate component 608 (see FIGS. 19 and 22), and seventh and eighth pluralities of strain gages 646d, 646f measure the bending moment imparted on second transducer component 612b at a second location by a shear force applied to first plate component 606 and second plate component 608 (see FIGS. 19 and 22). As such, the vertical force transducer element of the second transducer component 612b comprises the first, second, third, and fourth pluralities of strain gages 638b, 638c, 638d, 638f, while the shear force transducer element of the second transducer component 612b comprises the fifth, sixth, seventh, and eighth pluralities of strain gages 646b, 646c, 646d, 646f.

Figure 22:
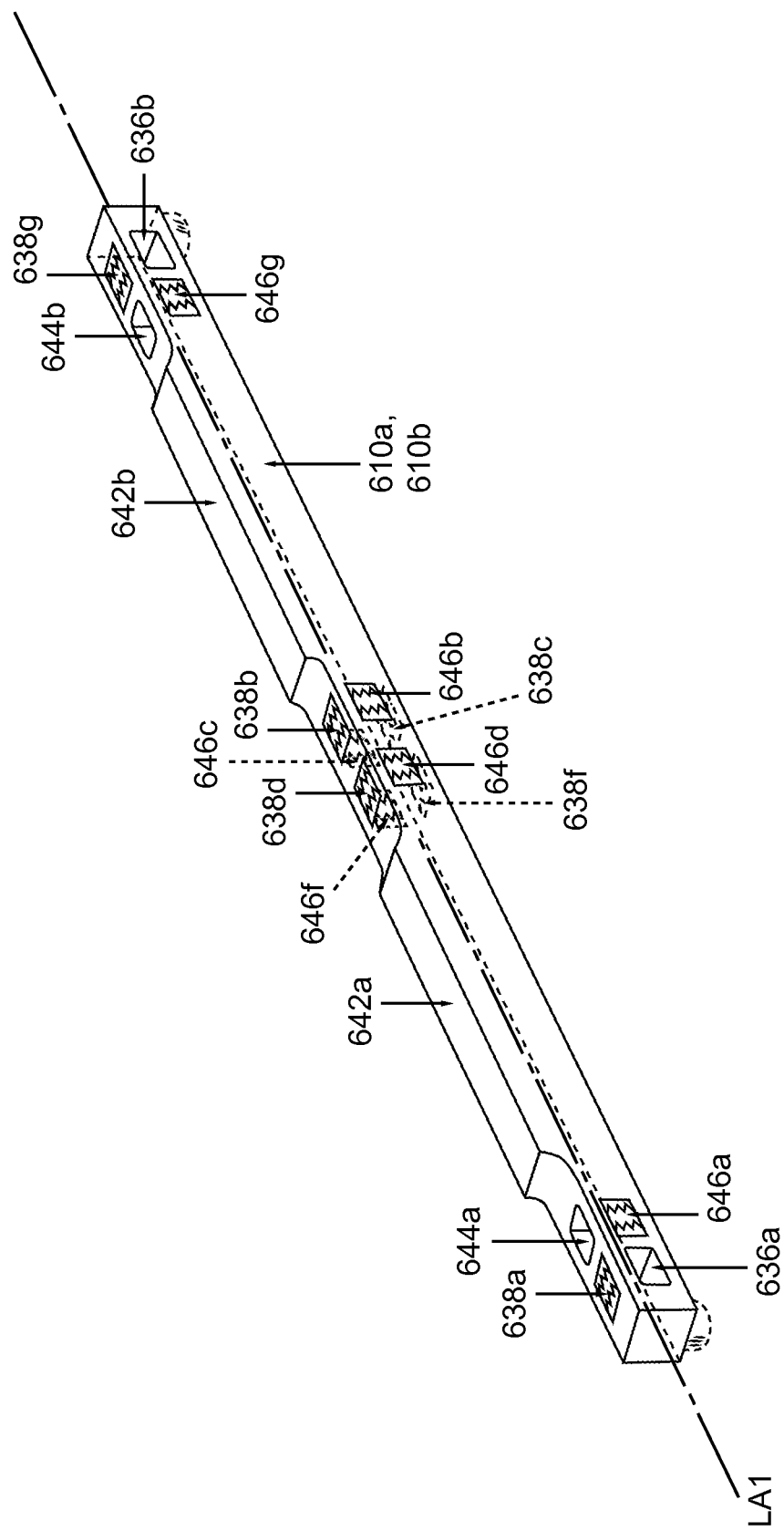
FIG. 22 is a perspective view of a transducer beam of the dual force plate assembly according to the sixth embodiment of the invention.

As best illustrated in FIG. 22, the first and third pluralities of strain gages 638b, 638d, which are mounted on the outer, top surface of the second transducer component 612b, are substantially vertically aligned with respective second and fourth pluralities of strain gages 638c, 638f, which are mounted on the outer, bottom surface of the second transducer component 612b. Similarly, the fifth and seventh pluralities of strain gages 646b, 646d, which are mounted on the outer, side surface of the second transducer component 612b, are substantially horizontally aligned with respective sixth and eighth pluralities of strain gages 646c, 646f, which are mounted on the inner, side surface of the second transducer component 612b. When the second transducer component 612b undergoes bending due to the application of a vertical force on plate components 606, 608, the first and third pluralities of strain gages 638b, 638d are configured to measure the deformation of the segmental portion of the force transducer beam 610a due to compression, while the second and fourth pluralities of strain gages 638c, 638f are configured to measure the deformation of the segmental portion of the force transducer beam 610a due to tension. Similarly, depending on the direction in which the shear force is being applied to the plate components 606, 608, one pair of the strain gages 646b, 646c, 646d, 646f is configured to measure the deformation of the segmental portion of the force transducer beam 610a due to compression, and the other pair of the strain gages 646b, 646c, 646d, 646f is configured to measure the deformation of the segmental portion of the force transducer beam 610a due to tension.

Referring again to FIG. 19, it can be seen that a third transducer component 612c is disposed at a second longitudinal end of the first transducer beam 610a, which is opposite to its first longitudinal end on which the first transducer component 612a is disposed. In other words, the third transducer component 612c is generally in a mirrored relationship with respect to the first transducer component 612a. Like the first transducer component 612a, the third transducer component 612c comprises a longitudinal segment of the force transducer beam 610a, a first aperture 636b disposed generally transversely through the longitudinal segment of the force transducer beam 610a, a second aperture 644b disposed generally vertically through the longitudinal segment of the force transducer beam 610a, a first plurality of strain gages 638g secured to the outer, top surface of the longitudinal segment of the force transducer beam 610a and substantially centered on the aperture 636b, and a second plurality of strain gages 646g secured to the outer, side surface of the longitudinal segment of the force transducer beam 610a and substantially centered on the aperture 644b. Also, similar to that described above for the first transducer component 612a, the first plurality of strain gages 638g together with the longitudinal segment of the force transducer beam 610a containing the first aperture 636b forms the vertical force transducer element of the third transducer component 612c, while the second plurality of strain gages 646g together with the longitudinal segment of the force transducer beam 610a containing the second aperture 644b forms the shear force transducer element of the third transducer component 612c. The third transducer component 612c functions in the same manner as described above for the first transducer component 612a, except that the third transducer component 612c measures the vertical and shear forces resulting from a load being applied to the second plate component 608, rather than the first plate component 606.

As shown in FIGS. 19 and 21, a second force transducer beam 610b is mounted on a side of the bottom surface of the first and second plate components 606, 608 that is opposite to the side of the bottom surface on which the first force transducer beam 610a is mounted. The second force transducer beam 610b is generally a mirror image of the first force transducer beam 610a Like the first force transducer beam 610a, the second force transducer beam 610b contains first, second, and third force transducer components 612a, 612b, 612c disposed along the length thereof with the same apertures 636a, 636b, 644a, 644b and pluralities of strain gages 638a-638d, 638f-638g, 646a-646d, 646f-646g described in conjunction with the first force transducer beam 610a.

H. Seventh Embodiment

Figure 23:
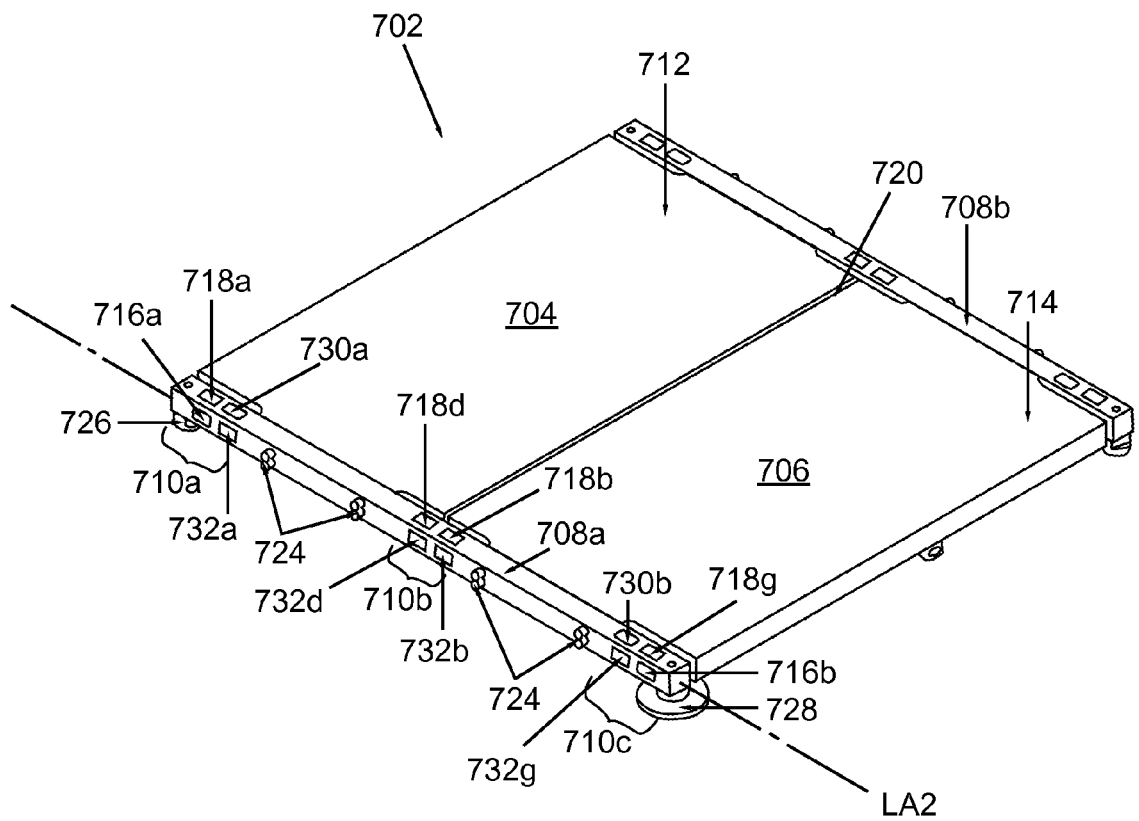
FIG. 23 is a perspective view of a dual force plate assembly of the dual force plate system according to a seventh embodiment of the invention.
Figure 24:
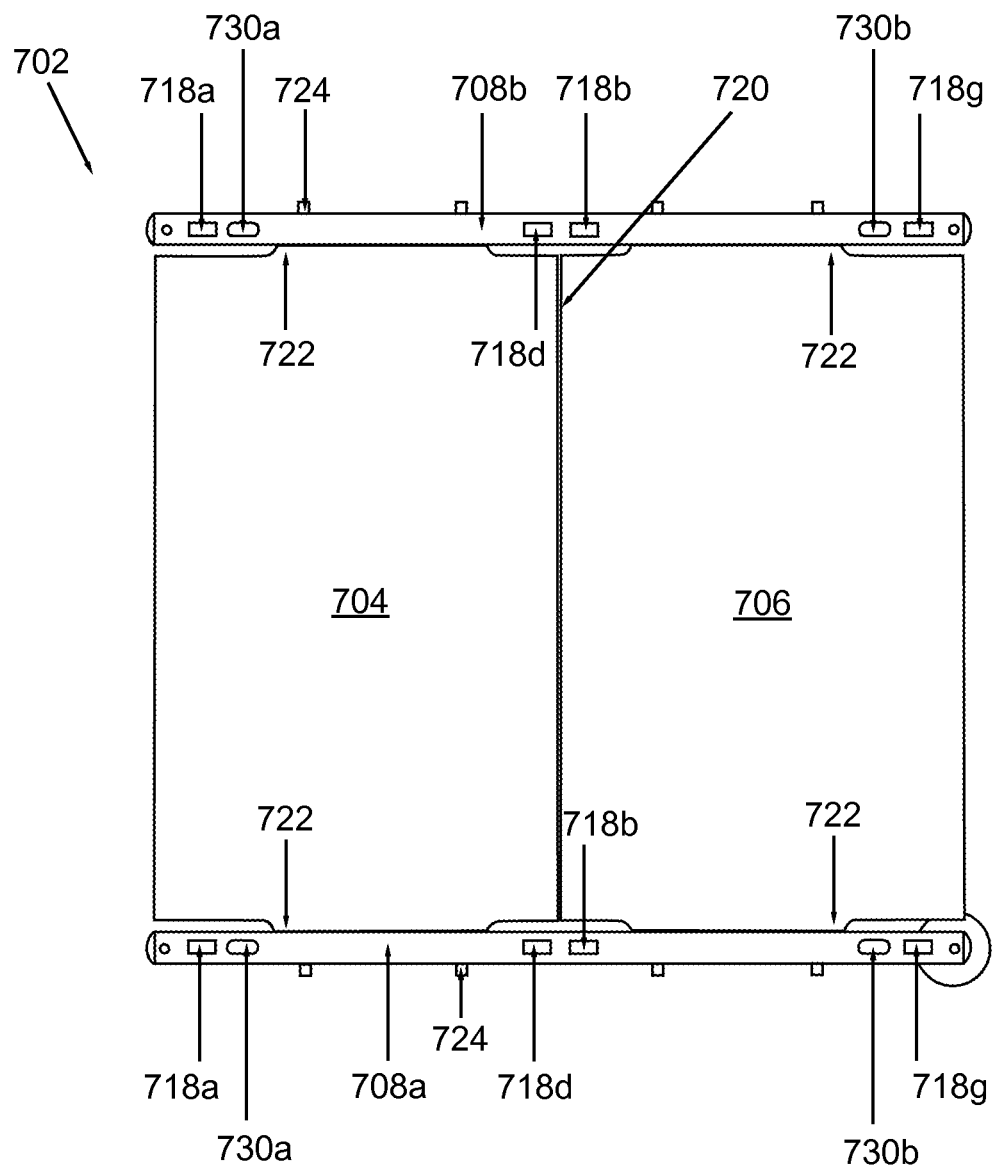
FIG. 24 is a top view of the dual force plate assembly of the dual force plate system according to the seventh embodiment of the invention.

A seventh embodiment of the dual force plate assembly is seen generally at 702 in FIGS. 23 and 24. In accordance with the seventh embodiment of the invention, the dual force plate assembly 702 for receiving a subject utilizes continuous force transducer beams 708a, 708b disposed on opposite lateral sides of the first and second plate components 704, 706, rather than force transducer beams disposed underneath the first and second plate components as described with regard to the sixth embodiment of the invention. As explained above in conjunction with the preceding embodiments, the first plate component 704 has a top surface 712 that is configured to receive a first portion of a body of a subject. Similarly, the second plate component 706 has a top surface 714 that is configured to receive a second portion of a body of a subject. Also, similar to the embodiments described above, a narrow gap 720 is provided between the first plate component 704 and the second plate component 706 so as to prevent interaction between the two plate components 704, 706.

Advantageously, in a preferred embodiment, the dual force plate assembly 702 has an overall height that is significantly lower than conventional force plates used in balance assessment. This reduction in height is made possible, in part, by the mounting of the continuous force transducer beams 708a, 708b on the lateral sides of the first and second plate components 704, 706.

Referring to FIG. 23, it can be seen that each continuous force transducer beam 708a, 708b includes a plurality of force transducer components 710a, 710b, 710c disposed along the length thereof. As shown in this figure, each of these three force transducer components 710a, 710b, 710c is linearly arranged along a longitudinal axis LA2, and each of these three force transducer components 710a, 710b, 710c intersects the longitudinal axis LA2. Also, similar to the sixth embodiment of the invention, the first and third force transducer components 710a, 710c are provided with apertures 716a, 716b, 730a, 730b disposed therethrough. Moreover, as in the sixth embodiment, the outer transducer components 710a, 710c measure the vertical and shear forces exerted on the first and second plate components 704, 706, respectively, whereas the centrally disposed transducer components 710b measure the bending moments due to vertical and shear forces resulting from a load being applied to the first and second plate components 704, 706. In FIG. 23, it can be seen that the centrally disposed transducer components 710b extend across the gap 720 between the first plate component 704 and the second plate component 706 (i.e., the centrally disposed transducer components 710b bridge the gap 720 between the first plate component 704 and the second plate component 706).

Figure 25:
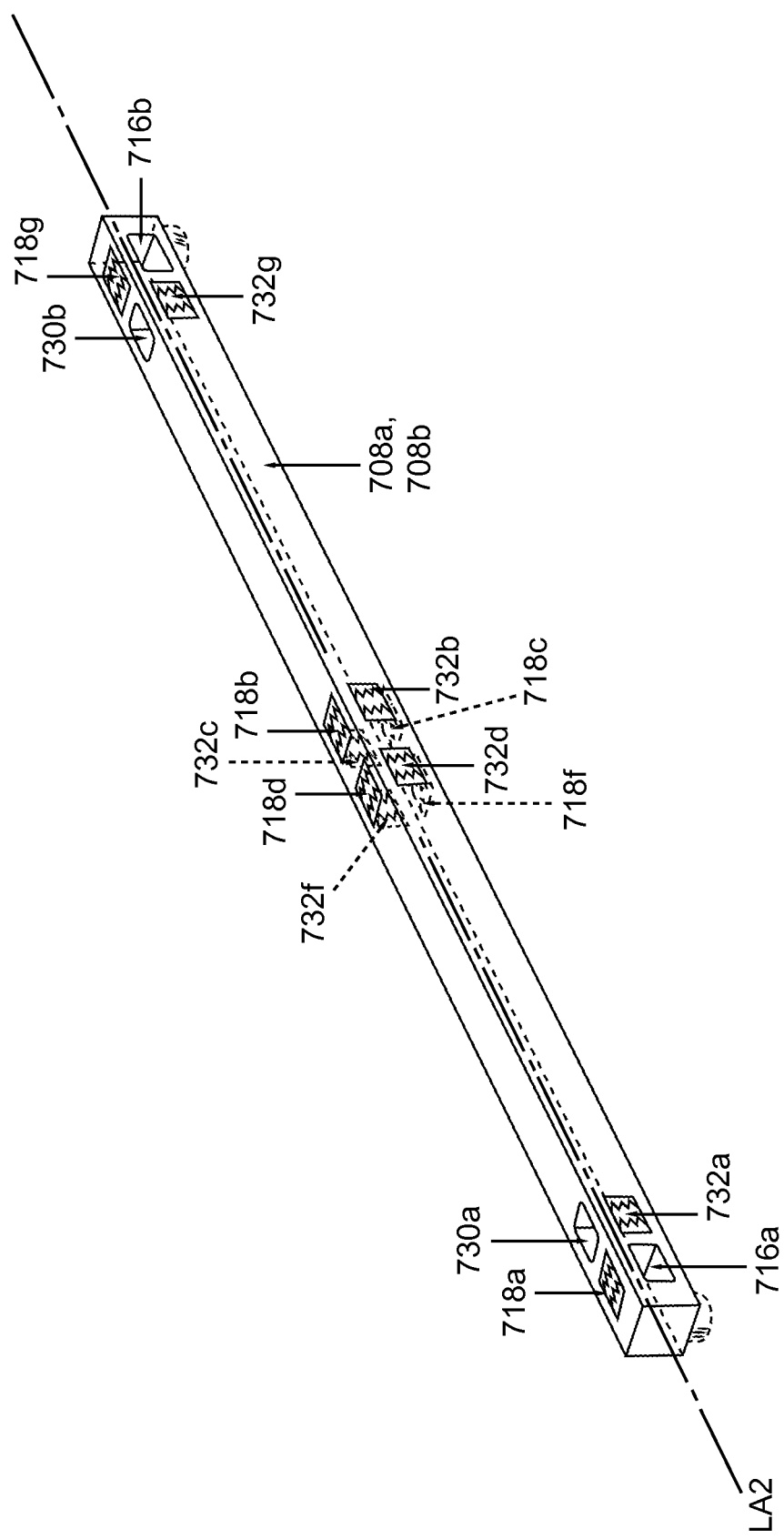
FIG. 25 is a perspective view of a transducer beam of the dual force plate assembly according to the seventh embodiment of the invention.

Like the force transducer elements 612a described above with regard to the sixth embodiment of the invention, each first force transducer element 710a is provided with a plurality of strain gages 718a secured to the outer, top surface of its associated force transducer beam 708a, 708b, and substantially centered on the aperture 716a (see FIGS. 23 and 24), and a plurality of strain gages 732a secured to the outer, side surface of its associated force transducer beam 708a, 708b and substantially centered on the aperture 730a. Also, similar to the force transducer elements 612c of the sixth embodiment, each force transducer element 710c is provided with a plurality of strain gages 718g secured to the outer, top surface of its associated force transducer beam 708a, 708b and substantially centered on the aperture 716b (see FIGS. 23 and 24), and a plurality of strain gages 732g secured to the outer, side surface of its associated force transducer beam 708a, 708b and substantially centered on the aperture 730b. In addition, like the force transducer elements 612b of the sixth embodiment of the invention, each force transducer element 710b is provided with first and second pluralities of strain gages 718b, 718c secured to the respective outer top and bottom surfaces of its associated force transducer beam 708a, 708b; third and fourth pluralities of strain gages 718d, 718f, which are longitudinally spaced apart from the first and second pluralities of strain gages 718b, 718c, secured to the respective outer top and bottom surfaces of its associated force transducer beam 708a, 708b; fifth and sixth pluralities of strain gages 732b, 732c secured to the respective outer and inner side surfaces of its associated force transducer beam 708a, 708b; seventh and eighth pluralities of strain gages 732d, 732f, which are longitudinally spaced apart from the fifth and sixth pluralities of strain gages 732b, 732c, secured to the respective outer and inner side surfaces of the longitudinal segment of its associated force transducer beam 708a, 708b (see FIGS. 23 and 25). As described above, the first, second, third, and fourth pluralities of strain gages 718b, 718c, 718d, 718f measure the bending moment due to the vertical force, while the fifth, sixth, seventh, and eighth pluralities of strain gages 732b, 732c, 732d, 732f measure the bending moment due to the shear force (refer to FIGS. 23 and 25).

Referring to FIGS. 23 and 24, it can be seen that each continuous force transducer beam 708a, 708b is fixedly attached to adjacent lateral sides of the first and second plate components 704, 706 using a plurality of screws 724. In particular, as best shown in the top view of FIG. 24, each force transducer beam 708a, 708b is attached to a respective centrally disposed protruding portion 722 on opposite lateral sides of the first plate component 704 and the second plate component 706. It is highly advantageous that the force transducer beams 708a, 708b only be connected to the centrally disposed protruding portions 722 of the first and second plate component 704, 706 so as to ensure that the total load applied to the top surfaces 712, 714 of the plate components 704, 706 is only transmitted through the force transducer elements 710a, 710b, 710c on each side thereof.

In FIG. 23, a total of four (4) screws 724 are used to connect each force transducer beam 708a, 708b to each plate component 704, 706. However, it is to be understood that the invention is not so limited. Rather, in other embodiments of the invention, more than four screws or less than four screws could be used to fixedly attach each force transducer beam 708a, 708b to each force plate component 704, 706. In yet other embodiments of the invention, the force transducer beams 708a, 708b could be connected to plate components 704, 706 by using different types of suitable adhesives (e.g., an adhesive designed for bonding metallic components to one another).

As best depicted in FIG. 23, the top surface 712 of the first plate component 704 and the top surface 714 of the second plate component 706 are both substantially aligned with the top surfaces of the transducer beams 708a, 708b in a preferred embodiment of the invention. This design feature enables the profile of the dual force plate assembly 702 to be minimized so that subjects are able to easily step on and off the dual force plate assembly 702. Also, it prevents the transducer beams 708a, 708b from posing a tripping hazard to subjects, as would be the case if the top surfaces of the transducer beams 708a, 708b were disposed above the top surfaces 712, 714 of the first and second plate components 704, 706. However, it is to be understood that the invention is not so limited. For example, in other embodiments of the invention, the top surfaces of the transducer beams 708a, 708b could be disposed below the top surfaces 712, 714 of the first and second plate components 704, 706.

In the seventh embodiment of the invention, each force transducer beam 708a, 708b is provided with respective support feet disposed at opposed longitudinal ends thereof. In FIG. 23, it can be seen that the first of the two transducer beams 708a is provided with one non-adjustable support foot 726 near a first longitudinal end thereof and one adjustable support foot 728 near the other longitudinal end thereof. The bottom portion of the second of the two force transducer beams 708b is not explicitly shown in FIG. 23, but it is provided with two (2) non-adjustable support feet disposed at opposed longitudinal ends thereof, both of which are generally the same as non-adjustable support foot 726. The dual force plate assembly 702 is designed to be installed on a floor of a building or on any other rigid surface. The adjustable support foot 728 facilitates the leveling of the dual force plate assembly 702 on an uneven surface.

I. Additional Computations Performed by the Data Acquisition/Data Processing Device 104

Next, the manner in which the data acquisition/data processing device 104 calculates the applied shear forces and the center of gravity for the subject will be explained in detail. Initially, referring to FIGS. 26, 27A-27B, and 28A-28C, the mathematical determination of the horizontally-oriented shear forces for each foot of the subject will be explained. Then, with reference to FIGS. 29-31, the determination of the center-of-gravity for the subject will be described.

Figure 26:
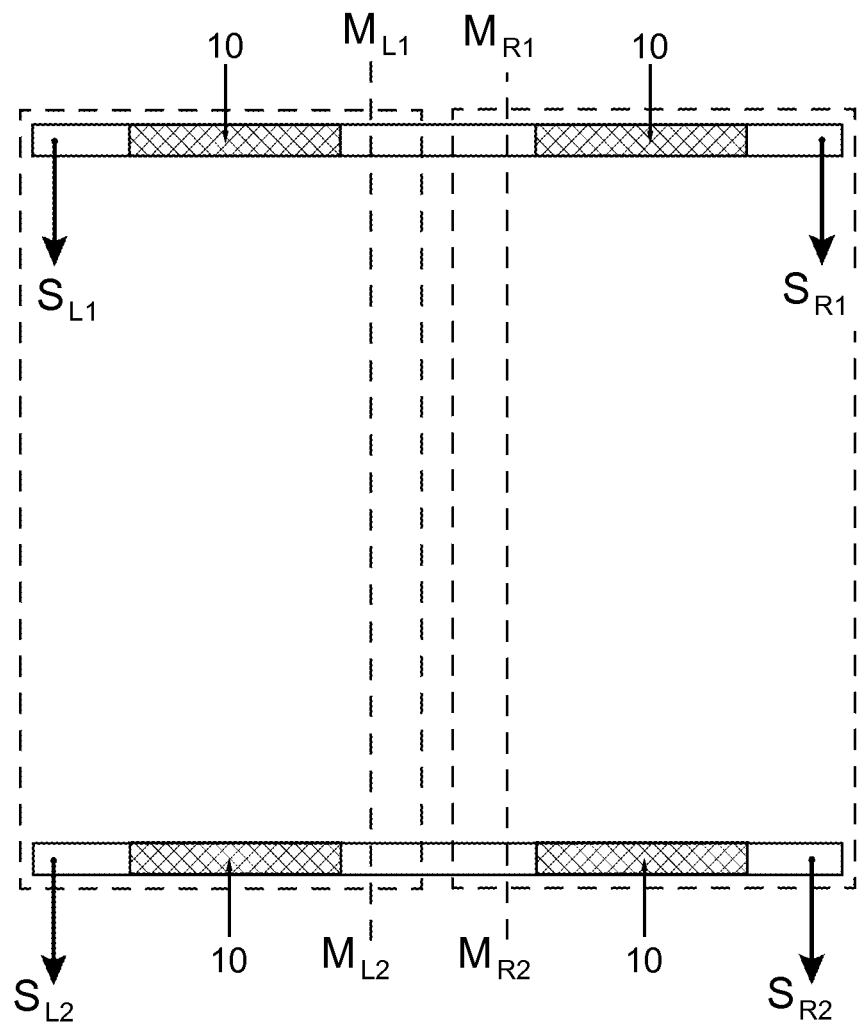
FIG. 26 is a diagrammatic bottom view of a dual force plate assembly of a dual force plate system according to another exemplary embodiment of the invention illustrating the manner in which shear forces acting on the plate are determined.

FIG. 26 depicts a diagrammatic bottom view of a dual force plate assembly of a dual force plate system, wherein the measured parameters are depicted thereon. The cross-hatched regions 10 diagrammatically denote the attachment locations of the transducer beams to the plate components. With reference to FIG. 26, the equations describing the shear-related measurements made by the force transducer beams of the dual force plate are written as follows:

$$S_L = S_{L1} + S_{L2} \tag{14}$$

$$S_R = S_{R1} + S_{R2} \tag{15}$$

$$M_L = M_{L1} + M_{L2} \tag{16}$$

$$M_R = M_{R1} + M_{R2} \tag{17}$$

where:
- $S_L$: total shear force measured by the first (left) force transducer elements disposed on opposite sides of the dual force plate;
- $S_R$: total shear force measured by the second (right) force transducer elements disposed on opposite sides of the dual force plate;
- $S_{L1}$: shear force measured by the first (left) force transducer element on the first side of the dual force plate;
- $S_{L2}$: shear force measured by the first (left) force transducer element on the second side of the dual force plate;
- $S_{R1}$: shear force measured by the second (right) force transducer element on the first side of the dual force plate;
- $S_{R2}$: shear force measured by the second (right) force transducer element on the second side of the dual force plate;
- $M_L$: left bending moment due to the shear force measured by the third force transducer elements (i.e. between the two plates) disposed on opposite sides of the dual force plate;
- $M_R$: right bending moment due to the shear force measured by the third force transducer elements (i.e. between the two plates) disposed on opposite sides of the dual force plate;
- $M_{L1}$: left plate bending moment due to the shear force measured by the third force transducer element (i.e. between the two plates) on the first side of the dual force plate;
- $M_{L2}$: left plate bending moment due to the shear force measured by the third force transducer element (i.e. between the two plates) on the second side of the dual force plate;
- $M_{R1}$: right plate bending moment due to the shear force measured by the third force transducer element (i.e. between the two plates) on the first side of the dual force plate; and
- $M_{R2}$: right plate bending moment due to the shear force measured by the third force transducer element (i.e. between the two plates) on the second side of the dual force plate.

Figure 28A:
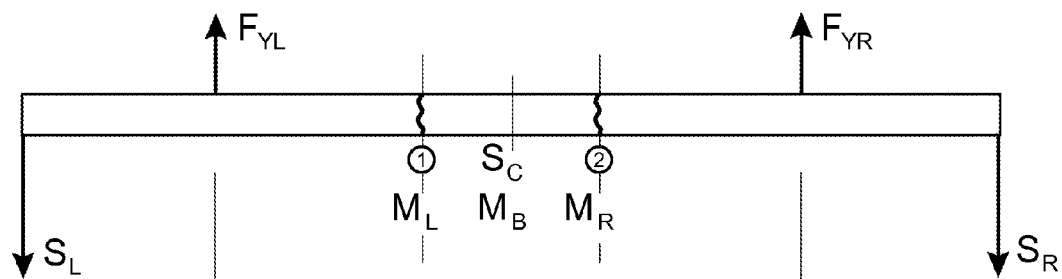
FIG. 28A is a free body diagram of a beam that diagrammatically represents the shear forces and moments acting on the dual force plate assembly according to another exemplary embodiment of the invention.
Figure 28B:
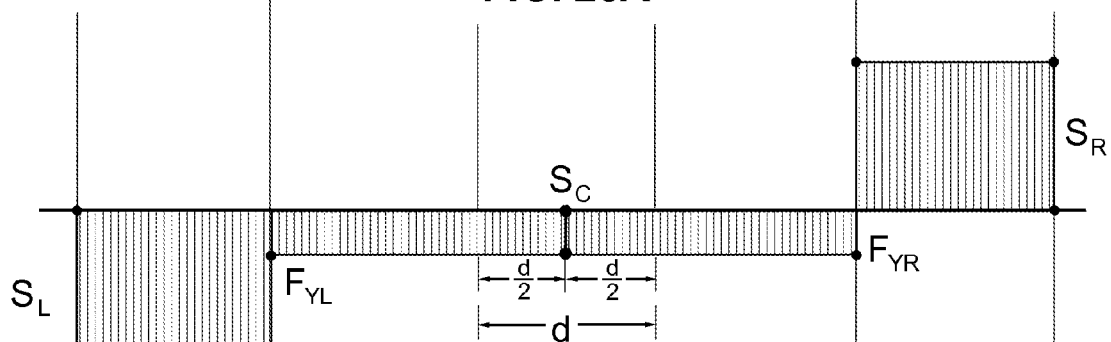
FIG. 28B is a shear diagram that diagrammatically represents the shear forces acting on the dual force plate assembly according to another exemplary embodiment of the invention.
Figure 28C:
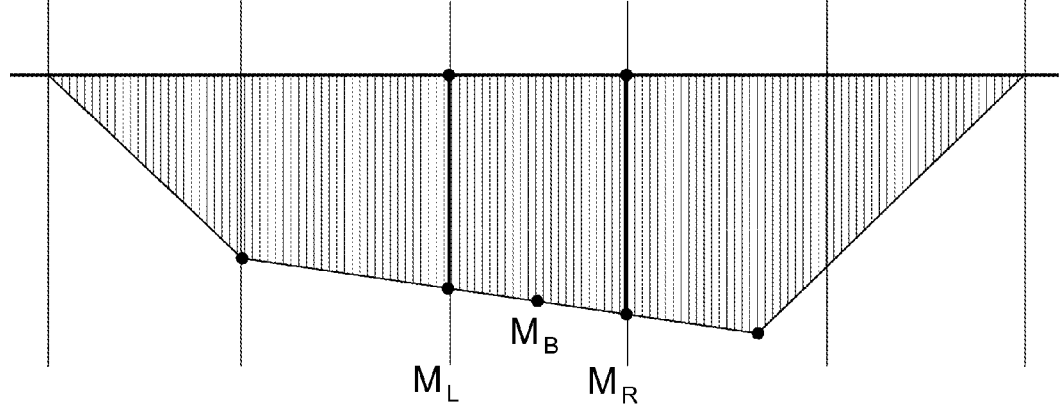
FIG. 28C is a moment diagram that diagrammatically represents the moments acting on the dual force plate assembly according to another exemplary embodiment of the invention.

In FIG. 28A, a free diagram body of the dual force plate assembly is shown in order to graphically illustrate measured shear-related parameters of the system and unknown shear forces $F_{YL}$, $F_{YR}$ being applied to the force plate by the subject. Referring to this figure, it can be seen that the dual force plate assembly is being modeled as one continuous, simply supported beam. The dual force plate assembly can be accurately modeled as a single beam because the transducer beams, each of which operatively connects the first plate to the second plate, are fixedly attached to the bottom surfaces of the first and second plates. Thus, even though separate components are utilized in the actual assembly, the dual force plate operates as if it is a single structure. As depicted in FIGS. 28A and 28B, the shear force $S_L$ acting on the left end of the assembly is sensed by first force transducer elements, while the shear force $S_R$ acting on the right end of the assembly is measured by second force transducer elements. The third force transducer elements, which are disposed proximate to the center of the transducer beam, can measure either the shear force $S_C$ and the moment $M_B$ or a left and right bending moment $M_L$, $M_R$ (i.e., they measure the load transferred between the first and second plates).

Figures 27A, 27B:
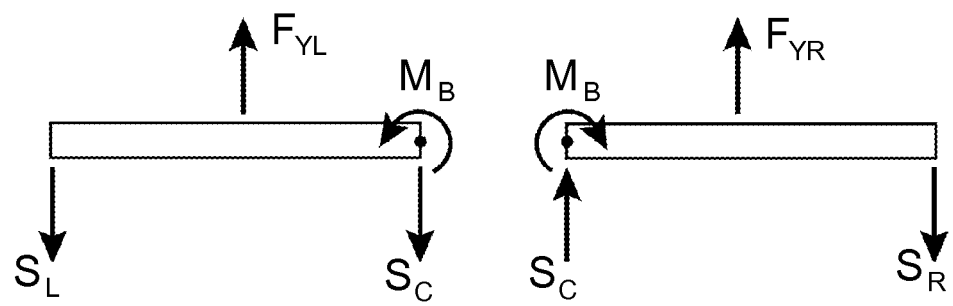
FIG. 27A is a free body diagram of the left half of the beam in FIG. 28A that diagrammatically represents the shear force(s) and moment(s) acting on the left portion of the dual force plate assembly according to another exemplary embodiment of the invention.
FIG. 27B is a free body diagram of the right half of the beam in FIG. 28A that diagrammatically represents the shear force(s) and moment(s) acting on the right portion of the dual force plate assembly according to another exemplary embodiment of the invention.

Now that both the unknown shear forces and the measured parameters of the dual force plate system have been defined, the mathematical equations for determining the unknown shear forces of the system can be formulated. As shown in FIGS. 27A and 27B, the dual force plate assembly represented diagrammatically by the beam in FIG. 28A, can be split into two separate beam sections for analysis purposes. The left beam section is illustrated in FIG. 27A, while the right beam section is depicted in FIG. 27B. Using the free body diagrams for the beam sections depicted in FIGS. 27A and 27B, the shear forces exerted on the first and second force plates by the respective left and right feet of the subject are described by the following two equations:

$$F_{YL} = S_L + S_C \quad (18)$$

$$F_{YR} = S_R - S_C \quad (19)$$

where:

$F_{YL}$: shear force exerted on the surface of the first plate component by the left foot of the subject;

$F_{YR}$: shear force exerted on the surface of the second plate component by the right foot of the subject;

$S_L$: total shear force measured by the first (left) force transducer elements disposed on opposite sides of the dual force plate;

$S_R$: total shear force measured by the second (right) force transducer elements disposed on opposite sides of the dual force plate; and $S_C$: total shear force measured by the third (center) force transducer elements disposed on opposite sides of the dual force plate.

Thus, the applied shear forces can be obtained by plugging the shear forces $S_L$, $S_R$, and $S_C$, which are measured by the force transducer elements, into equations (18) and (19) and then, solving for forces $F_{YL}$ and $F_{YR}$.

Alternatively, if each centrally disposed transducer element measures a right and left bending moment $M_R$, $M_L$, rather than the shear force and a single bending moment, then the shear force $S_C$ can be determined by utilizing the following equation:

$$S_C = \frac{(M_R - M_L)}{d} \quad (20)$$

where:

$M_L$: left bending moment due to the shear force measured by the third force transducer elements (i.e. between the two plates) disposed on opposite sides of the dual force plate (e.g., measured at a first location 1 on the beam—see FIG. 28A);

$M_R$: right bending moment due to the shear force measured by the third force transducer elements (i.e. between the two plates) disposed on opposite sides of the dual force plate (e.g., measured at a second location 2 on the beam—see FIG. 28A); and d: distance between the locations at which the respective right and left bending moments are measured (i.e., distance between first and second locations on the beam—see FIGS. 28A and 28B).

Then, the applied shear forces $F_{YL}$, $F_{YR}$ can be determined from equations (18) and (19) by using the computed shear force $S_C$ from equation (20) together with the measured shear forces $S_L$ and $S_R$.

Now, the manner in which the data acquisition/data processing device 104 calculates the center of gravity for the subject will be explained in detail. Initially, referring to FIG. 29, a side view of a subject 804 disposed on a surface of a force plate 802 is diagrammatically illustrated. As shown in this figure, the ground reaction force vector $\vec{F}$ passes through the center of pressure (COP) for the subject and the subject's center of gravity (COG). For the purpose of the analysis, the ground reaction force vector $\vec{F}$ can be represented by its constituent components, namely its vertical force component $F_Z$ and its shear force component $F_Y$. It is to be noted that, for the purposes of this analysis, only the sagittal plane of the subject is being considered.

Figure 30:
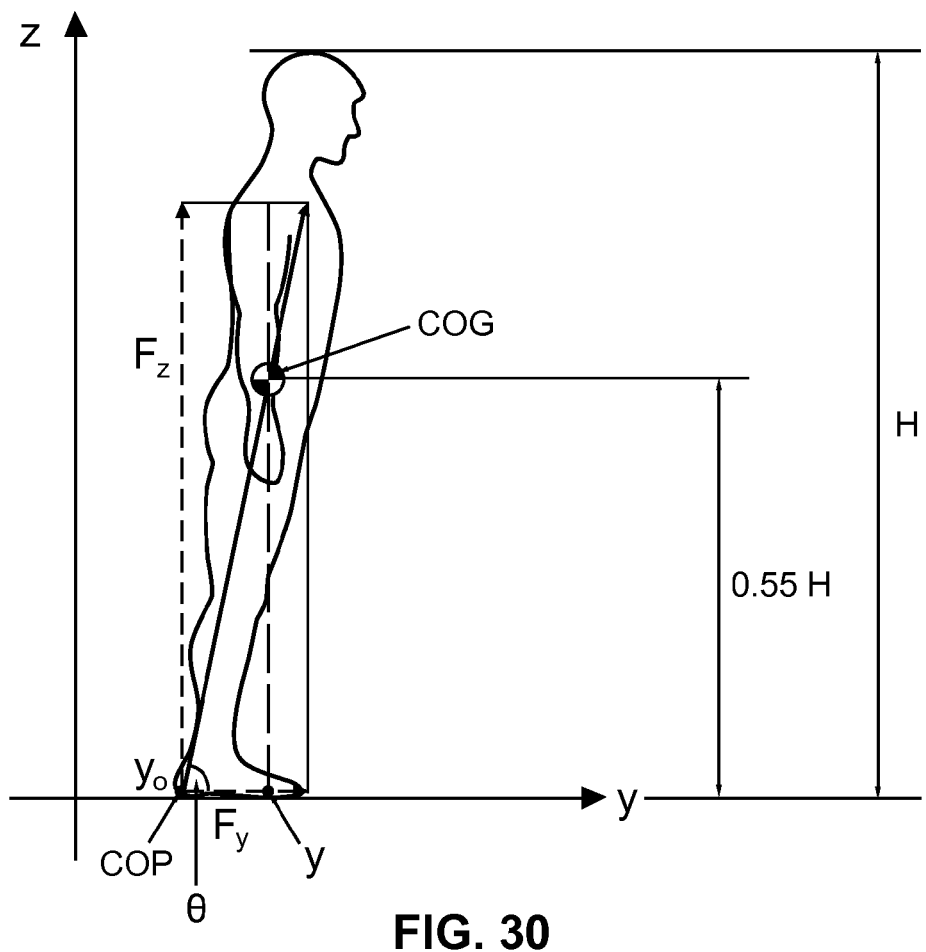
FIG. 30 is a free body diagram of a subject illustrating the force components and parameters that are used in computing center of gravity (COG) of the subject.

Then, with reference to FIG. 30, it can be seen that the y-coordinate (y) of the subject's center-of-gravity is the unknown parameter being computed by the data acquisition/data processing device 104. The center of pressure (COP) y-coordinate ($y_0$) is known from the force plate output (e.g., refer to the calculations described above in section F of the description). Also, as shown in FIG. 30, the following trigonometric relationship exists between the angle θ, the vertical force component $F_Z$, and the shear force component $F_Y$:

$$\tan\theta = \frac{F_Z}{F_Y} \quad (21)$$

Figure 31:
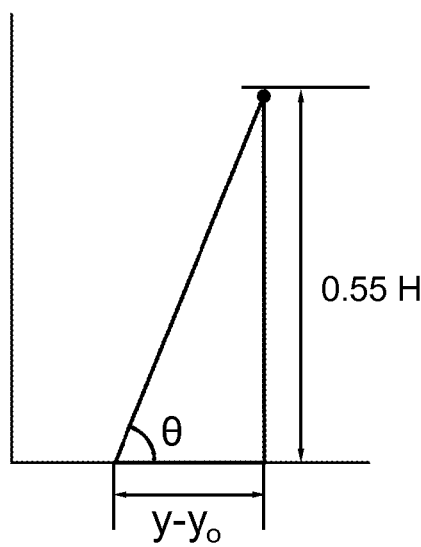
FIG. 31 is a trigonometric diagram that is used in computing center of gravity (COG) of the subject.

Now, turning to FIG. 31, it can be seen that the tangent of the angle θ is also equal to the following:

$$\tan\theta = \frac{0.55H}{y - y_0} \quad (22)$$

where:

H: height of the subject;

y: y-coordinate of the center of gravity (COG) of the subject; and $y_0$: y-coordinate of the center of pressure (COP) of the subject determined from the force plate output.

Thus, it follows that equations (21) and (22) can be combined to obtain the following relationship:

$$\frac{0.55H}{y - y_0} = \frac{F_Z}{F_Y} \quad (23)$$

This equation (23) can be initially rearranged as follows:

$$y - y_0 = \frac{F_Y}{F_Z}(0.55H) \quad (24)$$

Finally, to solve for the unknown y-coordinate (y) of the subject's center of gravity, equation (24) is rearranged in the following manner:

$$y = y_0 + \frac{F_Y}{F_Z}(0.55H) \qquad (25)$$

Therefore, the y-coordinate (y) of the subject's center of gravity can then be determined as a function of the y-coordinate ($y_0$) of the subject's center of pressure, the shear force component $F_Y$, the vertical force component $F_Z$, and the height of the subject H. The y-coordinate ($y_0$) of the subject's center of pressure, the shear force component $F_Y$, and the vertical force component $F_Z$ are all determined from the output of the force plate, whereas the height of the subject can be entered into the data acquisition/data processing device 104 by the user of the system (i.e., after the system user acquires the height value from the subject being tested). Advantageously, the computational method described above enables the subject's center of gravity to be accurately determined using the force measurement system.

J. Additional Embodiments

Figure 32:
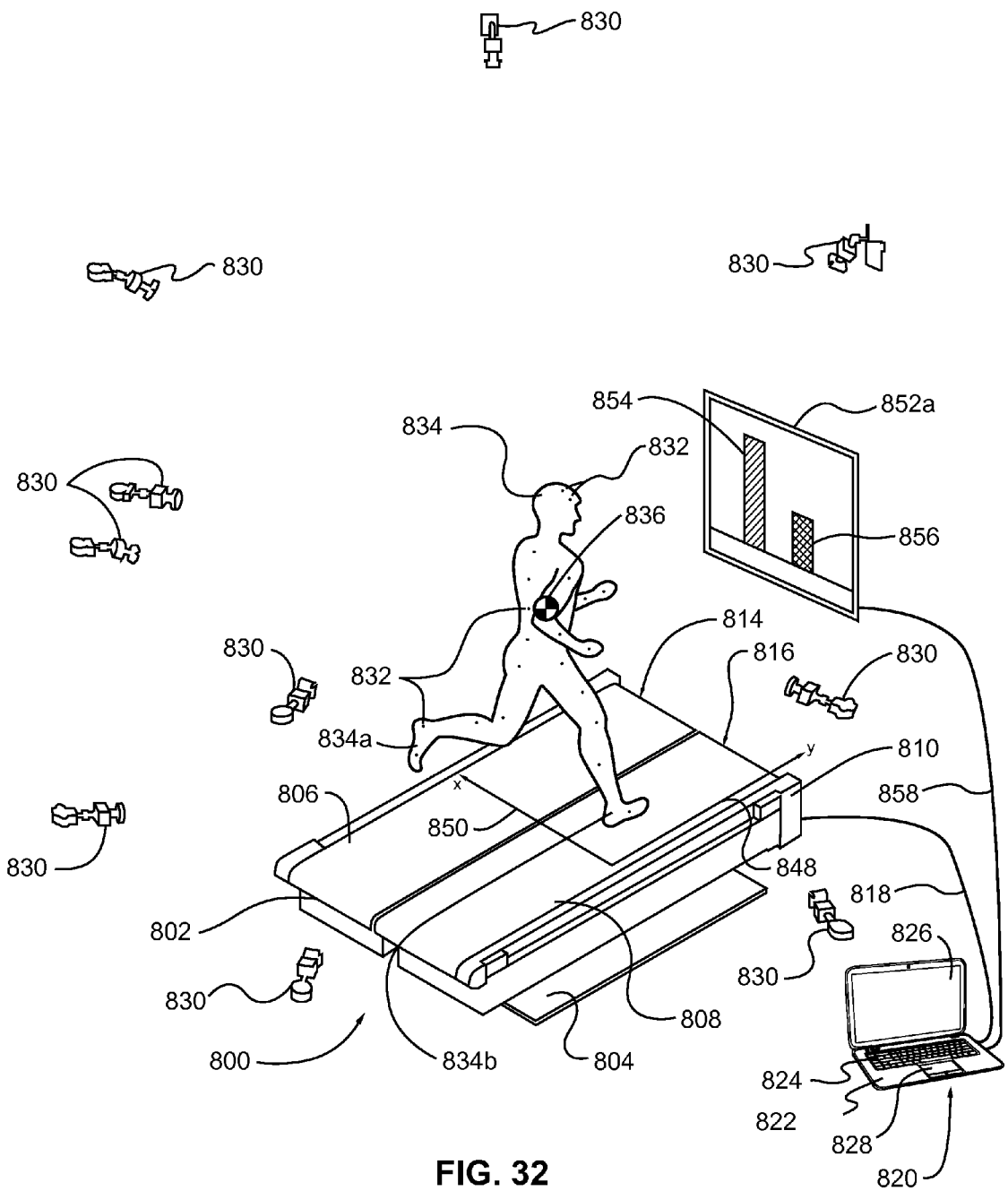
FIG. 32 is a perspective view of a force measurement system with an instrumented treadmill, a motion capture system, and a visual display device providing biofeedback to a subject on the instrumented treadmill, according to an eighth embodiment of the invention.

In a further embodiment, a modified version of the force measurement system 800 may comprise a force measurement device in the form of an instrumented treadmill 802. Like the force measurement assemblies 102, 202, 302, 402, 502, 602, 702 described above, the instrumented treadmill 802 is configured to receive a subject thereon. As illustrated in FIG. 32, the instrumented treadmill 802 is attached to the top of a base plate 804. The instrumented treadmill 802 has a plurality of top surfaces (i.e., a left and right rotating belt 806, 808) that are each configured to receive a portion of a body of a subject (e.g., the left belt 806 of the instrumented treadmill 802 receives a left leg 834a of a subject 834, whereas the right belt 808 of the instrumented treadmill 802 receives a right leg 834b of the subject 834).

In a preferred embodiment, a subject 834 walks or runs in an upright position atop the treadmill 802 with the feet of the subject contacting the respective top surfaces 814, 816 of the treadmill belts 806, 808. The belts 806, 808 of the treadmill 802 are rotated by independent electric actuator assemblies with speed adjustment mechanisms 810. In the illustrated embodiment, each electric actuator assembly and associated speed adjustment mechanism 810 comprises an electric motor with a variable speed control device operatively coupled thereto. Each electric actuator assembly and associated speed adjustment mechanism 810 is capable of rotating its respective treadmill belt 806, 808 at a plurality of different speeds. The speed adjustment mechanisms adjust the speed at which each of their respective treadmill belts 806, 808 are rotated. Similar to the force measurement assemblies 102, 202, 302, 402, 502, 602, 702 described above, the instrumented treadmill 802 is operatively connected to the data acquisition/data processing device 820 by an electrical cable 818. While they are not readily visible in the top perspective view of FIG. 32 due to their location, the instrumented treadmill 802, like the force measurement assemblies 102, 202, 302, 402, 502, 602, 702, includes a plurality of force transducers (e.g., four (4) pylon-type force transducers 812—see FIG. 33) disposed below each rotating belt 806, 808 of the treadmill 802 so that the loads being applied to the top surfaces of the belts 806, 808 can be measured. Similar to that described above for the force measurement assemblies 102, 202, 302, 402, 502, 602, 702, the separated belts 806, 808 of the instrumented treadmill 802 enables the forces and/or moments applied by the left and right legs 834a, 834b of the subject 834 to be independently determined. The electrical cable 818 operatively couples both the electric actuator assemblies with speed adjustment mechanisms 810 and the pylon-type force transducers 812 of the instrumented treadmill 802 to the data acquisition/data processing device 820.

Figure 33:
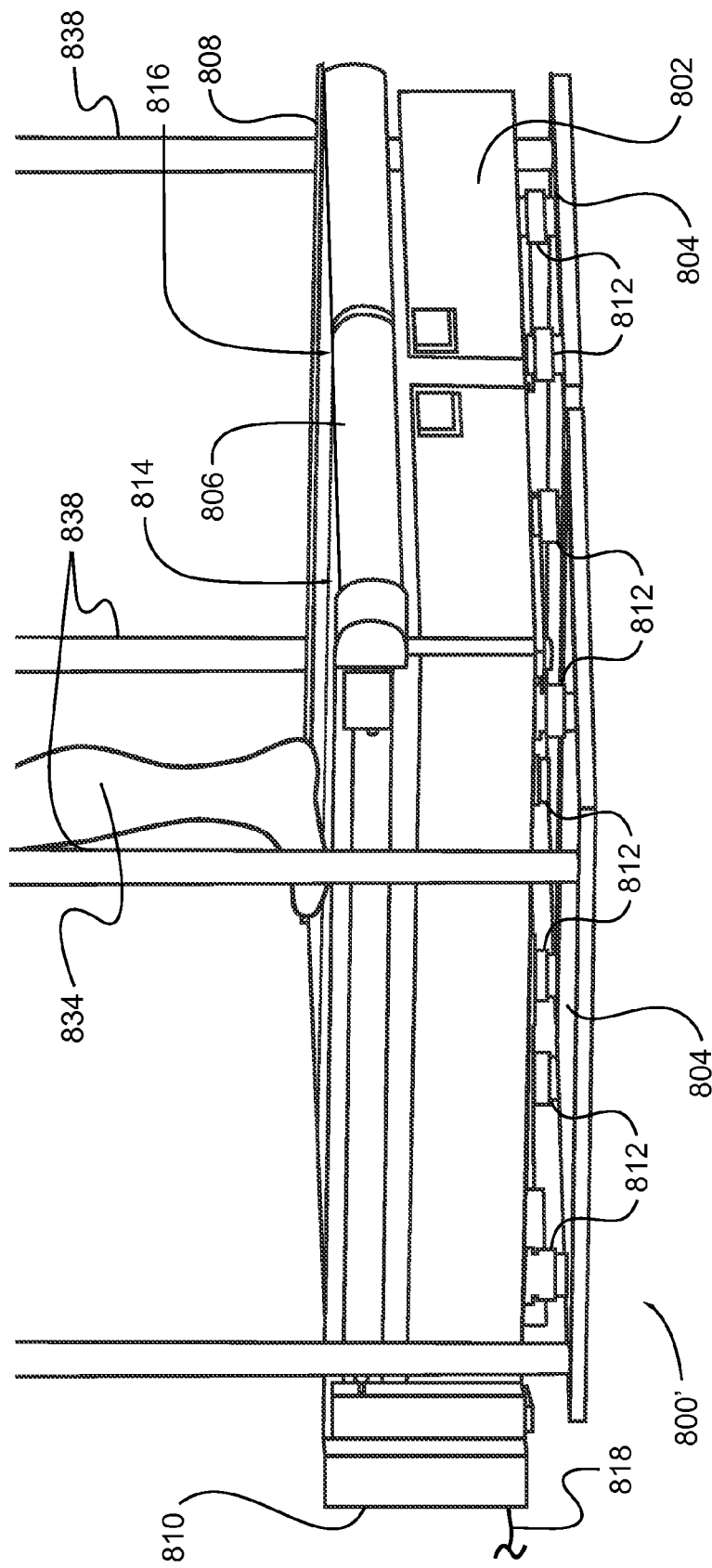
FIG. 33 is an end-side perspective view illustrating the pylon-type force transducers of the instrumented treadmills of FIGS. 32, 34, and 35.

As mentioned above, each of the treadmill belts 806, 808 is supported atop four (4) pylon-type force transducers 812 (or pylon-type load cells) that are disposed underneath, and near each of the four corners (4) of the left rotating belt 806 of the treadmill 802 and each of the four corners (4) of the right rotating belt 808 (see FIG. 33). Each of the eight (8) illustrated pylon-type force transducers 812 has a plurality of strain gages adhered to the outer periphery of a cylindrically-shaped force transducer sensing element for detecting the mechanical strain of the force transducer sensing element imparted thereon by the force(s) applied to the belt surfaces 814, 816 of the instrumented treadmill 802. As shown in FIG. 33, a respective base plate 804 is provided underneath the transducers 812 of each treadmill belt assembly 806, 808 for facilitating the mounting of the instrumented treadmill 802 to a support surface, such as a floor.

In an alternative embodiment, rather than using four (4) pylon-type force transducers 812 on each treadmill belt assembly 806, 808, force transducers in the form of transducer beams could be provided under each treadmill belt assembly 806, 808. In this alternative embodiment, the left treadmill belt assembly 806 could comprise two transducer beams that are disposed underneath, and on generally opposite sides of the treadmill belt assembly 806. Similarly, in this embodiment, the right treadmill belt assembly 808 could comprise two transducer beams that are disposed underneath, and on generally opposite sides of the right treadmill belt assembly 808. Similar to the pylon-type force transducers 812, the force transducer beams could have a plurality of strain gages attached to one or more surfaces thereof for sensing the mechanical strain imparted on the beam by the force(s) applied to the surfaces 814, 816 of the instrumented treadmill 802.

Rather, than using four (4) force transducer pylons under each plate, or two spaced apart force transducer beams under each plate, it is to be understood that the instrumented treadmill 802 can also utilize the force transducer technology described above with regard to the preceding embodiments (e.g., that described above in conjunction with the dual force plate assembly 102).

In the illustrated embodiment, the electrical cable 818 is used for the transmission of data between the instrumented treadmill 802 and the data acquisition/data processing device 820. A separate power cable is used to provide power to the instrumented treadmill 802 (e.g., a power cable connected directly to the electrical power system of the building in which the treadmill 802 is disposed). While a hardwired data connection is provided between the instrumented treadmill 802 and the data acquisition/data processing device 820 in the illustrated embodiment, it is to be understood that the instrumented treadmill 802 can be operatively coupled to the data acquisition/data processing device 820 using other signal transmission means, such as a wireless data transmission system.

Similar to the data acquisition/data processing device 104 described above in conjunction with FIG. 1, the data acquisition/data processing device 820 (e.g., in the form of a laptop digital computer) generally includes a base portion 822 with a central processing unit (CPU) disposed therein for collecting and processing the data that is received from the instrumented treadmill 802, and a plurality of devices 824-828 operatively coupled to the central processing unit (CPU) in the base portion 822. Preferably, the devices that are operatively coupled to the central processing unit (CPU) comprise user input devices 824, 828 in the form of a keyboard 824 and a touchpad 828, as well as a graphical user interface in the form of a laptop LCD screen 826. While a laptop type computing system is depicted in FIG. 32, one of ordinary skill in the art will appreciate that another type of data acquisition/data processing device 820 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse).

The acquisition and processing of the load data carried out by the force measurement system 800 is similar to that described above with regard to FIG. 8. Initially, a load is applied to the instrumented treadmill 802 by a subject disposed thereon. The load is transmitted from the treadmill belt assemblies 806, 808 to its respective set of pylon-type force transducers 812 (or force transducer beams). As described above, in the illustrated embodiment, each treadmill belt assembly 806, 808 comprises four (4) pylon-type force transducers 812 disposed thereunder. Preferably, these pylon-type force transducers 812 are disposed near respective corners of each treadmill belt assembly 806, 808. In a preferred embodiment, each of the pylon-type force transducers 812 includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 806, 808. For each plurality of strain gages disposed on the pylon-type force transducers 812, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 812 disposed under each treadmill belt assembly 806, 808 output a total of thirty-two (32) raw output voltages (signals) in either analog or digital form. In some embodiments, if the output voltages (signals) are in analog form, the thirty-two (32) raw output voltages (signals) from each treadmill belt assembly 806, 808 are then transmitted to a preamplifier board for preconditioning. The preamplifier board is used to increase the magnitudes of the transducer analog voltages, and preferably, to convert the analog voltage signals into digital voltage signals as well. After which, in one or more embodiments, each treadmill belt assembly 806, 808 transmits the output signals $S_{FPO1}$-$S_{FPO32}$ to a main signal amplifier/converter. Depending on whether the preamplifier board also includes an analog-to-digital (A/D) converter, the force plate output signals $S_{FPO1}$-$S_{FPO32}$ could be either in the form of analog signals or digital signals. The main signal amplifier/converter further magnifies the force plate output signals $S_{FPO1}$-$S_{FPO32}$, and if the signals $S_{FPO1}$-$S_{FPO32}$ are of the analog-type (for a case where the preamplifier board did not include an analog-to-digital (A/D) converter), it may also convert the analog signals to digital signals. Then, the signal amplifier/converter transmits either the digital or analog signals $S_{ACO1}$-$S_{ACO32}$ to the data acquisition/data processing device 820 (computer 820) so that the forces and/or moments that are being applied to the surfaces 814, 816 of the treadmill belts 806, 808 can be transformed into output load values. In addition to hardware components, such as a microprocessor, memory, and data storage device(s), the data acquisition/data processing device 820 may further comprise an analog-to-digital (A/D) converter if the signals $S_{ACO1}$-$S_{ACO32}$ are in the form of analog signals. In such a case, the analog-to-digital converter will convert the analog signals into digital signals for processing by the microprocessor of the data acquisition/data processing device 820.

In one or more embodiments, when the data acquisition/data processing device 820 receives the voltage signals $S_{ACO1}$-$S_{ACO32}$, it initially transforms the signals into output forces and/or moments by multiplying the voltage signals $S_{ACO1}$-$S_{ACO32}$ by a calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 814 of the left treadmill belt assembly 806 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 816 of the right treadmill belt assembly 808 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the data acquisition/data processing device 820.

Now, the various ways in which the data acquisition/data processing device 820 may determine a position of a body portion (e.g., torso, pelvis, or head) of the subject 834 and control the respective speeds of the treadmill belts 806, 808 using the position determined for the body portion of the subject 834 will be described. As described hereinafter, the instrumented treadmill 802 is provided with an automatic belt speed control system that regulates the speed of the treadmills belts 806, 808 in accordance with a position of a body portion of the subject in multi-dimensional space (i.e., 3-dimensional space). Initially, a manner which the data acquisition/data processing device 820 determines a position of a center of gravity 836 of the subject 834, and controls the respective speeds of the treadmill belts 806, 808 accordingly thereto, will be described with reference to FIG. 32.

The objective of determining the position of a center of gravity 836 of the subject 834, and controlling the respective speeds of the treadmill belts 806, 808 accordingly, is to update the instrumented treadmill belt speed set points such that the treadmill 802 synchronizes its speed with the speed of the subject 834. In other words, as the subject 834 chooses to increase/decrease his/her gait speed on the treadmill 802, the belt speeds are adjusted automatically. In general, the data acquisition/data processing device 820 is specially programmed to carry out the following steps in determining the belt speeds of the self-pacing treadmill 802: (i) calculate the subject's center-of-pressure along the y-axis ($COP_y$), (ii) calculate the subject's approximated center-of-gravity along the y-axis ($COG_y$), and (iii) update the belt speed set point. As described above, the instrumented dual belt treadmill 802 of FIG. 32 is capable of measuring the ground reaction forces and moments ($F_x$, $F_y$, $F_z$, $M_x$, $M_y$, $M_z$) on each belt 806, 808 independently. As shown in FIG. 32, the y coordinate axis 848 extends in a lengthwise direction of the instrumented treadmill 802 from front end to the rear end of the treadmill 802, while the x coordinate axis 850 extends in a widthwise direction of the treadmill 802, perpendicular to the y coordinate axis 848.

In accordance with the first part of the calculation procedure carried out by the data acquisition/data processing device 820, based on the force and moment measurements made by the pylon-type force transducers 812, the data acquisition/data processing device 820 is specially programmed to calculate the y-coordinate of the point of application (i.e. center-of-pressure) ($COP_y$) of a subject's total force vector using the following equation:

$$COP_y = \frac{-h \cdot F_y - M_x}{F_z} \quad (26)$$

where:
h: the height difference of the belt surface 814, 816 from the xy-plane of the measurement coordinate system;
$F_y$: measured force along the y-axis;
$M_x$: measured moment along the x-axis; and
$F_z$: measured force along the z-axis.

In other words, in the illustrated embodiment, the data acquisition/data processing device 820 is specially programmed to compute the y-coordinate of the point of application (i.e. center-of-pressure) ($COP_y$) of a subject's total force vector as a function of the height difference of the belt surface 814, 816 from the xy-plane of the measurement coordinate system, the measured force along the y-axis, the measured moment along the x-axis, and the measured force along the z-axis.

In accordance with the second part of the calculation procedure carried out by the data acquisition/data processing device 820, the data acquisition/data processing device 820 is specially programmed to calculate the approximated center-of-gravity ($COG_y$) of the subject 834 by applying a digital filter to the center-of-pressure $COP_y$ data in real-time with a sampling interval of 1 milliseconds (ms). In an illustrative embodiment, the applied filter is a second-order digital Butterworth-type with 0.7 Hz cut-off frequency. Accordingly, the center-of-gravity $COG_y$ of the subject 834 at time t is calculated with the following equations:

$$COG_y(t) = c_1 \cdot COP_y(t-2t_s) + c_2 \cdot COP_y(t-t_s) + c_1 \cdot COP_y(t) + c_3 \cdot COG_y(t-2t_s) + c_4 \cdot COG_y(t-t_s) \quad (27)$$

$$c_1 = 4.8211046858E{-6} \quad (28)$$

$$c_2 = 9.6422093716E{-6} \quad (29)$$

$$c_3 = -0.9937992683 \quad (30)$$

$$c_4 = 1.9937799838 \quad (31)$$

$$t_s = 0.001 \quad (32)$$

where:
$COP_y$: subject's center-of-pressure along the y-axis;
$COG_y$: subject's approximated center-of-gravity along the y-axis;
$c_1, c_2, c_3, c_4$: Butterworth filter coefficients; and
$t_s$: time sampling interval.

In other words, in the illustrated embodiment, the data acquisition/data processing device 820 is specially programmed to compute the subject's approximated center-of-gravity along the y-axis as a function of subject's center-of-pressure along the y-axis, the Butterworth filter coefficients, and the time sampling interval.

In accordance with the third part of the calculation procedure carried out by the data acquisition/data processing device 820, the data acquisition/data processing device 820 is specially programmed to calculate the belt speed set point at time t using a proportional-integral-derivative (PID) control-based routine, as given by the following equation:

$$v_b(t) = v_b(t-t_s) + K_P \cdot COG_y(t) + \frac{K_D}{t_s} \cdot [COG_y(t) - COG_y(t-t_s)] + K_I \cdot \frac{t_s}{2} \cdot [COG_y(t) + COG_y(t-t_s)] \quad (33)$$

where:
$v_b$: treadmill belt speed;
$K_P$: proportional gain constant for subject's approximated center-of-gravity along the y-axis;
$K_I$: integral gain constant for subject's approximated center-of-gravity along the y-axis; and
$K_D$: derivative gain constant for subject's approximated center-of-gravity along the y-axis.

In other words, in the illustrated embodiment, the data acquisition/data processing device 820 is specially programmed to compute the treadmill belt speed for each of the treadmill belts 806, 808 as a function of the subject's approximated center-of-gravity along the y-axis, the proportional, integral, and derivative gain constants for subject's approximated center-of-gravity along the y-axis, and the time sampling interval.

In the illustrative embodiment, the belt speed calculation procedure is programmed on an embedded computer (i.e., the data acquisition/data processing device 820) that provides a deterministic program cycle time of 1 milliseconds (ms). In other words, the belt speed update rate of 1 kHz is guaranteed by either the hardware architecture of the embedded computer 820 or a real-time operating system that runs on it. The updated belt speed set points are sent to a servo controller (i.e., each speed adjustment mechanism), which controls the belt motor speed with a closed-loop rate of 4 kHz.

Figure 29:
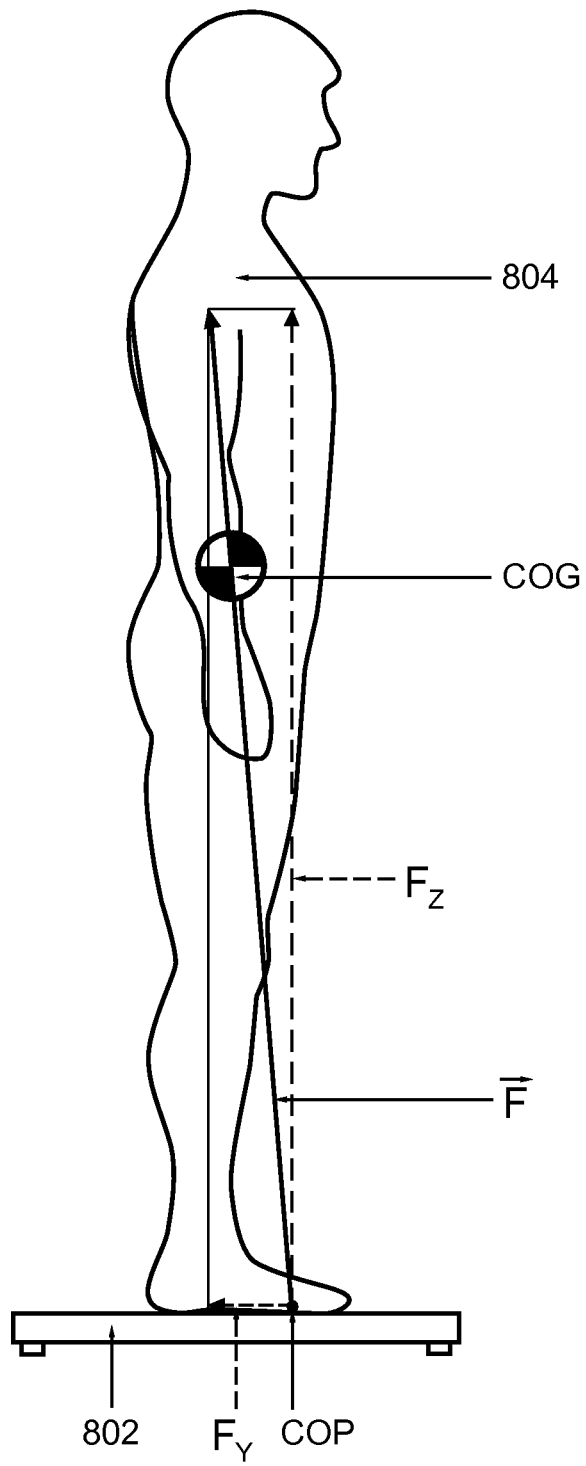
FIG. 29 is a diagrammatic side view of a subject disposed on a surface of a force plate, wherein the center of pressure (COP) and the center of gravity (COG) of the subject are depicted thereon along with the vertical force and shear force components.

Rather than approximating the subject's center-of-gravity along the y-axis using Butterworth-type filter and equations (27)-(32) above, in an alternative embodiment, the subject's center-of-gravity along the y-axis is directly calculated using equations (21)-(25) above in the manner described in conjunction with FIGS. 29-31. Then, once the subject's center-of-gravity along the y-axis is determined using equations (21)-(25), the treadmill belt speed is computed using equation (33), as explained above. As such, when the subject's center-of-gravity along the y-axis is directly calculated by the data acquisition/data processing device 820 using equations (21)-(25), the data acquisition/data processing device 820 is specially programmed to compute the center of gravity position ($COG_y$) for the subject as a function of at least one vertical force quantity, at least one shear force quantity, a height of the subject, and a center of pressure coordinate determined using the one or more output load components (i.e., the y-coordinate ($y_0$) of the subject's center of pressure).

Now, another manner in which the data acquisition/data processing device 820 may determine a position of a body portion (e.g., torso, pelvis, or head) of the subject 834 and control the respective speeds of the treadmill belts 806, 808 using the position determined for the body portion of the subject 834 will be described with reference again to FIG. 32. In particular, the data acquisition/data processing device 820 may also determine the position of the body portion of the subject 834 by utilizing the motion capture system illustrated in FIG. 32.

As shown in FIG. 32, a subject 834 is provided with a plurality of markers 832 disposed thereon. These markers 832 are used to record the position of the torso and limbs of the subject 834 in 3-dimensional space. A plurality of cameras 830 are disposed on all sides of the subject 834 (i.e., the cameras 830 surround the subject 834), and are used to track the position of the markers 832 as the subject 834 moves his or her torso and limbs in 3-dimensional space. While ten (10) cameras 830 are depicted in FIG. 32, one of ordinary skill in the art will appreciate that more or less cameras can be utilized, provided that the motion of the subject 834 is capable of being captured from substantially all angles. In one embodiment of the invention, the subject 834 has a plurality of single markers applied to anatomical landmarks (e.g., the iliac spines of the pelvis, the malleoli of the ankle, and the condyles of the knee), and/or clusters of markers applied to the middle of body segments. As the subject 834 executes particular movements on the instrumented treadmill 802, the data acquisition/data processing device 820 is specially programmed to calculate the trajectory of each marker 832 in three (3) dimensions. Then, once the positional data is obtained using the motion capture system of FIG. 32, inverse kinematics may be employed in order to further determine the joint angles of the subject 834.

The motion capture system of FIG. 32 generates motion capture data that is representative of the captured motion of the body portion of the subject, and the data acquisition/data processing device 820 is specially programmed to determine the position of the body portion (e.g., torso, pelvis, or head) of the subject 834 from the motion capture data generated by the motion capture system (e.g., the motion capture data may be used to determine the position of the subject 834 relative to the center of the treadmill belts 806, 808 or to approximate the subject's center-of-gravity along the y-axis). Then, by using an equation that is similar to equation (33) above, the speed of the treadmill belts 806, 808 is controlled using the position that is determined for the subject 834.

While the motion capture system of FIG. 32 described above employs a plurality of markers 832, it is to be understood that the invention is not so limited. Rather, in another embodiment of the invention, a markerless motion detection/motion capture system is utilized. The markerless motion capture system uses a plurality of high speed video cameras to record the motion of a subject without requiring any markers to be placed on the subject. Both of the aforementioned marker and markerless motion detection/motion capture systems are optical-based systems. In one embodiment, the optical motion capture system utilizes visible light, while in another alternative embodiment, the optical motion capture system employs infrared light (e.g., the system could utilize an infrared (IR) emitter to project a plurality of dots onto objects in a particular space as part of a markless motion capture system). For example, in one or more embodiments, the optical motion capture system may comprise a motion capture device with one or more cameras, one or more infrared (IR) depth sensors, and one or more microphones, which may be used to provide full-body three-dimensional (3D) motion capture, facial recognition, and voice recognition capabilities. It is also to be understood that, rather than using an optical motion detection/capture system, a suitable magnetic or electro-mechanical motion detection/capture system may also be employed to determine the position of the subject 834 on the instrumented treadmill 802.

Next, yet another manner in which the data acquisition/data processing device 820 may determine a position of a body portion (e.g., torso, pelvis, or head) of the subject 834 and control the respective speeds of the treadmill belts 806, 808 using the position determined for the body portion of the subject 834 will be described with reference to FIG. 34. In particular, the data acquisition/data processing device 820 may also determine the position of the body portion of the subject 834 by utilizing the position detection device 840, 842 illustrated in FIG. 34.

Figure 34:
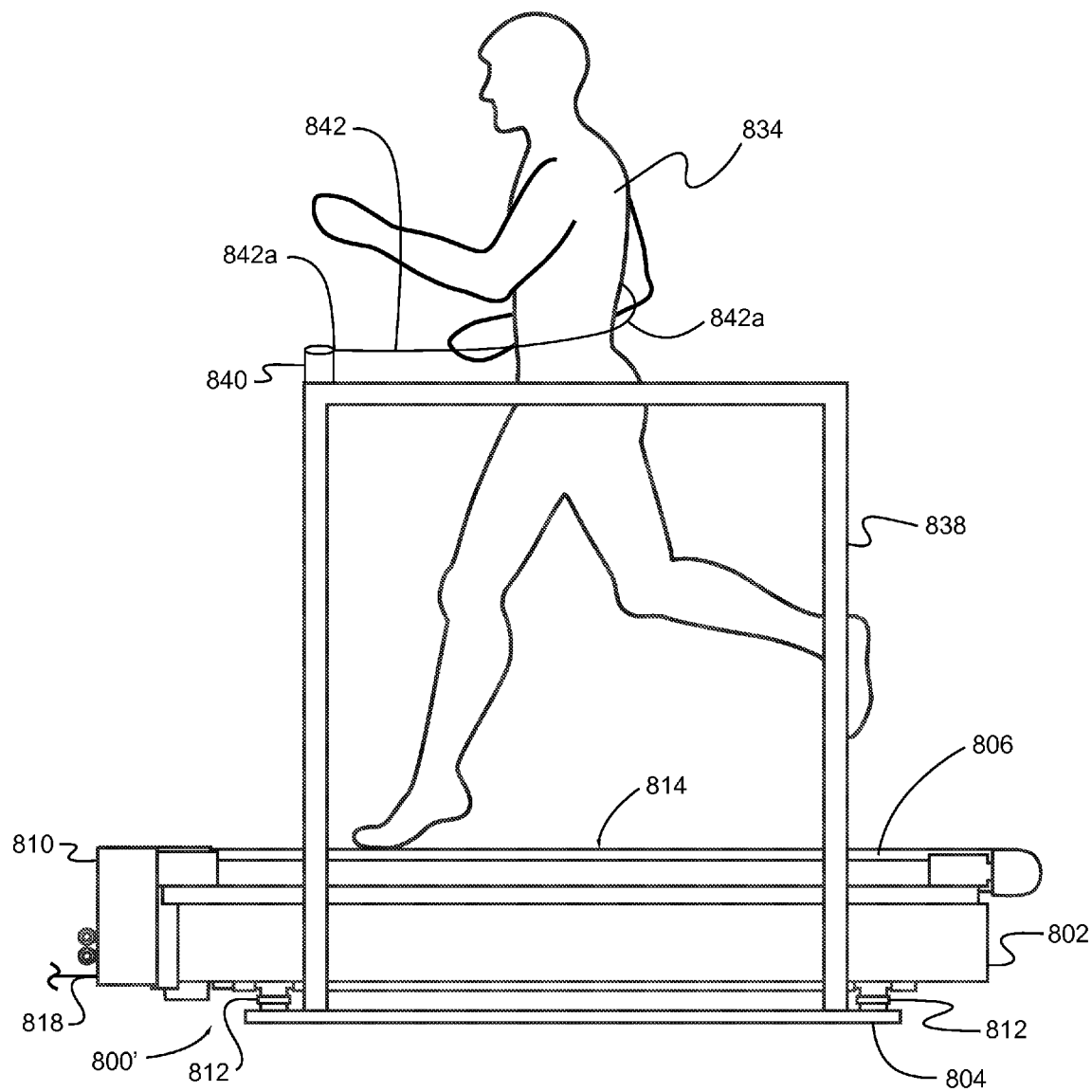
FIG. 34 is a perspective view of a force measurement system with an instrumented treadmill and a position detection device, according to a ninth embodiment of the invention.

As illustrated in the force measurement system 800' of FIG. 34, the instrumented treadmill 802 is provided with a position detection device 840, 842 that is mounted on one of the handrails 838 of the treadmill 802 (e.g., in the center of the front handrail of the treadmill 802). Similar to the instrumented treadmill 802 in FIG. 32, the instrumented treadmill of FIG. 34 comprises left and right rotating belts 806, 808 and four (4) pylon-type force transducers 812 disposed underneath each of the treadmill belt assemblies 806, 808. The position detection device 840, 842 of FIG. 34 detects the position of the body portion of the subject 834 and outputs one or more position data signals that are representative of the position of the body portion of the subject 834. The data acquisition/data processing device 820 is specially programmed to determine the position of the body portion of the subject 834 using the one or more position data signals that are output by the position detection device 840, 842 (e.g., the one or more position data signals from the position detection device 840, 842 may be used to determine the position of the subject 834 relative to the center of the treadmill belts 806, 808 or to approximate the subject's center-of-gravity along the y-axis). Then, by using an equation that is similar to equation (33) above, the speed of the treadmill belts 806, 808 is controlled using the position that is determined for the subject 834.

As shown in FIG. 34, the position detection device 840, 842 comprises a potentiometer or encoder 840 with an elongated attachment member 842 (e.g., a strap, string, or cord) having a first end 842*a* and a second end 842*b*. The potentiometer or encoder 840 comprises a spool about which the elongated attachment member 842 is wrapped around. When a tensile force is applied to the second end 842*b* of the elongated attachment member 842, the elongated attachment member 842 is pulled outwardly from the housing of potentiometer or encoder 840. Conversely, when the tensile force on the elongated attachment member 842 is released, the spool of the potentiometer or encoder 840 is spring-biased (e.g., by using a torsional spring) such that the elongated attachment member 842 is retracted back into the housing of potentiometer or encoder 840. In FIG. 34, it can be seen that the first end 842*a* of the elongated attachment member 842 (e.g., a strap, string, or cord) is operatively coupled to the potentiometer or encoder 840, while the second end 842*b* of the elongated attachment member 842 (e.g., a strap, string, or cord) is attached to the body portion of the subject 834. As such, when the subject's position changes on the treadmill 802 of FIG. 34 (i.e., when the subject moves backwards or forward on the treadmill belts 806, 808), the elongated attachment member 842 of the position detection device 840, 842 either extends out a greater distance from the potentiometer or encoder 840 (i.e., when the subject moves closer to the rear end of the treadmill belts 806, 808) or retracts into the potentiometer or encoder 840 (i.e., when the subject moves closer to the front end of the treadmill belts 806, 808). Thus, based upon the length of the elongated attachment member 842 that is extended out from the housing of potentiometer or encoder 840, the subject's position on the treadmill 802 is determined by the data acquisition/data processing device 820.

While a position detection device 840, 842 comprising a mechanical linkage means is illustrated in the embodiment of FIG. 34, it is to be understood that, in other embodiments of the invention, other suitable types of position detection devices may be utilized to determine the position of the subject 834 on the instrumented treadmill 802. For example, in other embodiments, the position detection device may comprise an infrared or ultrasonic detector with a transmitter portion for emitting an ultrasonic or infrared pulse and a receiver portion for receiving the ultrasonic or infrared pulse after it is reflected off the body portion of the subject.

Now, referring to FIG. 35, still another manner in which the data acquisition/data processing device 820 may determine a position of a body portion (e.g., torso, pelvis, or head) of the subject 834 and control the respective speeds of the treadmill belts 806, 808 using the position determined for the body portion of the subject 834 will be described. In particular, the data acquisition/data processing device 820 may also determine the position of the body portion of the subject 834 by utilizing the inertial measurement units (IMUs) 844 illustrated in FIG. 35. Similar to the instrumented treadmill in FIGS. 32 and 34, the instrumented treadmill of FIG. 35 comprises left and right rotating belts 806, 808 and four (4) pylon-type force transducers 812 disposed underneath each of the treadmill belt assemblies 806, 808.

Figure 35:
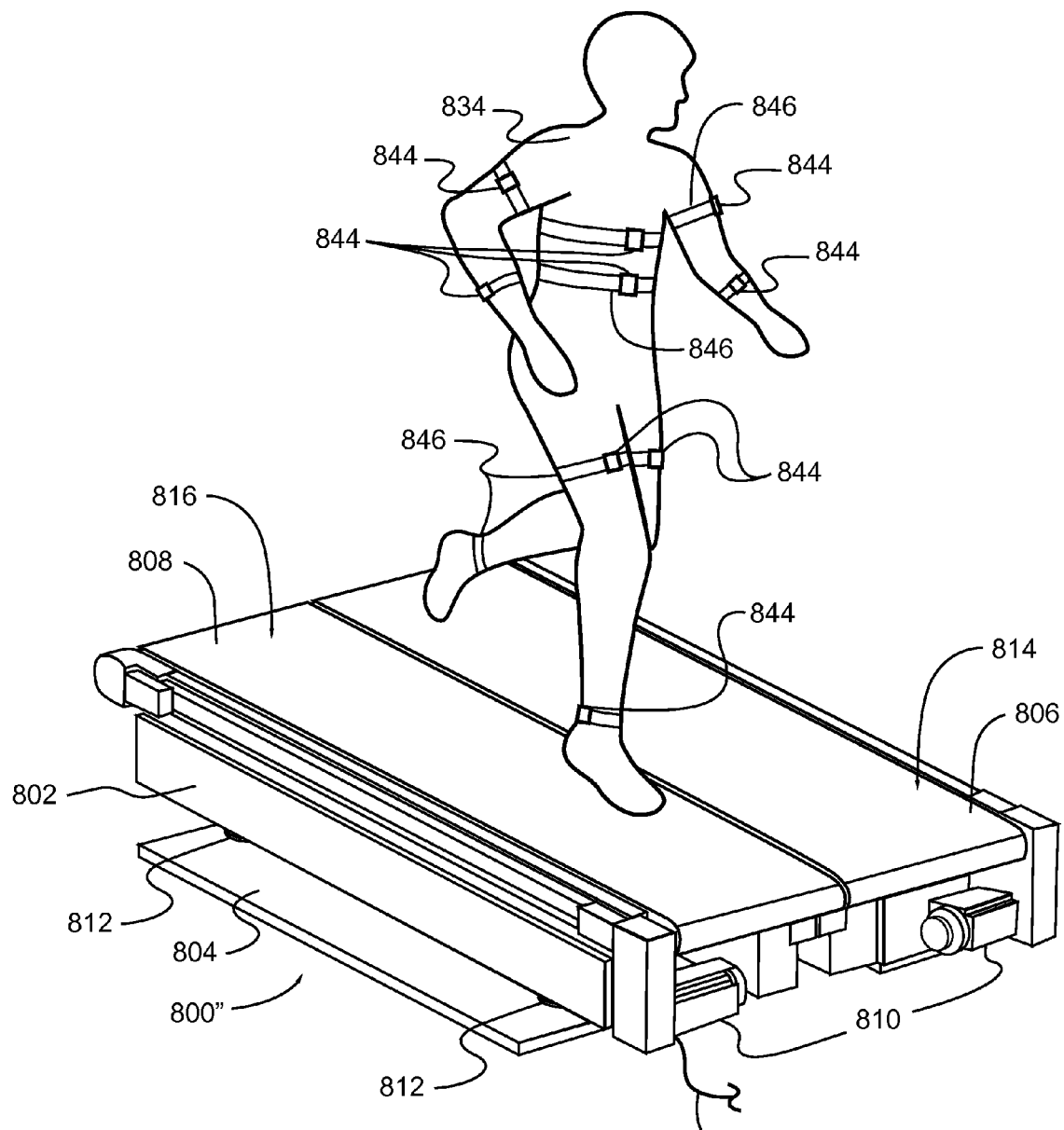
FIG. 35 is a perspective view of a force measurement system with an instrumented treadmill and inertial measurement units (IMUs) disposed on a subject, according to a tenth embodiment of the invention.

As illustrated in the force measurement system 800″ of FIG. 35, a subject 834 may be outfitted with a plurality of different inertial measurement units 844 for detecting motion. In the illustrative embodiment, the subject 834 is provided with two (2) inertial measurement units 844 on each of his legs (e.g., on the side or front of his legs). The subject 834 is also provided with two (2) inertial measurement units 844 on each of his arms (e.g., on the side of his arms). In addition, the subject 834 of FIG. 35 is provided with an inertial measurement unit 844 above his waist, and another inertial measurement unit 844 around his or her chest (e.g., near his sternum). In the illustrated embodiment, each of the inertial measurement units 844 is operatively coupled to the data acquisition/data processing device 820 by wireless means, such as Bluetooth, or another suitable type of personal area network wireless means.

In the illustrated embodiment of FIG. 35, each of the inertial measurement units 844 is coupled to the respective body portion of the subject 834 by a band 846. As shown in FIG. 35, each of the inertial measurement units 844 comprises an IMU housing attached to an elastic band 846. The band 846 is resilient so that it is capable of being stretched while being placed on the subject 834 (e.g., to accommodate the hand or the foot of the subject 834 before it is fitted in place on the arm or the leg of the subject 834). The band 846 can be formed from any suitable stretchable fabric, such as neoprene, spandex, and elastane. Alternatively, the band 846 could be formed from a generally non-stretchable fabric, and be provided with latching means or clasp means for allowing the band 846 to be split into two portions (e.g., the band 846 could be provided with a snap-type latching device).

In other embodiments, it is possible to attach the inertial measurement units 844 to the body portions of the subject 834 using other suitable attachment means. For example, the inertial measurement units 844 may be attached to a surface (e.g., the skin or clothing item) of the subject 834 using adhesive backing means. The adhesive backing means may comprise a removable backing member that is removed just prior to the inertial measurement unit 844 being attached to a subject 834 or object. Also, in some embodiments, the adhesive backing means may comprise a form of double-sided bonding tape that is capable of securely attaching the inertial measurement unit 844 to the subject 834 or another object.

In one or more embodiments, each inertial measurement unit 844 may comprise a triaxial (three-axis) accelerometer sensing linear acceleration $\vec{a}'$, a triaxial (three-axis) rate gyroscope sensing angular velocity $\vec{\omega}'$, a triaxial (three-axis) magnetometer sensing the magnetic north vector $\vec{n}'$, and a central control unit or microprocessor operatively coupled to each of accelerometer, gyroscope, and the magnetometer. In addition, each inertial measurement unit 844 may comprise a wireless data interface for electrically coupling the inertial measurement unit 844 to the data acquisition/data processing device 820.

Next, an illustrative manner in which the data acquisition/data processing device 820 of the force measurement system 800″ performs the inertial measurement unit (IMU) calculations will be explained in detail. In particular, this calculation procedure will describe the manner in which the orientation and position of one or more body portions (e.g., torso or limbs) of a subject 834 could be determined using the signals from the plurality of inertial measurement units (IMUs) 844 of the motion detection system of FIG. 35. As explained above, in one or more embodiments, each inertial measurement unit 844 includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector $\vec{n}'$. Each inertial measurement unit 844 senses in the local (primed) frame of reference attached to the IMU itself. Because each of the sensor devices in each IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the orientation $\vec{\theta}(t)$ and position $\vec{R}(t)$ in the global, unprimed, inertial frame of reference. Initially, the calculation procedure begins with a known initial orientation $\vec{\theta}_0$ and position $\vec{R}_0$ in the global frame of reference.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement units (IMUs) provide calibrated data. In addition, all of the signals from the IMUs are treated as continuous functions of time. Although, it is to be understood the general form of the equations described herein may be readily discretized to account for IMU sensor devices that take discrete time samples from a bandwidth-limited continuous signal.

The orientation $\vec{\theta}(t)$ is obtained by single integration of the angular velocity as follows:

$$\vec{\theta}(t) = \vec{\theta}_0 + \int_0^t \vec{\omega}(t)dt \tag{34}$$

$$\vec{\theta}(t) = \vec{\theta}_0 + \int_0^t \vec{\Theta}(t)\vec{\omega}'(t)dt \tag{35}$$

where $\vec{\Theta}(t)$ is the matrix of the rotation transformation that rotates the instantaneous local frame of reference into the global frame of reference.

The position is obtained by double integration of the linear acceleration in the global reference frame. The triaxial accelerometer of each IMU senses the acceleration $\vec{a}'$ in the local reference frame. The acceleration $\vec{a}'$ has the following contributors: (i) the acceleration due to translational motion, (ii) the acceleration of gravity, and (iii) the centrifugal, Coriolis and Euler acceleration due to rotational motion. All but the first contributor has to be removed as a part of the change of reference frames. The centrifugal and Euler accelerations are zero when the acceleration measurements are taken at the origin of the local reference frame. The first integration gives the linear velocity as follows:

$$\vec{v}(t) = \vec{v}_0 + \int_0^t \{\vec{a}(t) - \vec{g}\} dt \qquad (36)$$

$$\vec{v}(t) = \vec{v}_0 + \int_0^t \{\vec{\Theta}(t)[\vec{a}'(t) + 2\vec{\omega}' \times \vec{v}'(t)] - \vec{g}\} dt \qquad (37)$$

where $2\vec{\omega}' \times \vec{v}'(t)$ is the Coriolis term, and where the local linear velocity is given by the following equation:

$$\vec{v}'(t) = \vec{\Theta}^{-1}(t) \vec{v}(t) \qquad (38)$$

The initial velocity $\vec{v}_0$ can be taken to be zero if the motion is being measured for short periods of time in relation to the duration of Earth's rotation. The second integration gives the position as follows:

$$\vec{R}(t) = \vec{R}_0 + \int_0^t \vec{v}(t) dt \qquad (39)$$

At the initial position, the IMU's local-to-global rotation's matrix has an initial value $\vec{\Theta}(0) = \vec{\Theta}_0$. This value can be derived by knowing the local and global values of both the magnetic north vector and the acceleration of gravity. Those two vectors are usually non-parallel. This is the requirement for the $\vec{\Theta}_0(\vec{g}', \vec{n}', \vec{g}, \vec{n})$ to be unique. The knowledge of either of those vectors in isolation gives a family of non-unique solutions $\vec{\Theta}_0(\vec{g}', \vec{g})$ or $\vec{\Theta}_0(\vec{n}', \vec{n})$ that are unconstrained in one component of rotation. The $\vec{\Theta}_0(\vec{g}', \vec{n}', \vec{g}, \vec{n})$ has many implementations, with the common one being the Kabsch algorithm. As such, using the calculation procedure described above, the data acquisition/data processing device 820 of the force measurement system 800" may determine the orientation $\vec{\theta}(t)$ and position $\vec{R}(t)$ of one or more body portions of the subject 834. For example, the orientation of a limb of the subject 834 (e.g., the right arm of the subject 834 in FIG. 35) may be determined by computing the orientation $\vec{\theta}(t)$ and position $\vec{R}(t)$ of two points on the limb of the subject 834 (i.e., at the respective locations of two inertial measurement units (IMUs) 844 disposed on the limb of the subject 834).

As explained above, the inertial measurement units (IMUs) 844 of FIG. 35 sense measured quantities (i.e., acceleration, angular velocity) that are representative of the position of the body portion of the subject 834 and output a plurality of position data signals that are representative of the position of the body portion of the subject 834. The data acquisition/data processing device 820 is specially programmed to determine the position of the body portion of the subject 834 using the plurality of position data signals that are output by the plurality of inertial measurement units 844 (e.g., the plurality of position data signals from the inertial measurement units 844 may be used to determine the position of the subject 834 relative to the center of the treadmill belts 806, 808 or to approximate the subject's center-of-gravity along the y-axis). Then, by using an equation that is similar to equation (33) above, the speed of the treadmill belts 806, 808 is controlled using the position that is determined for the subject 834.

In one or more further embodiments, the data acquisition/data processing device 820 is specially programmed to monitor the determined position of the body portion of the subject 834, and to provide biofeedback to the subject 834 based upon the monitored position of the body portion of the subject 834. For example, if the subject 834 is getting too close to the rear end of treadmill 802 such that he or she may fall from the treadmill 802, the data acquisition/data processing device 820 may be specially programmed to generate and send a warning signal to a visual warning device (e.g., a flashing light) and/or to an audible warning device (e.g., a loud alarm) that informs the subject 834 that he or she is getting too close to the rear end of the treadmill 802. A similar warning may be generated by the data acquisition/data processing device 820 when the subject 834 is determined to be too close to the front end of the treadmill 802. For example, a computed distance between the subject 834 and either the front end or rear end of the treadmill 802 may be compared to a threshold distance between the subject 834 and either the front end or rear end of the treadmill 802 (e.g., if the subject is closer than 2 feet from the rear end of the treadmill 802, the alarm is sounded).

Figure 36:
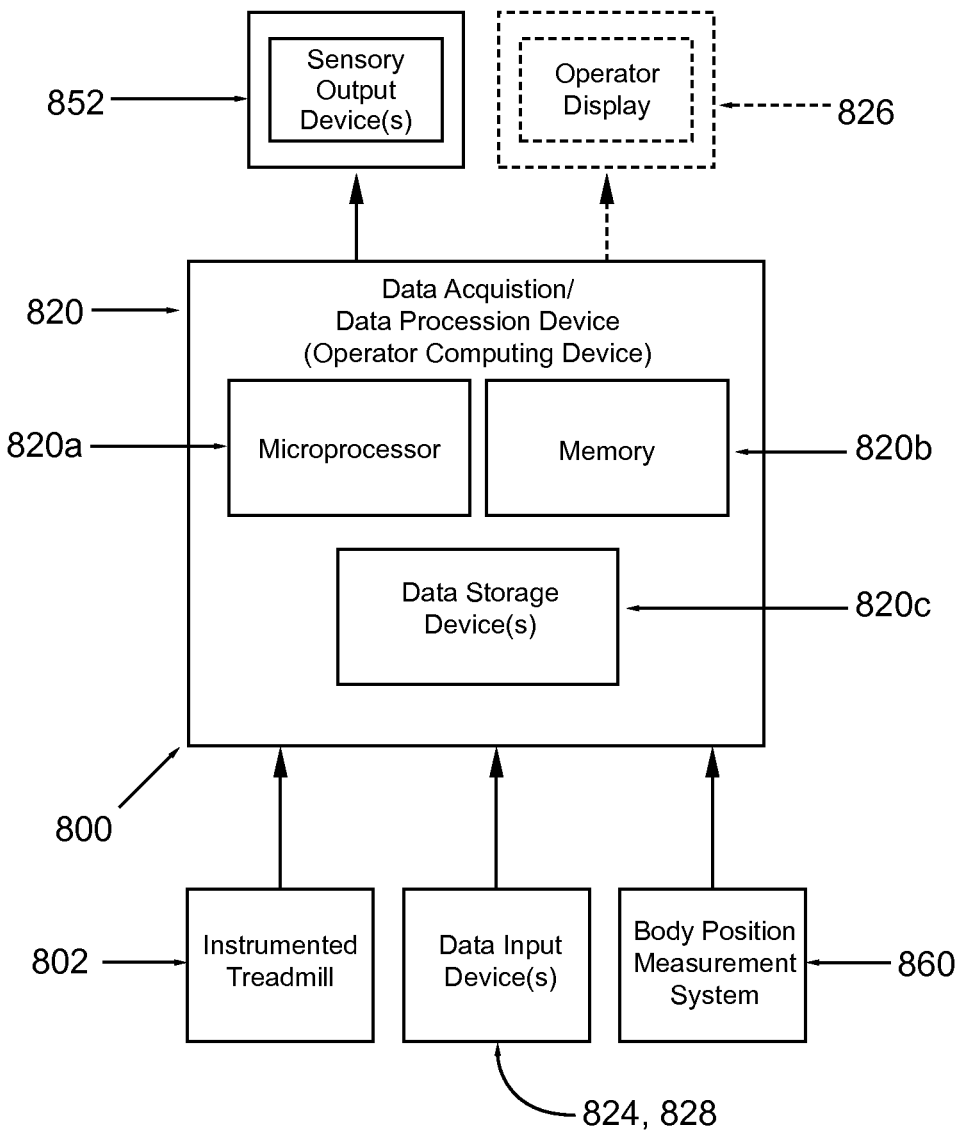
FIG. 36 is a block diagram of constituent components of the force measurement system with the instrumented treadmill of FIG. 32, according to the eighth embodiment of the invention.

In yet one or more further embodiments, the force measurement system 800 that includes the instrumented treadmill 802 operatively coupled to the data acquisition/data processing device 820 may further comprise one or more sensory output devices 852 operatively coupled to the data acquisition/data processing device 820 for providing biofeedback to a subject disposed on the instrumented treadmill 802 (refer to FIG. 36). In this embodiment, each of the one or more sensory output devices 852 is configured to receive a sensory output signal from the data acquisition/data processing device 820, to generate at least one of a visual indicator, an audible indicator, and a tactile indicator that is based upon the sensory output signal, and to output the at least one of the visual indicator, the audible indicator, and the tactile indicator to the subject in order to provide biofeedback as to conformity of one or more gait parameters of the subject to one or more respective baseline values or biofeedback as to conformity of a first of the one or more gait parameters of the subject to a second of the one or more gait parameters of the subject.

Figure 37:
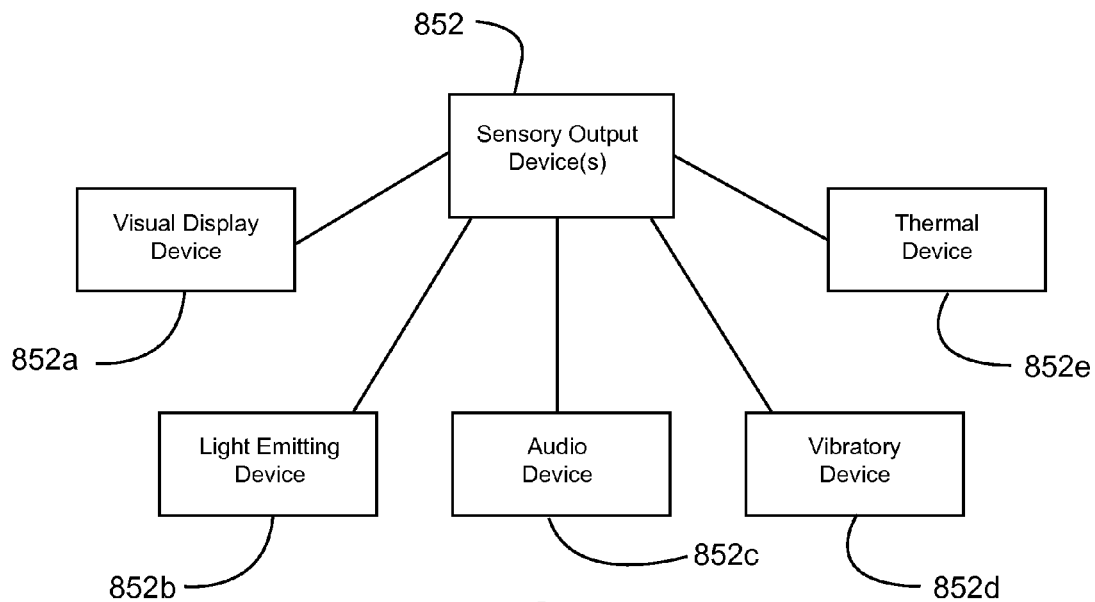
FIG. 37 illustrates various forms in which sensory output device(s) of the exemplary force measurement system with biofeedback may be embodied, according to an embodiment of the invention.

Thus, the one or more sensory output devices 852 provide sensory stimuli to the subject so as to enable the force measurement system 800 to provide the subject with biofeedback regarding his or her gait on the instrumented treadmill 802. In particular, with reference to FIG. 37, the one or more sensory output devices 852 may comprise a visual display device 852a for displaying one or more images to the subject, a light emitting device 852b for providing a visual cue to the subject, an audio device 852c for delivering an audible cue to the subject or user, a vibratory device 852d for delivering vibrations to the limb or torso of the subject (i.e., a first type of tactile sensor output device), and a thermal or heat-based device 852e for delivering heat to the skin of the subject (i.e., a second type of tactile sensor output device). It is to be understood that the system 800 may comprise any number or all of these sensory output devices 852a, 852b, 852c, 852d, 852e depending on the type(s) of biofeedback that needs to be delivered by the system 800.

When at least one of the one or more the sensory output devices 852 is in the form of a visual display device 852a, the visual display device 852a may comprise an output screen for displaying one or more images to the subject disposed on the instrumented treadmill 802. For example, as shown in FIG. 32, the visual display device 852a may be in the form of a flat panel monitor. The flat screen monitor of FIG. 32 may comprise a liquid crystal display (i.e., an LCD display), a light-emitting diode display (i.e., an LED display), a plasma display, a projection-type display, or a rear projection-type display. Those of ordinary skill in the art will readily appreciate that various types of visual display devices 852a may be operatively coupled to the data acquisition/data processing device 820 via an electrical data cable 858, or by means of a wireless data transmission means. Electrical power may be supplied to the visual display device 852a using a separate power cord that connects to a building wall receptacle.

As shown in FIG. 32, the visual display device 852a is configured to generate one or more visual indicators 854, 856 that provide biofeedback to the subject as to conformity of the one or more gait parameters of the subject to the one or more respective baseline values or biofeedback as to conformity of the first of the one or more gait parameters of the subject to the second of the one or more gait parameters of the subject. For example, in FIG. 32, it can be seen that the visual display device 852a comprises a first visual indicator bar 854 for indicating the left step length of the subject disposed on the instrumented treadmill 802 and a second visual indicator bar 856 for indicating the right step length of the subject disposed on the instrumented treadmill 802. Thus, by virtue of the first and second visual indicator bars 854, 856, the subject is capable of readily ascertaining whether or not the step length of each of his or her legs is generally equal to one another, or substantially different from one another.

When at least one of the one or more the sensory output devices 852 is in the form of a light emitting device 852b, the light emitting device 852b may comprise one or more flashing lights that provide biofeedback to the subject disposed on the instrumented treadmill 802. In particular, the light emitting device 852b may be configured to generate one or more visual indicators (i.e., flashing lights) that provide biofeedback to the subject as to conformity of the one or more gait parameters of the subject to the one or more respective baseline values or biofeedback as to conformity of the first of the one or more gait parameters of the subject to the second of the one or more gait parameters of the subject.

When at least one of the one or more the sensory output devices 852 is in the form of an audio device 852c, the audio device 852c may comprise an audio headset configured to be worn on a head of the subject or a speaker disposed on, or proximate to the instrumented treadmill 802. The audio headset or speaker may be configured to generate an audible indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

When at least one of the one or more the sensory output devices 852 is in the form of a vibratory device 852d, the vibratory device 852d may comprise a housing containing a small motor with an off-center weight that is configured to be worn by the subject. The vibratory device 852d may be configured to generate a vibratory tactile indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

When at least one of the one or more the sensory output devices 852 is in the form of a thermal device 852e, the thermal device 852e may comprise a housing containing a small electrical resistance heating element or Peltier heating element that is configured to be worn by the subject. The thermal device 852e may be configured to generate a thermal tactile indicator that provides biofeedback to the subject as to conformity of the one or more gait parameters of the subject to the one or more respective baseline values or biofeedback as to conformity of the first of the one or more gait parameters of the subject to the second of the one or more gait parameters of the subject.

Figure 38:
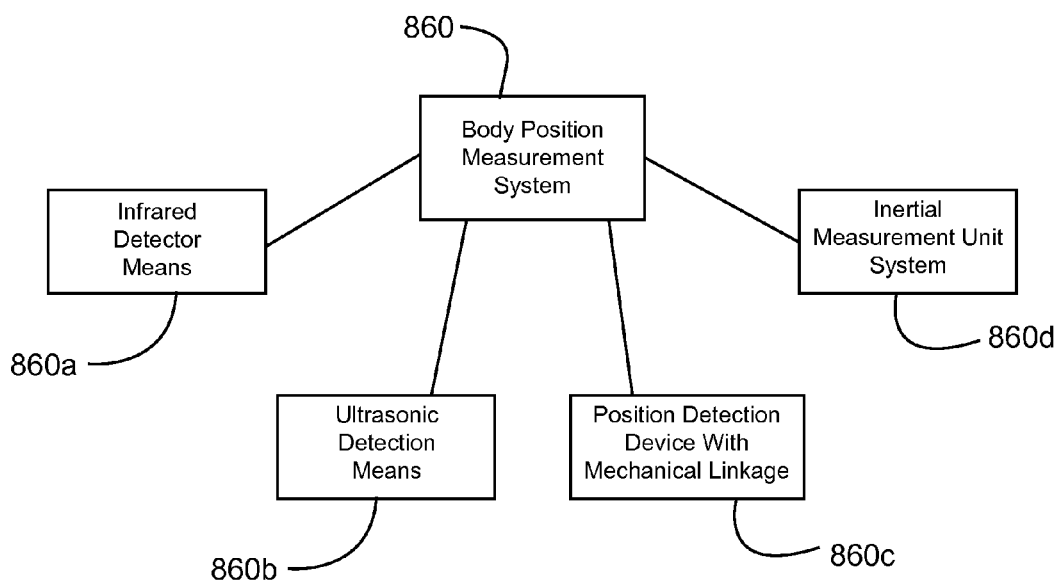
FIG. 38 illustrates various forms in which the body position measurement system of the exemplary force measurement system with biofeedback may be embodied, according to an embodiment of the invention.

In still one or more further embodiments, the force measurement system 800 that includes the instrumented treadmill 802, the data acquisition/data processing device 820, and the one or more sensory output devices 852 further includes a body position measurement system 860 (refer to FIG. 36). The body position measurement system is configured to detect the position of an upper body portion of the subject and output one or more position data signals that are representative of the position of the upper body portion of the subject. In one or more embodiments, the upper body portion of the subject is disposed above the feet of the subject. In particular, with reference to FIG. 38, the body position measurement system 860 may comprise at least one of an infrared detection means 860a (e.g., an infrared detector with a transmitter device for emitting an infrared pulse and a receiver device for receiving the infrared pulse after it is reflected off the body portion of the subject), an ultrasonic detection means 860b (e.g., an ultrasonic detector with a transmitter device for emitting an ultrasonic pulse and a receiver device for receiving the ultrasonic pulse after it is reflected off the body portion of the subject), a position detection device with mechanical linkage means 860c (e.g., as described above with regard to FIG. 34), and an inertial measurement system 860d utilizing one or more inertial measurement units (IMUs) 844 configured to be coupled to the upper body portion of the subject (e.g., as described above with regard to FIG. 35). It is to be understood that the system 800 may comprise any number or all of these body position measurement systems 860a, 860b, 860c, 860d depending on the type(s) of measurements that need to be performed by the system 800.

Figure 40:
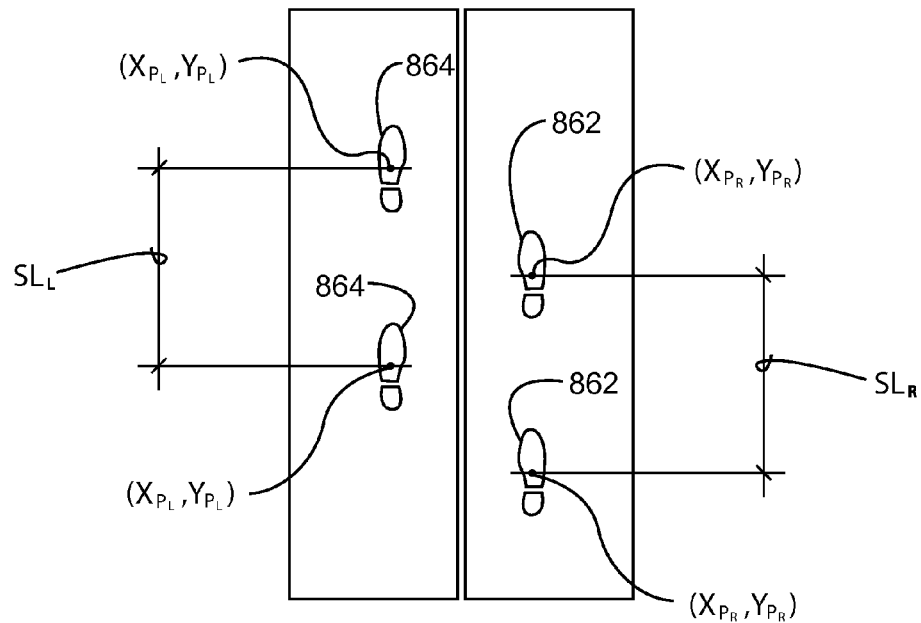
FIG. 40 is a top view of unrolled instrumented treadmill belts that illustrate the manner in which the right and left step lengths for a subject may be determined, according an embodiment of the invention.

In this further embodiment, wherein biofeedback is provided to the subject disposed on the instrumented treadmill 802, the data acquisition/data processing device 820 of the system 800 is specially programmed to determine one or more gait parameters for the subject from the output load components (e.g., from the measured forces and moments). The one or more gait parameters determined for the subject may comprise at least one of the following: (i) a step length of the subject, (ii) a maximum sway range of a center of pressure (COP) of the subject (i.e., anterior-posterior sway or lateral sway of the COP), (iii) a maximum sway range of the center of gravity (GOG) of the subject (i.e., anterior-posterior sway or lateral sway of the COG), (iv) a time duration of a single leg stance of the subject, and (v) a time duration of a single leg swing of the subject. For example, with reference to FIG. 40, the data acquisition/data processing device 820 may determine the left step length $SL_L$ of the subject by computing the distance between the center of pressure $COP_L$ for the left foot 864 of the subject at time $t_1$ and the center of pressure $COP_L$ for the left foot 864 of the subject at time $t_2$. Similarly, as shown in FIG. 40, the data acquisition/data processing device 820 may determine the right step length $SL_R$ of the subject by computing the distance between the center of pressure $COP_R$ for the right foot 862 of the subject at time $t_1$ and the center of pressure $COP_R$ for the right foot 862 of the subject at time $t_2$. As explained above, the center of pressure ($COP_R$) coordinates ($X_{P_R}$, $Y_{P_R}$) for the right foot 862 of the subject are determined from the load components exerted on the right belt surface 816 of the right treadmill belt assembly 808 (i.e., a right displaceable component) by the right foot 862 of the subject, whereas the center of pressure ($COP_L$) coordinates ($X_{P_L}$, $Y_{P_L}$) for the left foot 864 of the subject are determined from the load components exerted on the left belt surface 814 of the left treadmill belt assembly 806 (i.e., a left displaceable component) by the left foot 864 of the subject. Alternatively, rather than computing the right and left step lengths $SL_R$, $SL_L$ using the center points of each foot 862, 864, the right and left step lengths $SL_R$, $SL_L$ may be computed using the heel point of each foot 862, 864 or the toe point of each foot.

Figure 39:
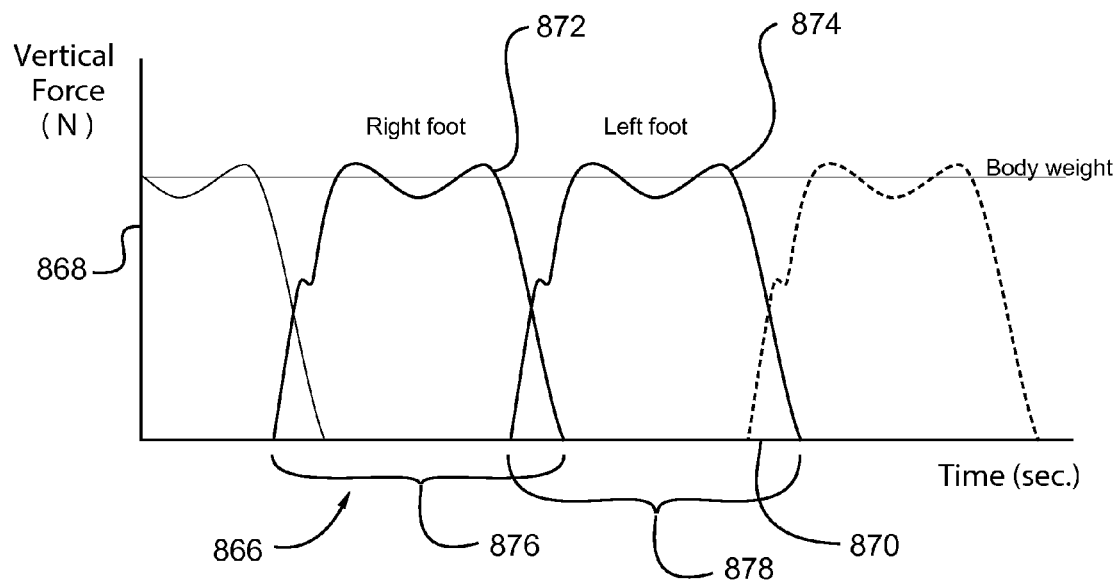
FIG. 39 is a graph illustrating a time duration and a magnitude of a vertical force being separately applied by a right foot and a left foot of a subject during a gait cycle.

As another example, referring to FIG. 39, the manner in which the time durations of the single leg stances of the subject are computed by the data acquisition/data processing device 820 will be explained. FIG. 39 is a graphical illustration of force curves corresponding to the right and left foot of the subject. In FIG. 39, the separate vertical forces ($F_z$) being applied by the subject's feet are plotted as function of time. As such, the y-axis 868 of the graph 866 of FIG. 39 corresponds to the vertical force (e.g., in Newtons), and the x-axis 870 of the graph 866 of FIG. 39 corresponds to time (e.g., in seconds). The curve 872 in FIG. 39 illustrates the vertical force generated by the right foot 862 of the subject on the right belt surface 816 of the right treadmill belt assembly 808, while the curve 874 in FIG. 39 illustrates the vertical force generated by the left foot of the subject on the left belt surface 814 of the left treadmill belt assembly 806 by the left foot 864 of the subject (i.e., the left and right treadmill belt assemblies 806, 808 of the instrumented treadmill 802). Thus, referring to FIG. 39, the time duration of the right leg stance of the subject is the time duration 876 determined from the base of the right foot curve 872, whereas the time duration of the left leg stance of the subject is the time duration 878 determined from the base of the left foot curve 874. As such, FIG. 39 enables the time durations of the right and left leg stances of the subject to be compared to one another by the data acquisition/data processing device 820.

In this further embodiment, the data acquisition/data processing device 820 is also specially programmed so as to enable a system user (e.g., a clinician or subject) to selectively choose the gait parameters that are analyzed for a particular subject during the testing of the subject (i.e., the data acquisition/data processing device 820 is provided with various setup options that allow the system user to determine which gait parameters are to be analyzed during the testing). For example, the data acquisition/data processing device 820 may be specially programmed so as to allow the system user to choose among the following parameters: (i) a step length of the subject, (ii) a maximum sway range of a center of pressure of the subject, (iii) a maximum sway range of the center of gravity of the subject, (iv) a time duration of a single leg stance of the subject, and (v) a time duration of a single leg swing of the subject, or to choose among other gait parameters available in the system 800. As such, the system 800 allows the various gait parameters to be interchangeably used during subject testing, thus enabling the testing to be specifically tailored for a specific subject having a specific disability or disease.

Figure 42:
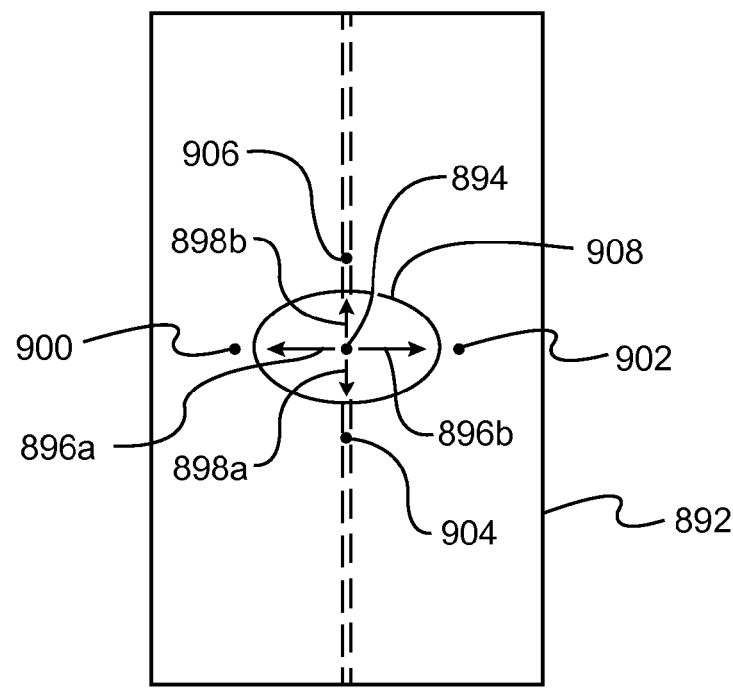
FIG. 42 is a top view of a virtual measurement surface of the instrumented treadmill of the force measurement system that illustrates the manner in which the anterior-posterior sway and lateral sway of the subject is compared to baseline value(s), according an embodiment of the invention.

With reference to FIG. 42, the manner in which the maximum sway range of a center of pressure of the subject may be determined by the data acquisition/data processing device 820 will be explained. In FIG. 42, a top view of a virtual force measurement surface 892 of the instrumented treadmill 802 is illustrated, wherein the two separate belt measurement surfaces 814, 816 have been combined to form an overall measurement surface. As depicted in FIG. 42, the centers of pressure for the right and left feet of the subject have been mathematically combined in order to result in an overall center of pressure 894 for the subject on the virtual force measurement surface 892. The maximum sway range for the subject may be determined in lateral sway directions 896a, 896b, posterior-anterior sway directions 898a, 898b, or in both lateral and posterior-anterior sway directions 896a, 896b, 898a, 898b. In FIG. 42, the subject's maximum left lateral sway is represented by the point 900, while the subject's maximum right lateral sway is represented by the point 902. As such, the maximum lateral sway range of the center of pressure for the subject is computed by the data acquisition/data processing device 820 by determining the distance between the lateral sway range points 900, 902. Similarly, the subject's maximum posterior sway is represented by the point 904, while the subject's maximum anterior sway is represented by the point 906. Thus, the maximum posterior-anterior sway range of the center of pressure for the subject is computed by the data acquisition/data processing device 820 by determining the distance between the posterior-anterior sway range points 904, 906. Referring again to FIG. 42, it can be seen that the subject's maximum lateral sway range of the center of pressure and the subject's maximum posterior-anterior sway range of the center of pressure lies outside of the elliptical baseline 908 that is based upon data for a normative population of subjects (i.e., for a population of subjects without gait disabilities). Consequently, for the exemplary embodiment illustrated in FIG. 42, the subject's maximum lateral and posterior-anterior center of pressure sway ranges are higher than that of the normative population baseline data.

In another embodiment, rather than comparing the maximum sway range of the center of pressure of the subject to the baseline normative data, the maximum sway range of the center of gravity of the subject may be compared to baseline normative data by the data acquisition/data processing device 820. Initially, the center of gravity (COG) for the subject may be determined using one of the body position measurement systems 860 described above, or by using the computation method described above. After which, sway angle may be computed by the data acquisition/data processing device 820 by using the following equation:

$$\theta = \sin^{-1}\left(\frac{COG}{0.55h}\right) - 2.3° \quad (40)$$

where:
θ: sway angle of the subject;
COG: center of gravity of the subject; and
h: height of the center of gravity of the subject
Then, the maximum lateral sway range of the center of gravity for the subject may be computed by the data acquisition/data processing device 820 by determining the angular range between the maximum left sway angle and maximum right sway angle. Similarly, the maximum posterior-anterior sway range of the center of gravity for the subject may be computed by the data acquisition/data processing device 820 by determining the angular range between the maximum posterior sway angle and maximum anterior sway angle.

In this further embodiment, the data acquisition/data processing device 820 of the system 800 is further specially programmed to compare the one or more gait parameters determined for the subject to one or more respective baseline values in order to determine gait deviations from a normal standard. In addition, the data acquisition/data processing device 820 is specially programmed to determine how closely the one or more gait parameters determined for the subject conform to the one or more respective baseline values, and to generate the sensory output signal based upon the conformity of the one or more gait parameters of the subject to the one or more respective baseline values so as to provide biofeedback indicative of the gait deviations from the normal standard.

In an exemplary embodiment, when auditory feedback is given to the subject, the amplitude of the sound delivered to the subject may be adjusted based upon the conformity of one or more gait parameters determined for the subject to one or more respective baseline values. Initially, a gait parameter determined for the subject (e.g., the maximum lateral sway range of the center of pressure of the subject) is compared to a baseline value (e.g., a normative population baseline value for maximum lateral sway range) by the data acquisition/data processing device 820. Then, the data acquisition/data processing device 820 determines how closely the gait parameter determined for the subject (e.g., the maximum lateral sway range of the center of pressure of the subject) conforms to the baseline value (e.g., a normative population baseline value for maximum lateral sway range). For example, for a series of successive gait cycles, the maximum lateral sway range of the center of pressure of the subject may gradually decrease over time from an initial time $t_i$ to a final time $t_f$ so that the discrepancy between the maximum lateral sway range of the center of pressure of the subject and the normative population baseline value for maximum lateral sway range gradually decreases over time. As such, the magnitude of the sensory output signal generated by the data acquisition/data processing device 820 based upon the conformity of the maximum lateral sway range of the center of pressure of the subject may steadily decrease in magnitude over time during the successive gait cycles (i.e., the magnitude of the signal is smaller for time $t_f$ as compared time $t_i$). Consequently, when the sensory output device is in the form of an audio headset or speaker(s), the amplitude or loudness of the sound generated by the audio headset or speaker(s) is proportional to the sensory output signal received by the audio headset or speaker(s). That is, for this particular example, the sound is the loudest for the first gait cycle in the series of successive gait cycles (i.e., at time $t_i$), and the sound is the softest for the final gait cycle in the series of successive gait cycles (i.e., at time $t_f$). Thus, in general, the larger the discrepancy between the maximum lateral sway range of the center of pressure of the subject and the normative population baseline value for maximum lateral sway range, the louder the sound that is emitted by the audio headset or speaker(s) as biofeedback to the subject (i.e., the higher the amplitude of the sound). Conversely, the smaller the discrepancy between the maximum lateral sway range of the center of pressure of the subject and the normative population baseline value for maximum lateral sway range, the softer the sound that is emitted by the audio headset or speaker(s) as biofeedback to the subject (i.e., the lower the amplitude of the sound). Rather than modulating the loudness or the amplitude of the sound in accordance with the discrepancy between the maximum lateral sway range of the center of pressure of the subject and the normative population baseline value for maximum lateral sway range, the pitch or frequency may also be varied based upon the discrepancy between the maximum lateral sway range of the center of pressure of the subject and the normative population baseline value for maximum lateral sway range. That is, in general, the larger the discrepancy between the maximum lateral sway range of the center of pressure of the subject and the normative population baseline value, the higher the frequency of the sound that is emitted by the audio headset or speaker(s) as biofeedback to the subject (i.e., the higher the pitch of the sound). Conversely, the smaller the discrepancy between the maximum lateral sway range of the center of pressure of the subject and the normative population baseline value, the lower the frequency of the sound that is emitted by the audio headset or speaker(s) as biofeedback to the subject (i.e., the lower the frequency of the sound). In the above examples, when the maximum lateral sway range of the center of pressure of the subject and the normative population baseline value are generally equal to one another, there may be no sound emitted by the audio headset or speaker(s), or in other words, the amplitude of the sound may be zero.

Also, in this further embodiment, the data acquisition/data processing device 820 of the system 800 may be specially programmed to compare a first of the one or more gait parameters for the subject to a second of the one or more gait parameters for the subject in order to determine asymmetry between a right leg and a left leg of the subject. Further, the data acquisition/data processing device 820 may be specially programmed to determine how closely the first of the one or more gait parameters for the subject conforms to the second of the one or more gait parameters for the subject, and to generate the sensory output signal based upon the conformity of the first of the one or more gait parameters of the subject to the second of the one or more gait parameters of the subject so as to provide biofeedback indicative of the asymmetry between a right leg and a left leg of the subject. For example, if the first of the one or more gait parameters is the left step length $SL_L$ of the subject and the second of the one or more gait parameters is the right step length $SL_R$ of the subject (as explained above with regard to FIG. 40), upon comparing the left and right step lengths $SL_L$, $SL_R$, the data acquisition/data processing device 820 may determine that the left step length of the subject is greater than the right step length of the subject. As such, the data acquisition/data processing device 820 may determine that there is step length asymmetry between the right and left legs of the subject. In order to provide biofeedback to the subject regarding his or her asymmetry in step length, the data acquisition/data processing device 820 may generate a first visual indicator bar 854 on the visual display device 852a for the left step length, and may generate a second visual indicator bar 856 on the visual display device 852a for the right step length (as described above with regard to FIG. 32). As shown in FIG. 32, the first visual indicator bar 854 corresponding to the left step length of the subject is taller than the second visual indicator bar 856 corresponding to the right step length of the subject, which provides graphical biofeedback to the subject on the instrumented treadmill 802 that is indicative of the asymmetry in step length between his or her right and leg legs. The height difference between the first and second visual indicator bars 854, 856 is indicative of how closely the left and right step lengths correspond to one another. That is, the larger the difference in height between the first and second visual indicator bars 854, 856, the larger the amount of asymmetry that exists between the right and left legs of the subject. In this illustrative example, wherein the sensory output device is in the form of the visual display device 852a, the sensory output signal is delivered from the data acquisition/data processing device 820 to the visual display device 852a.

While the first and second visual indicator bars 854, 856 of FIG. 32 represent a particular snapshot in time, the data acquisition/data processing device 820 is specially programmed to dynamically update the screen image on the visual display device 852a so that biofeedback of the subject's performance is provided to the subject in real-time. As such, the subject is able to follow his or her performance while he or she runs or walks on the treadmill 802. Advantageously, dynamically updating the biofeedback provided to the subject disposed on the treadmill 802 allows the subject to follow his or her performance, and make improvements during the course of the testing or training routine. Because the gait parameters being analyzed and displayed to the subject rapidly change over time, the gait parameters being may be time-averaged, and the time-averaged gait parameter values may be displayed to the subject on the visual display device 852a. For example, a plurality of left step lengths over a particular time period may be averaged for a subject, and then compared to a plurality of right step lengths that are time-averaged for the subject.

In this further embodiment, the first and second of the one or more gait parameters determined for the subject by the data acquisition/data processing device 820 may comprise at least one of: (i) first and second time durations for respective right and left leg stance phases of the subject; (ii) first and second time durations for respective right and left leg swing phases of the subject; (iii) first and second step lengths for the respective right and left legs of the subject (as explained above with regard to FIG. 40); and (iv) first and second ground reaction forces for the respective right and left legs of the subject ($F_{z_L}$, $F_{z_R}$). For example, with reference to FIG. 39, the data acquisition/data processing device 820 may be specially programmed to compare the time duration 876 of the right leg stance of the subject to the time duration 878 of the left leg stance of the subject. In the exemplary embodiment of FIG. 39, the time duration 876 of the right leg stance of the subject is generally equal to the time duration 878 of the left leg stance of the subject. As such, the exemplary data in FIG. 39 indicates that the subject's legs are generally symmetrical with regard to this measured gait parameter.

Figure 41:
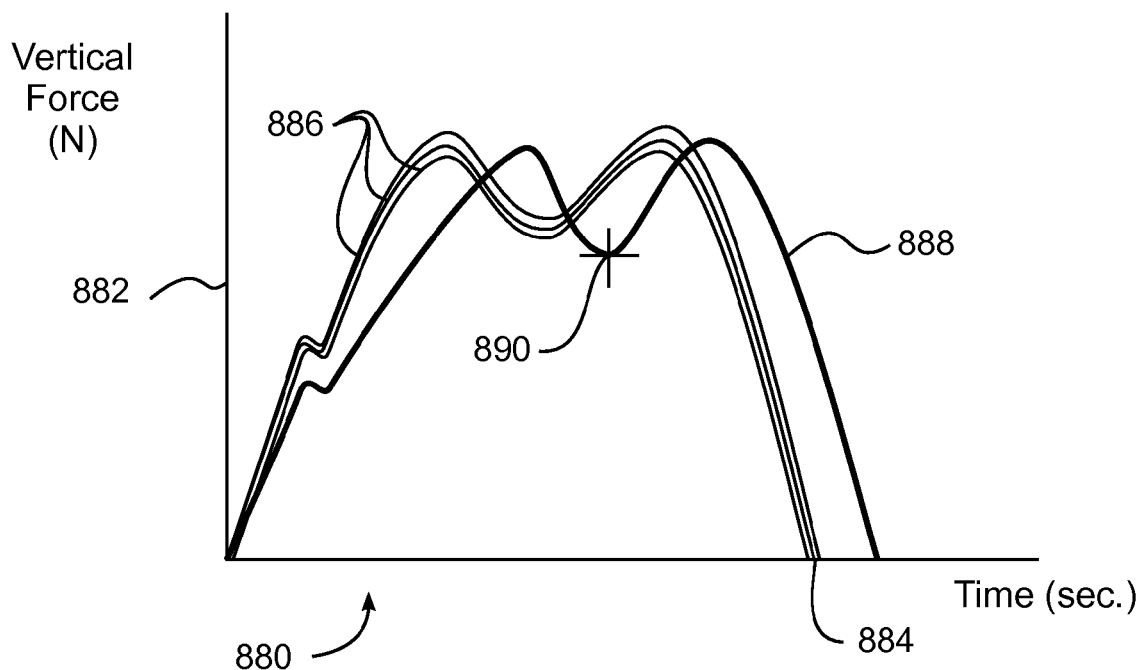
FIG. 41 is another graph illustrating vertical force curves for a right foot and a left foot of a subject being superimposed on one another so that the forces curves may be readily compared to one another so as to provide biofeedback to the subject, according an embodiment of the invention.

Similar to that described above with regard to FIG. 32, while the leg stance time duration curves 872, 874 in FIG. 39 represent a particular snapshot in time, the data acquisition/data processing device 820 is specially programmed to dynamically update the screen image on the visual display device 852a so that biofeedback of the subject's performance is provided to the subject in real-time. For example, referring to FIG. 41, the data acquisition/data processing device 820 may be specially programmed to generate the graphical output 880 depicted in this figure. Similar to FIG. 39, the separate vertical forces ($F_z$) being applied by the subject's feet are plotted as function of time. As such, the y-axis 882 of the graph 880 of FIG. 41 corresponds to the vertical force (e.g., in Newtons), and the x-axis 884 of the graph 880 of FIG. 41 corresponds to time (e.g., in seconds). The superimposed curves 886 in FIG. 41 illustrate vertical force curves generated by the right foot 862 of the subject on the right belt surface 816 of the right treadmill belt assembly 808, while the curve 888 in FIG. 41 illustrates the vertical force generated by the left foot of the subject on the left belt surface 814 of the left treadmill belt assembly 806 by the left foot 864 of the subject (i.e., the left and right treadmill belt assemblies 806, 808 of the instrumented treadmill 802). That is, as the subject walks or runs on the treadmill 802, the curves 886 for the stance phase of the subject's right foot are continuously superimposed on one another, while the curve 888 for the stance phase of the subject's left foot is superimposed on the top of the curves 886 for the stance phase of the subject's right foot. Thus, the subject is able to readily discern whether or not the stance phase for his or right leg generally conforms to the stance phase for his or her left leg. In addition, as shown in FIG. 41, the data acquisition/data processing device 820 may generate a cursor or marker 890 on the output screen of the visual display device 852a that follows the path of the curve 888 corresponding to the right foot 862 of the subject over time so that a subject is able to readily ascertain the progression of his or her gait cycle.

As another example, when auditory feedback is given to the subject, rather than visual feedback, the amplitude of the sound delivered to the subject may be adjusted based upon the conformity of the first gait parameter of the subject to the second gait parameter of the subject. Initially, the first gait parameter (e.g., the time duration of the right leg stance of the subject) is compared to the second gait parameter (e.g., the time duration of the left leg stance of the subject) by the data acquisition/data processing device 820. Then, the data acquisition/data processing device 820 determines how closely the first gait parameter (e.g., the time duration of the right leg stance of the subject) conforms to the second gait parameter (e.g., the time duration of the left leg stance of the subject). For example, for a series of four successive gait cycles, the time duration of the right leg stance of the subject may be $t_1$, $t_2$, $t_3$, and $t_4$ seconds greater than the time duration of the left leg stance of the subject, where time duration difference $t_4$ is greater than $t_3$, $t_3$ is greater than $t_2$, and $t_2$ is greater than $t_1$. As such, the magnitude of the sensory output signal generated by the data acquisition/data processing device 820 based upon the conformity of the first and second gait parameters of the subject may be successively greater for $t_1$, $t_2$, $t_3$, and $t_4$ (i.e., the magnitude of the signal is larger for $t_4$ as compared $t_3$, it is larger for $t_3$ as compared $t_2$, etc.). Consequently, when the sensory output device is in the form of an audio headset or speaker(s), the amplitude or loudness of the sound generated by the audio headset or speaker(s) is proportional to the sensory output signal received by the audio headset or speaker(s). That is, for this particular example, the sound is the loudest for the last gait cycle in the four successive gait cycles (i.e., for the last gait cycle, wherein the time duration difference between the right leg stance of the subject and the time duration of the left leg stance of the subject is $t_4$). Thus, in general, the larger the discrepancy between the first and second gait parameters (e.g., the time durations of the right and left leg stances of the subject), the louder the sound that is emitted by the audio headset or speaker(s) as biofeedback to the subject (i.e., the higher the amplitude of the sound). Conversely, the smaller the discrepancy between the first and second gait parameters (e.g., the time durations of the right and left leg stances of the subject), the softer the sound that is emitted by the audio headset or speaker(s) as biofeedback to the subject (i.e., the lower the amplitude of the sound). Rather than modulating the loudness or the amplitude of the sound in accordance with the discrepancy between the first and second gait parameters (e.g., the time durations of the right and left leg stances of the subject), the pitch or frequency may also be varied based upon the discrepancy between the first and second gait parameters. That is, in general, the larger the discrepancy between the first and second gait parameters (e.g., the time durations of the right and left leg stances of the subject), the higher the frequency of the sound that is emitted by the audio headset or speaker(s) as biofeedback to the subject (i.e., the higher the pitch of the sound). Conversely, the smaller the discrepancy between the first and second gait parameters (e.g., the time durations of the right and left leg stances of the subject), the lower the frequency of the sound that is emitted by the audio headset or speaker(s) as biofeedback to the subject (i.e., the lower the frequency of the sound). In the above examples, when the legs of the subject are symmetrical, or substantially symmetrical to one another (e.g., when the time durations of the right and left leg stances of the subject are generally equal to one another), there may be no sound emitted by the audio headset or speaker(s), or in other words, the amplitude of the sound may be zero.

In yet a further embodiment, the force measurement system 800 is configured to provide biofeedback to the subject based upon both the output of the force transducers 812 of the instrumented treadmill 802 and the output of the body position measurement system 860. In this further embodiment, the one or more gait parameters that the data acquisition/data processing device 820 is configured to determine from the load signals of the force transducers 812 of the instrumented treadmill 802 comprise center of pressure (COP) values for the subject (e.g., center of pressure values for the right and left legs of the subject). In this further embodiment, the data acquisition/data processing device 820 is further configured to determine a right and left leg step length of the subject from the center of pressure values for the subject, to determine how closely the right leg step length of the subject conforms to the left leg step length of the subject, and to generate the sensory output signal for the biofeedback based upon the conformity of the right leg step length of the subject to the left leg step length of the subject (e.g., in the manner described above with reference to FIG. 40). Also, in this further embodiment, the data acquisition/data processing device 820 is configured to receive the one or more position data signals from the body position measurement system 860, and to determine a center of gravity for the subject from the one or more position data signals. The data acquisition/data processing device 820 is further configured to determine a postural sway of the subject using the center of gravity determined from the one or more position data signals of the body position measurement system 860 (e.g., determine an anterior-posterior postural sway or a lateral postural sway from the body position measurement system 860), to determine how closely the postural sway of the subject conforms to one or postural sway baseline values (e.g., to an elliptical baseline envelope, similar to that described above with regard to FIG. 42), and to additionally generate the sensory output signal for the biofeedback based upon the conformity of the postural sway of the subject to the one or postural sway baseline values. As such, in this further embodiment, the feedback provided to the subject may be based upon both the upper and lower body movements of the subject. Also, in this further embodiment, the data acquisition/data processing device 820 may compare the gait parameters (e.g., the postural sway of the subject) determined for the upper body portion of the subject to the gait parameters determined for the lower body portion of the subject (e.g., the right and left leg step lengths of the subject) to determine whether or not a correlation exists between the gait parameters for the upper body portion of the subject and the gait parameters determined for the lower body portion of the subject (e.g., when there is a significant deviation between the right and left leg step lengths of the subject, the subject may also exhibit an upper body postural sway that is outside of the normal range, i.e., greater than the baseline envelope).

Any of the features or attributes of the above described embodiments and variations can be used in combination with any of the other features and attributes of the above described embodiments and variations as desired.

While the exemplary force plate systems explained above employ forces plate assemblies 102, 202, 302, 402, 502, 602, 702 that are configured to receive a subject in an upright position, it is to be understood that the invention is not so limited. Rather, the present invention can be practiced with a force plate assembly that measures the forces exerted by the limbs of a subject that is disposed in a position other than an upright position, such as subject in a substantially horizontal position. For example, a dual force assembly could be mounted on a vertical surface (e.g., the vertical side of a swimming pool) to measure the substantially horizontal forces exerted on the vertical surface by the arms and/or the legs of the subject.

Although the invention has been shown and described with respect to a certain embodiment or embodiments, it is apparent that this invention can be embodied in many different forms and that many other modifications and variations are possible without departing from the spirit and scope of this invention. For example, in some embodiments of the invention, a virtual reality system is provided in conjunction with the dual force plate system so that the subject can be tested while experiencing a variety of different simulated scenarios.

While exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system comprising, in combination:
    an instrumented treadmill configured to receive a subject, the instrumented treadmill including:
        one or more displaceable components, the one or more displaceable components having one or more respective surfaces for receiving one or more respective limbs of the subject; and
        at least one force transducer, the at least one force transducer configured to sense one or more measured quantities and output one or more load signals that are representative of one or more loads being applied to the one or more respective surfaces of the one or more displaceable components by the subject;
    a data processing device operatively coupled to the at least one force transducer of the instrumented treadmill, the data processing device configured to receive the one or more load signals that are representative of the one or more loads being applied to the one or more respective surfaces of the one or more displaceable components by the subject, to convert the one or more load signals into one or more output load components, and to determine one or more gait parameters for the subject from the one or more output load components, the data processing device further configured to compare the one or more gait parameters determined for the subject to one or more respective predetermined values or to compare a first of the one or more gait parameters for the subject to a second of the one or more gait parameters for the subject, the data processing device additionally configured to determine how closely the one or more gait parameters determined for the subject conform to the one or more respective predetermined values or to determine how closely the first of the one or more gait parameters for the subject conforms to the second of the one or more gait parameters for the subject, the data processing device further configured to generate a sensory output signal based upon the conformity of the one or more gait parameters of the subject to the one or more respective predetermined values or to generate a sensory output signal based upon the conformity of the first of the one or more gait parameters of the subject to the second of the one or more gait parameters of the subject; and a sensory output device operatively coupled to the data processing device, the sensory output device configured to receive the sensory output signal from the data processing device, to generate at least one of a visual indicator, an audible indicator, and a tactile indicator that is based upon the sensory output signal, and to output the at least one of the visual indicator, the audible indicator, and the tactile indicator to the subject in order to provide real-time sensory stimuli biofeedback to the subject as to conformity of the one or more gait parameters of the subject to the one or more respective predetermined values or biofeedback as to conformity of the first of the one or more gait parameters of the subject to the second of the one or more gait parameters of the subject, thereby enabling the subject to receive real-time biofeedback regarding his or her performance while he or she exercises on the instrumented treadmill so that the subject is able to make improvements to his or her gait based upon the real-time biofeedback received.

2. The force measurement system according to claim 1, wherein the one or more gait parameters determined for the subject comprise at least one of: (i) a step length of the subject, (ii) a maximum sway range of a center of pressure of the subject, (iii) a maximum sway range of the center of gravity of the subject, (iv) a time duration of a single leg stance of the subject, and (v) a time duration of a single leg swing of the subject.

3. The force measurement system according to claim 1, wherein the data processing device is configured to compare the one or more gait parameters determined for the subject to one or more respective predetermined values in order to determine gait deviations from a normal standard, the data processing device additionally being configured to determine how closely the one or more gait parameters determined for the subject conform to the one or more respective predetermined values, and to generate the sensory output signal based upon the conformity of the one or more gait parameters of the subject to the one or more respective predetermined values so as to provide biofeedback indicative of the gait deviations from the normal standard.

4. The force measurement system according to claim 1, wherein the data processing device is configured to compare a first of the one or more gait parameters for the subject to a second of the one or more gait parameters for the subject in order to determine asymmetry between a right leg and a left leg of the subject, the data processing device additionally being configured to determine how closely the first of the one or more gait parameters for the subject conforms to the second of the one or more gait parameters for the subject, and to generate the sensory output signal based upon the conformity of the first of the one or more gait parameters of the subject to the second of the one or more gait parameters of the subject so as to provide biofeedback indicative of the asymmetry between a right leg and a left leg of the subject.

5. The force measurement system according to claim 1, wherein the first and second of the one or more gait parameters determined for the subject comprise at least one of: (i) first and second time durations for respective right and left leg stance phases of the subject, (ii) first and second time durations for respective right and left leg swing phases of the subject, (iii) first and second step lengths for the respective right and left legs of the subject; and (iv) first and second ground reaction forces for the respective right and left legs of the subject.

6. The force measurement system according to claim 1, wherein the sensory output device comprises a visual display device having an output screen, and wherein the visual display device is configured to generate the visual indicator that provides biofeedback to the subject as to conformity of the one or more gait parameters of the subject to the one or more respective predetermined values or biofeedback as to conformity of the first of the one or more gait parameters of the subject to the second of the one or more gait parameters of the subject.

7. The force measurement system according to claim 1, wherein the sensory output device comprises a light emitting device, and wherein the light emitting device is configured to generate the visual indicator that provides biofeedback to the subject as to conformity of the one or more gait parameters of the subject to the one or more respective predetermined values or biofeedback as to conformity of the first of the one or more gait parameters of the subject to the second of the one or more gait parameters of the subject.

8. The force measurement system according to claim 1, wherein the sensory output device comprises an audio headset configured to be worn on a head of the subject or a speaker disposed on, or proximate to the instrumented treadmill, and wherein the audio headset or speaker is configured to generate the audible indicator that provides biofeedback to the subject as to conformity of the one or more gait parameters of the subject to the one or more respective predetermined values or biofeedback as to conformity of the first of the one or more gait parameters of the subject to the second of the one or more gait parameters of the subject.

9. The force measurement system according to claim 1, wherein the sensory output device comprises a vibratory device configured to be worn by the subject, and wherein the vibratory device is configured to generate the tactile indicator that provides biofeedback to the subject as to conformity of the one or more gait parameters of the subject to the one or more respective predetermined values or biofeedback as to conformity of the first of the one or more gait parameters of the subject to the second of the one or more gait parameters of the subject.

10. The force measurement system according to claim 1, further including:

a body position measurement system, the body position measurement system configured to detect the position of an upper body portion of the subject and output one or more position data signals that are representative of the position of the upper body portion of the subject, the upper body portion of the subject being disposed above the feet of the subject;

wherein the one or more gait parameters that the data processing device is configured to determine from the one or more load signals comprise center of pressure values for the subject;

wherein the data processing device is further configured to determine a right and left leg step length of the subject from the center of pressure values for the subject, to determine how closely the right leg step length of the subject conforms to the left leg step length of the subject, and to generate the sensory output signal for the biofeedback based upon the conformity of the right leg step length of the subject to the left leg step length of the subject;

wherein the data processing device is further operatively coupled to the body position measurement system, the data processing device being configured to receive the one or more position data signals from the body position measurement system, and to determine a center of gravity for the subject from the one or more position data signals; and wherein the data processing device is further configured to determine a postural sway of the subject using the center of gravity determined from the one or more position data signals, to determine how closely the postural sway of the subject conforms to one or more postural sway predetermined values, and to additionally generate the sensory output signal for the biofeedback based upon the conformity of the postural sway of the subject to the one or more postural sway predetermined values.

11. The force measurement system according to claim 10, wherein the body position measurement system comprises at least one of: (i) an infrared detector, (ii) an ultrasonic detector, (iii) a position detection device with mechanical linkage means, (iv) one or more inertial measurement units configured to be coupled to the upper body portion of the subject, (v) one or more video cameras, and (vi) a motion capture system.

12. A treadmill system with biofeedback, comprising, in combination:

a treadmill configured to receive a person, the treadmill including:

one or more displaceable components, the one or more displaceable components having one or more respective surfaces for receiving one or more respective limbs of the person; and one or more actuator mechanisms coupled to the one or more displaceable components, the one or more actuator mechanisms configured to displace the one or more displaceable components;

a body position measurement system, the body position measurement system configured to measure a position of a body portion of the person on the treadmill and output one or more signals that are representative of the position of the body portion of the person on the treadmill;

a data processing device operatively coupled to the body position measurement system, the data processing device configured to receive the one or more signals that are representative of the position of the body portion of the person, to convert the one or more signals into one or more body position values, and to determine one or more gait parameters for the person from the one or more body position values, the one or more gait parameters determined for the person including a center of gravity for the person, the data processing device further configured to compare the one or more gait parameters determined for the person to one or more respective predetermined values or to compare a first of the one or more gait parameters for the person to a second of the one or more gait parameters for the person, the data processing device additionally configured to determine how closely the one or more gait parameters determined for the person conform to the one or more respective predetermined values or to determine how closely the first of the one or more gait parameters for the person conforms to the second of the one or more gait parameters for the person, the data processing device further configured to generate a sensory output signal based upon the conformity of the one or more gait parameters of the person to the one or more respective predetermined values or to generate a sensory output signal based upon the conformity of the first of the one or more gait parameters of the person to the second of the one or more gait parameters of the person; and a sensory output device operatively coupled to the data processing device, the sensory output device configured to receive the sensory output signal from the data processing device, to generate at least one of a visual indicator, an audible indicator, and a tactile indicator that is based upon the sensory output signal, and to output the at least one of the visual indicator, the audible indicator, and the tactile indicator to the person in order to provide real-time sensory stimuli biofeedback to the person as to conformity of the one or more gait parameters of the person to the one or more respective predetermined values or biofeedback as to conformity of the first of the one or more gait parameters of the person to the second of the one or more gait parameters of the person, thereby enabling the subject to receive real-time biofeedback regarding his or her performance while he or she exercises on the treadmill so that the subject is able to make improvements to his or her gait based upon the real-time biofeedback received.

13. The treadmill system according to claim 12, wherein the one or more gait parameters determined by the data processing device for the person comprise at least one of: (i) a step length of the person, and (ii) a maximum sway range of the center of gravity of the person.

14. The treadmill system according to claim 12, wherein the data processing device is configured to compare the one or more gait parameters determined for the person to one or more respective predetermined values in order to determine gait deviations from a normal standard, the data processing device additionally being configured to determine how closely the one or more gait parameters determined for the person conform to the one or more respective predetermined values, and to generate the sensory output signal based upon the conformity of the one or more gait parameters of the person to the one or more respective predetermined values so as to provide biofeedback indicative of the gait deviations from the normal standard.

15. The treadmill system according to claim 12, wherein the data processing device is configured to compare a first of the one or more gait parameters for the person to a second of the one or more gait parameters for the person in order to determine asymmetry between a right leg and a left leg of the person, the data processing device additionally being configured to determine how closely the first of the one or more gait parameters for the person conforms to the second of the one or more gait parameters for the person, and to generate the sensory output signal based upon the conformity of the first of the one or more gait parameters of the person to the second of the one or more gait parameters of the person so as to provide biofeedback indicative of the asymmetry between a right leg and a left leg of the person.

16. The treadmill system according to claim 12, wherein the sensory output device comprises a visual display device having an output screen, and wherein the visual display device is configured to generate the visual indicator that provides biofeedback to the person as to conformity of the one or more gait parameters of the person to the one or more respective predetermined values or biofeedback as to conformity of the first of the one or more gait parameters of the person to the second of the one or more gait parameters of the person.

17. The treadmill system according to claim 12, wherein the sensory output device comprises a light emitting device, and wherein the light emitting device is configured to generate the visual indicator that provides biofeedback to the person as to conformity of the one or more gait parameters of the person to the one or more respective predetermined values or biofeedback as to conformity of the first of the one or more gait parameters of the person to the second of the one or more gait parameters of the person.

18. The treadmill system according to claim 12, wherein the sensory output device comprises an audio headset configured to be worn on a head of the person or a speaker disposed on, or proximate to the treadmill, and wherein the audio headset or speaker is configured to generate the audible indicator that provides biofeedback to the person as to conformity of the one or more gait parameters of the person to the one or more respective predetermined values or biofeedback as to conformity of the first of the one or more gait parameters of the person to the second of the one or more gait parameters of the person.

19. The treadmill system according to claim 12, wherein the sensory output device comprises a vibratory device configured to be worn by the person, and wherein the vibratory device is configured to generate the tactile indicator that provides biofeedback to the person as to conformity of the one or more gait parameters of the person to the one or more respective predetermined values or biofeedback as to conformity of the first of the one or more gait parameters of the person to the second of the one or more gait parameters of the person.

20. The treadmill system according to claim 12, wherein the body position measurement system comprises at least one of: (i) an infrared detector, (ii) an ultrasonic detector, (iii) a position detection device with mechanical linkage means, (iv) one or more inertial measurement units configured to be coupled to the body portion of the person, (v) one or more video cameras, and (vi) a motion capture system.

21. A force measurement system comprising, in combination:
an instrumented treadmill configured to receive a subject, the instrumented treadmill including:
one or more displaceable components, the one or more displaceable components having one or more respective surfaces for receiving one or more respective limbs of the subject; and
at least one force transducer, the at least one force transducer configured to sense one or more measured quantities and output one or more load signals that are representative of one or more loads being applied to the one or more respective surfaces of the one or more displaceable components by the subject;
a data processing device operatively coupled to the at least one force transducer of the instrumented treadmill, the data processing device configured to receive the one or more load signals that are representative of the one or more loads being applied to the one or more respective surfaces of the one or more displaceable components by the subject, to convert the one or more load signals into one or more output load components, and to determine one or more gait parameters for the subject from the one or more output load components, the data processing device further configured to generate at least one sensory output signal based upon the one or more gait parameters for the subject; and
a sensory output device operatively coupled to the data processing device, the sensory output device configured to receive the at least one sensory output signal from the data processing device, to generate at least one of a visual indicator, an audible indicator, and a tactile indicator that is based upon the at least one sensory output signal, and to output the at least one of the visual indicator, the audible indicator, and the tactile indicator to the subject in order to provide real-time sensory stimuli biofeedback to the subject as to a manner in which the one or more gait parameters of the subject change over time, thereby enabling the subject to receive real-time biofeedback regarding his or her performance while he or she exercises on the instrumented treadmill so that the subject is able to make improvements to his or her gait based upon the real-time biofeedback received.

22. The force measurement system according to claim 21, wherein the one or more displaceable components comprise a first displaceable component and a second displaceable component, the first displaceable component having a respective first surface for receiving a respective first limb of the subject and the second displaceable component having a respective second surface for receiving a respective second limb of the subject;
wherein the at least one force transducer comprises at least one first force transducer, the at least one first force transducer configured to sense one or more measured quantities and output one or more first load signals that are representative of forces or moments, or both forces and moments being applied to the first surface by the subject, and at least one second force transducer, the at least second force transducer configured to sense one or more measured quantities and output one or more second load signals that are representative of forces or moments, or both forces and moments being applied to the second surface by the subject;
wherein the data processing device is configured to receive the one or more first load signals that are representative of forces or moments, or both forces and moments being applied to the first surface and to convert the one or more first load signals into one or more first output load components, and to receive the one or more second load signals that are representative of forces or moments, or both forces and moments being applied to the second surface and to convert the one or more second load signals into one or more second output load components, the data processing device further configured to determine one or more first gait parameters for the subject from the one or more first output load components and to determine one or more second gait parameters for the subject from the one or more second output load components, the data processing device additionally configured to generate the at least one sensory output signal based upon the one or more first gait parameters and the one or more second gait parameters; and wherein the sensory output device is configured to generate at least one of a first visual indicator, a first audible indicator, and a first tactile indicator for the one or more first gait parameters of the subject based upon the at least one sensory output signal and at least one of a second visual indicator, a second audible indicator, and a second tactile indicator for the one or more second gait parameters of the subject based upon the at least one sensory output signal, and output the at least one of the first visual indicator, the first audible indicator, and the first tactile indicator and the at least one of the second visual indicator, the second audible indicator, and the second tactile indicator to the subject in order to provide real-time biofeedback as to a manner in which the one or more first and second gait parameters of the subject change over time.

\* \* \* \* \*